United States Patent
Roth et al.

(10) Patent No.: US 11,124,819 B2
(45) Date of Patent: Sep. 21, 2021

(54) GENES INVOLVED IN ASTAXANTHIN BIOSYNTHESIS

(71) Applicant: The Regents of the University of California, Oakland, CA (US)

(72) Inventors: Melissa S. Roth, Stanford, CA (US); Krishna K. Niyogi, Lafayette, CA (US); Sean D. Gallaher, Los Angeles, CA (US); Sabeeha Merchant, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 278 days.

(21) Appl. No.: 15/922,763

(22) Filed: Mar. 15, 2018

(65) Prior Publication Data

US 2019/0233867 A1   Aug. 1, 2019

Related U.S. Application Data

(60) Provisional application No. 62/471,887, filed on Mar. 15, 2017.

(51) Int. Cl.

| | |
|---|---|
| *C12P 23/00* | (2006.01) |
| *C12N 15/52* | (2006.01) |
| *C12N 1/12* | (2006.01) |
| *C12N 15/67* | (2006.01) |
| *C12N 15/79* | (2006.01) |
| *C12N 9/10* | (2006.01) |

(52) U.S. Cl.
CPC ............... *C12P 23/00* (2013.01); *C12N 1/12* (2013.01); *C12N 9/1025* (2013.01); *C12N 15/52* (2013.01); *C12N 15/67* (2013.01); *C12N 15/79* (2013.01); *C12Y 203/0102* (2013.01); *C12Y 203/0104* (2013.01); *C12Y 203/01158* (2013.01)

(58) Field of Classification Search
None
See application file for complete search history.

(56) References Cited

U.S. PATENT DOCUMENTS

2017/0137792 A1* 5/2017 Chang ................ C12N 15/815

OTHER PUBLICATIONS

Huang et al., Transcriptome analysis of Chlorella zofingiensis to identify genes and their expressions involved in astaxanthin and triacylglycerol biosynthesis, May 27, 2016, Algal Research, vol. 17, pp. 236-243 (Year: 2016).*
Zones et al., High-Resolution Profiling of a Synchronized Diurnal Transcriptome from Chlamydomonas reinhardtii Reveals Continuous Cell and Metabolic Differentiation, Oct. 2015, The Plant Cell, vol. 27, pp. 2743-2769 (Year: 2015).*
Roth et al. Chromosome-level genome assembly and transcriptome of the green alga Chromochloris zofingiensis illuminates astaxanthin production, May 8, 2017, PNAS, vol. 114, pp. E4296-4305 (Year: 2017).*
Chen et al. Enhanced production of astaxanthin by Chromocloris zofingiensis in a microplate-based culture system under high light irradiation. Available online Aug. 19, 2017. Bioresource Technology. vol. 245, pp. 518-519. (Year: 2017).*
Roth et al. Chromosome-level genome assembly and transcriptome of the green algae Chromocloris zofingienesis illuminates astaxanthin production. Published online May 8, 2017. PNAS. E4296-E4305. (Year: 2017).*
Blanc G, et al. (2012) the genome of the polar eukaryotic microalga Coccomyxa subellipsoidea reveals traits of cold adaptation. Genome Biol 13(5):R39.
Merchant SS, et al. (2007) The Chlamydomonas genome reveals the evolution of key animal and plant functions. Science 318(5848):245-251.
Blanc G, et al. (2010) The Chlorella variabilis NC64A genome reveals adaptation to photosymbiosis, coevolution with viruses, and cryptic sex. Plant Cell 22(9):2943-2955.
Bogen C, et al. (2013) Reconstruction of the lipid metabolism for the microalga *Monoraphidium neglectum* from its genome sequence reveals characteristics suitable for biofuel production. BMC Genomics 14:926.
Baroli I, Do AD, Yamane T, & Niyogi KK (2003) Zeaxanthin accumulation in the absence of a functional xanthophyll cycle protects Chlamydomonas reinhardtii from photooxidative stress. Plant Cell 15(4):992-1008.

* cited by examiner

*Primary Examiner* — Channing S Mahatan
(74) *Attorney, Agent, or Firm* — Kilpatrick Townsend & Stockton LLP

(57) ABSTRACT

The disclosure is directed to nucleic acid, host cell, and polypeptide compositions encoded by the unicellular green alga *Chromochloris zofingiensis*, methods of making such compositions, and method of using the compositions to produce astaxanthin.

12 Claims, 6 Drawing Sheets

Specification includes a Sequence Listing.

C. zofingiensis chromosomes then unplaceds and rDNA unit (Mbp in concatenated genome)

GENES INVOLVED IN ASTAXANTHIN BIOSYNTHESIS

CROSS-REFERENCE TO RELATED APPLICATIONS

This application claims priority benefit of U.S. Provisional Application No. 62/471,887, filed Mar. 15, 2017, which application is herein incorporated by reference for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Fellowship No. 2013-67012-21272 awarded by the U.S. Department of Agriculture. The government has certain rights in the invention.

BACKGROUND OF THE INVENTION

Microalgae have potential to help meet energy and food demands without exacerbating environmental problems. The unicellular green alga *Chromochloris zofingiensis* produces lipids for biofuels and a highly valuable carotenoid nutraceutical, astaxanthin; however, much remains unknown about the genome and regulation of metabolism in this alga

*C. zofingiensis* (division Chlorophyta, class Chlorophyceae, order Sphaeropleales) is a simple ~4 μm, unicellular, haploid, coccoid alga containing multiple mitochondria, which are visualized typically as a tubular network, and a single interconnected chloroplast that occupies ~40% of the cell volume and contains starch granules. Most of the mitochondria are in close association with either the nucleus or the chloroplast. However, neither flagella (cilia) nor pyrenoids were visually observed. Because of the lack of obvious morphological characteristics, *C. zofingiensis* was originally described as a *Chlorella* species (6), at times transferred to the genera *Muriella* and *Mychonastes*, and finally placed using molecular sequencing into the genus *Chromochloris* (7). Similar to its close relative, the model alga *Chlamydomonas reinhardtii*, *C. zofingiensis* exhibits multiple fission with temporal separation between cell growth and cell division. *C. zofingiensis* primarily divides into two or four daughter cells, but also can divide into 16, 32, or 64 cells (6). The regulation of cell division timing is unknown, but the daughter cells are the same size. Also like *C. reinhardtii* (8), the nucleus in *C. zofingiensis* divides prior to chloroplast division. Intriguingly, *C. zofingiensis* has an extremely high photoprotective capacity compared to other algae and plants (9). Moreover, under specific conditions, *C. zofingiensis* can dramatically increase the production of lipids and secondary carotenoids (3-5, 10). This alga produces triacylglycerols (TAGs), the preferred lipid precursor for biofuel products and accumulates these to some of the highest levels out of 96 microalgae analyzed (3). Thus, *C. zofingiensis* is presently considered one of the most promising biofuel feedstocks for commercial production.

Increased production of the highly valuable ketocarotenoid astaxanthin occurs in concert with accumulation of TAGs (4, 5). Astaxanthin has a broad range of commercial applications, including pharmaceuticals, nutraceuticals, cosmetics, food, and feed (11-13). Recent studies have highlighted the antioxidant and anti-inflammatory benefits of astaxanthin for applications in human health including cancer, cardiovascular disease, neurodegenerative disease, inflammatory disease, diabetes, and obesity treatments (11, 12). Although astaxanthin can be produced synthetically, naturally produced astaxanthin is distinct in its esterification and stereochemistry (13-15). These differences result in natural astaxanthin having >20-fold stronger antioxidant activity than synthetic astaxanthin, and only natural astaxanthin has been approved for human consumption (14). Because *C. zofingiensis* is fast growing, can be cultured under many conditions (including with wastewater), and reaches high culture densities, *C. zofingiensis* has higher potential to meet worldwide demand than other natural sources, such as the microalga Haematococcus pluvialis, yeast, transgenic plants, and crustaceans (13, 15-17). Thus, *C. zofingiensis* is a prime candidate to supply the world with natural astaxanthin as well as a source of renewable biofuel. However, improvements to maximize productivity and yield are needed, and key aspects of astaxanthin biosynthesis and regulation remain to be elucidated.

BRIEF SUMMARY OF THE INVENTION

We sequenced and assembled *C. zofingiensis* nuclear, mitochondrial, and plastid genomes using a hybrid approach, constructed a transcriptome from 14 diverse conditions, examined transcriptomic changes through a shift from normal growth to that in high light, generated and analyzed astaxanthin-deficient mutants, and identified candidate genes involved in algal astaxanthin biosynthesis. The high-quality, chromosome-level genome assembly and accompanying transcriptome, combined with the capacity for genetic transformation (18), establish a molecular foundation to facilitate commercial development of *C. zofingiensis*.

Astaxanthin is an important and valuable algal bioproduct. In microalgae, astaxanthin is often produced in high abundance under stressful conditions, consistent with the hypothesis that it confers protection against oxidative stress. However, astaxanthin is not coupled functionally or structurally to the photosynthetic apparatus. Instead, astaxanthin functions as an internal sunscreen and antioxidant by absorbing excess light and quenching reactive oxygen species. Additionally, astaxanthin accumulates in cytoplasmic lipid droplets where it could prevent peroxidation of fatty acids.

In one aspect, provided herein are polynucleotides and polypeptides that are participate in the astaxanthin pathway in microalgae; and host cells, including microalgae, plant, yeast, or other host cells, engineered to express such gene to provide for astaxanthin production and/or enhanced astaxanthin production.

Examples of host cells that can be engineered to express an astaxanthin polypeptide of the present invention include bacteria, yeast, fungi, plants, microalgae, cyanobacteria, and the like. Examples include microalgae and cyanobacteria.

BRIEF DESCRIPTION OF THE DRAWINGS

(FIG. 2A) Phylogram estimated from restriction to putative 1:1:1:1:1:1 orthologs is consistent with existing literature (27). (FIG. 2B) A proportional Venn diagram showing the partitioning of the 15,274 *Chromochloris zofingiensis* genes by the combination of presence and absence of *Monoraphidium neglectum*, *Chlamydomonas reinhardtii*, and *Arabidopsis thaliana* genes in the families to which the genes belong also suggests these three organisms in this order are increasingly distant from *C. zofingiensis*. (FIG. 2C) Scatterplots show scrambled syntenic blocks of conserved genes in the algal lineage (similar to FIG. 2, reference 23). (Organism pairs involving the highly fragmented assembly of *M. neglectum* are omitted.) Each plot uses those gene families that, for the two organisms selected, have exactly one primary gene a in the first organism and exactly one primary gene b in the second organism. A dot with x-, y-coordinates at the midpoints of the span of the coding sequences for a, b is drawn in red if a and b are on the same nominal genomic strands and in green if they are on opposite strands; dots are plotted in a randomized order. Order of assembly sequences (but not nucleotides within sequences) is permuted on both axes so as to compact and emphasize statistically enriched regions (indicated by orange background shading); small numbers running along edges of inside plot frames give relevant portions of the assembly's sequence names for sequences at least 0.5 Mbp in length. Rightward and downward are 5' to 3' on assembly plus strands and light gray lines mark assembly sequence boundaries. Further details are given in SI Text of the SI Appendix.

(FIG. 3A) HPLC traces of wild type, bkt1-1, bkt1-2, and bkt1-3 grown under high light (HL, 400-450 μmol photons m$^{-2}$ s$^{-1}$), showing the mutants' lack of astaxanthin production. Pigment abbreviations are as follows: N (neoxanthin), V (violaxanthin), Ast (astaxanthin), A (antheraxanthin), L (lutein), Z (zeaxanthin), Chl b (chlorophyll b) Chl a (chlorophyll a), α (α-carotene) and β (β-carotene). Pigments were detected at 445 nm with reference at 550 nm (SI Appendix, SI Text). Inset shows high light WT growth with astaxanthin resulting in orange-brown color from astaxanthin (orange) and chlorophylls (green), whereas mutants bkt1-1, bkt1-2, and bkt1-3 do not produce astaxanthin and remain green. Under medium light (ML, 100 μmol photons m$^{-2}$ s$^{-1}$), WT does not produce high amounts of astaxanthin and remains green with similar color as bkt1-1, bkt1-2, and bkt1-3. (FIG. 3B) Pigment levels (mean±SD, N=3 or 4) in HL-grown WT, bkt1-1, bkt1-2, and bkt1-3 showing higher levels of carotenoids with similar levels of chlorophyll. *p<0.05, p<0.01, *p<0.001 (see SI Appendix, SI Text).

(FIG. 4A) Principal component analysis (PCA) of the regularized log$_2$-transformed counts for all 44 samples. The two most significant components, accounting for 95% of variation, are shown. ML (triangles) and HL (circles) are displayed with time point indicated by color. (FIG. 4B) Differentially expressed genes during transition to HL. Expression fold change in HL versus ML was determined for each time point for all genes. Genes at least two-fold up-regulated or two-fold down-regulated are indicated by the height of the bar above or below the line, respectively (p<0.01); the total is indicated above each bar. The regularized log$_2$-transformed fold change between HL and ML is shown in the black box for each time point as indicated by color. For comparison, the fold change of each of these genes at the other time points is presented flanking the black box. The number of differentially-expressed genes in common between 0.5 and 1 h and between 0.5 and 12 h is indicated by square brackets.

DETAILED DESCRIPTION OF THE INVENTION

Figure 1:
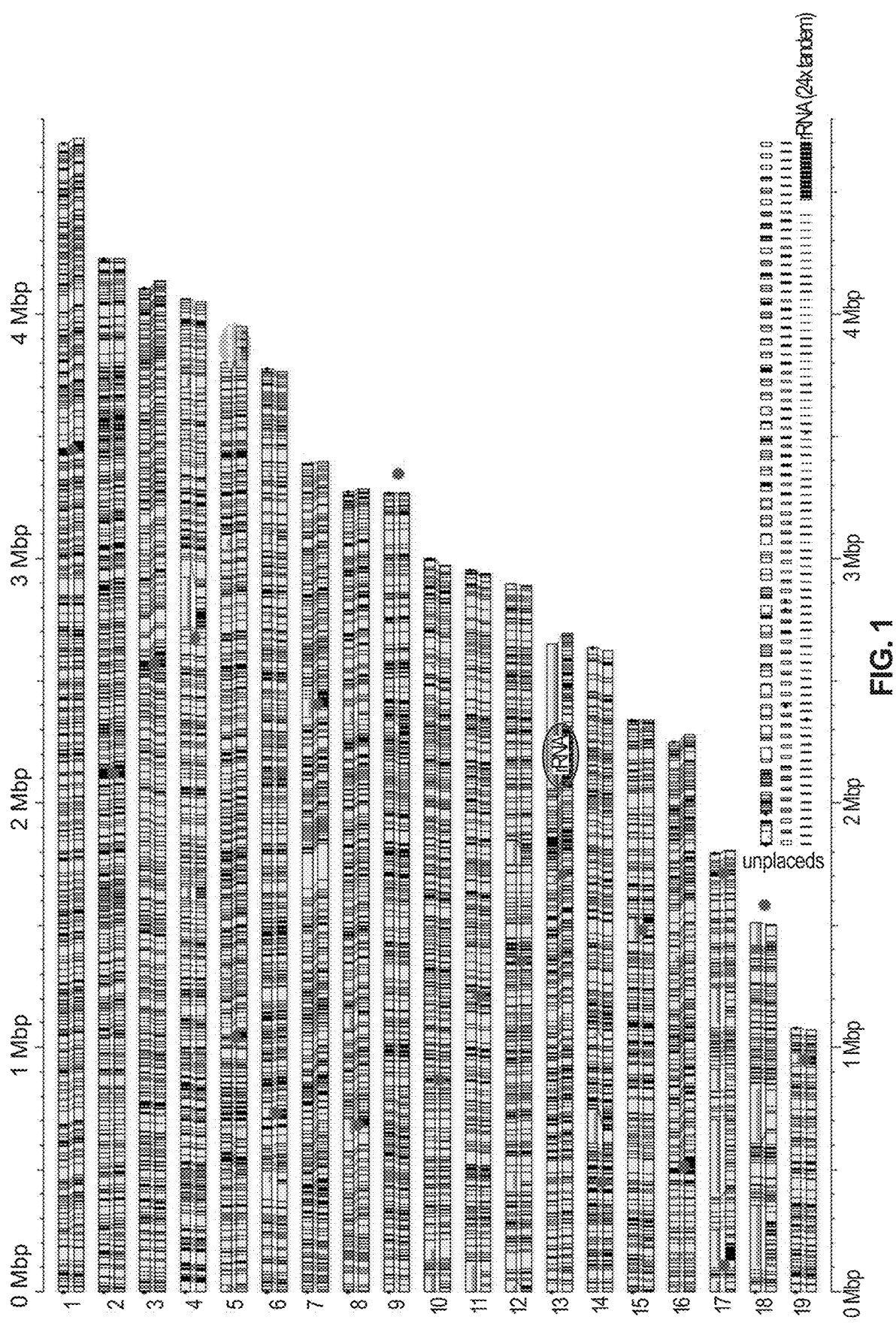
FIG. 1 *Chromochloris zofingiensis* nuclear genome. The assembled sequence of the 19 chromosomes of the nuclear genome is shown (top bar in each pair) with the matching chromosomes from the optical map (bottom bar in each pair). Nominal plus strands run 5' to 3' left to right. Thin vertical divisions mark BamHI restriction sites (in silico in top bars, optical consensus in bottom bars). Lines from restriction sites on one bar to another indicate a maximally-scoring alignment computed with a dynamic programming algorithm similar to that used in OpGen, Inc.'s MapSolver software. Black squares at chromosome edges indicate sequence assembly has reached telomere-associated repeats. Thick horizontal orange bars indicate explicit assembly gaps (runs of Ns). Thick horizontal yellow bars indicate additional known assembly issues as cataloged in SI File S4. Light blue background shading shows where alignments are not one-to-one; shading is light green otherwise. Red dots mark possible (peri)centromeric loci. Optical assembly did not reach the end of chromosome 5, and the large sequence gap at the end of chromosome 13 likely begins with ~24× copies of the rDNA unit. Unplaced contigs/scaffolds and 24 copies of the rDNA unit are shown near the bottom right.

The invention is based, in part, on the identification of genes in *C. zofingiensis* that are involved in astaxanthin production.

An "expression vector" or "expression cassette" is a nucleic acid construct, generated recombinantly by genetic engineering technology or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter. An "expression cassette" may also include embodiments in which a polynucleotide encoding a polypeptide of interest, such as an astaxanthin production protein is integrated into host DNA an a non-native position or is integrated into host DNA such that production of the protein is controlled by a heterologous promoter.

By "host cell" is meant a cell that is genetically modified to contain an exogenous nucleic acid that has been introduced into the host cell by recombinant DNA technology, e.g., an expression vector and supports the replication or expression of the expression vector. The term includes the progeny of the host cell that was initially genetically modified and thus includes the primary transformed cell and progeny derived therefrom without regard to the number of passages. Host cells may be prokaryotic cells including but not limited to, algae, including microalgae, plants, cyanobacteria, or eukaryotic cells including but not limited to, algae, yeast, insect, amphibian, or mammalian cells such as CHO, HeLa and the like, e.g., cultured cells, explants, and cells in vivo. molecule(s) present at one or more locations in a host cell.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this invention are those genes encoded by the same genetic locus.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 100 amino acids of SEQ ID NOS: 1-7), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et ai, Nucleic Acid Res. 19:5081 (1991); Ohtsuka et ai, J. Biol. Chem., 260:2605-2608 (1985); Rossolini et al., Mol. Cell. Probes, 8:91-98 (1994)). The term nucleic acid can be used interchangeably with gene, cDNA, mRNA, oligonucleotide, and polynucleotide.

The terms "wild type", "native", and "naturally occurring" with respect to an astaxanthin-production protein are used herein to refer to a protein that participated in astaxanthin production, e.g., having an amino acid sequence of any one of SEQ ID NOS:1-7 that has a sequence that occurs in nature.

In the context of this invention, the term "mutant" with respect to a mutant polypeptide or mutant polynucleotide is used interchangeably with "variant". A "non-naturally" occurring protein refers to a variant or mutant polypeptide that is not present in a cell in nature and that is produced by genetic modification, e.g., using genetic engineering technology or mutagenesis techniques, of a native polynucleotide or polypeptide. A "variant" includes any protein comprising at least one amino acid mutation with respect to wild type. Mutations may include substitutions, insertions, and deletions.

An "endogenous" protein or "endogenous" nucleic acid" is also referred to as a "native" protein or nucleic acid that is found in a cell or organism in nature.

A polynucleotide or polypeptide is "heterologous" to an organism or a second polynucleotide or polypeptide sequence if it originates from a foreign species, or, if from the same species, is modified by human action from its original form. For example, a "heterologous" sequence includes a native astaxanthin production protein having one or more mutations relative to the native amino acid sequence; or a native protein that is expressed in a host cell in which it does not naturally occur. In some embodiments, expression of an astaxanthin production polypeptide by a genetically modified host cell in accordance with the invention is under the control of a light-inducible promoter, e.g., a light-inducible promoter from a microlage or from another species, e.g., cyanobacteria, such as psb2 promoter.

In some embodiments, an "astaxanthin production protein" refers to a polypeptide that functions in astaxanthin production and has at least 70%, 75%, 80%, 85%, 90%, 91%, 92%, 93%, 94%, 95%, 96%, 97%, 98%, 99% or 100% identity to an amino acid sequence of any one of SEQ ID NOS:1-7.

The terms "increased expression" and "overexpression" of an astaxanthin production polypeptide are used interchangeably herein to refer to an increase in the amount of polypeptide in a genetically modified cell, e.g., a cell into which an expression construct encoding an astaxanthin polypeptide has been introduced, compared to the amount of polypeptide in a counterpart cell that does not have the genetic modification, i.e., a cell of the same strain or organism without the modification, such as a wildtype host cell. An increased level of expression for purposes of this application is at least 5%, or at least 10%, 20%, 30%, 40%, 50%, 60%, 70%, 80%, 90%, 100%, or greater, compared to the counterpart unmodified cell. The unmodified counterpart cell need not natively express the astaxanthin production polypeptide. Thus, the term "overexpression" also includes embodiments in which the polypeptide is expressed in a host cell that does not natively express the polypeptide. Increased expression can be assessed by any number of assays, including, but not limited to, measuring the level of RNA, the level of CVDE polypeptide, and/or the level of polypeptide activity. Illustrative assays are provided in the Examples section. "Overexpression" in the context of protein activity includes overexpression relative to endogenous activity such that the overall level of activity in the host cell is increased in the genetically modified host cell.

In some embodiments, a polynucleotide that encodes an astaxanthin production polypeptide as described herein, e.g., that has at least 70% identity, at least 75% identity, at least 80%, at least 85%, at least 90%, or at least 95% identity to any one of SEQ ID NOS:1-7; comprises a nucleic acid sequence having at least 60%, at least 65%, at least 70%, at least 75%, at least 80%, at least 85%, at least 90%, or at least 95% identity to any one of SEQ ID NOS:15-21. In some embodiments, the polynucleotide comprises a nucleic acid sequence having at least 60%, at least 65%, at least 70%, at least 75%, at least 80%, at least 85%, at least 90%, or at least 95% identity to any one of SEQ ID NOS:8-14. In some embodiments, the nucleic acid sequence is codon-optimized for expression in the host cell.

Expression constructs encoding an astaxanthin production polypeptide as provided by the present disclosure can be prepared using any method. For example, a DNA sequence encoding a astaxanthin protein, can be combined with transcriptional and other regulatory sequences which will direct the transcription of the sequence from the gene in the intended cells, e.g., C. zofingiensis cells. In some embodiments, an expression vector that comprises an expression cassette that comprises the nucleic acid sequence endogenous the astaxanthin production protein further comprises a promoter operably linked to the nucleic acid sequence. In other embodiments, a promoter and/or other regulatory elements that direct transcription of the astaxanthin nucleic acid sequence are endogenous to the host cell or organism, and an expression cassette comprising the astaxanthin gene is introduced, e.g., by homologous recombination, such that the astaxanthin gene is operably linked to an endogenous promoter and is expression driven by the endogenous promoter.

In some embodiments, the promoter may be from a gene associated with photosynthesis or lipid production in the species to be transformed or another species. For example such a promoter from one species may be used to direct expression of a protein in transformed algae cells. Suitable promoters may be isolated from or synthesized based on known sequences from other photosynthetic organisms.

In some embodiments a promoter may be a constitutive promoter. In some embodiments the promoter is an inducible promoter. In some embodiments, a promoter can be used to direct expression of astaxanthin nucleic acids under the influence of changing environmental conditions.

In some embodiments, the host cell is an algal host cell, e.g., a green algae host cell, such as unicellular green algal host cell. In some embodiments, the host cell is a C. zofingiensis host cell.

Examples

Whole-Genome Sequencing, Assembly, and Global Architecture.

For whole-genome sequencing and chromosome-level assembly of C. zofingiensis (strain SAG 211-14), we used a hybrid approach blending short reads (Illumina), long reads (Pacific Biosciences of California, Inc.) and whole-genome optical mapping (OpGen, Inc.). The combined power of these multiple approaches yielded a high-quality haploid nuclear genome of C. zofingiensis of ~58 Mbp distributed over 19 chromosomes (FIG. 1). About 99% of reads from the Illumina genomic libraries were accounted for, and non-placeholder chromosomal sequence covers ~94% of the optical map. Because genome assembly methods used were not automated, details of the procedure are described in the SI Text of the SI section below.

Genome features of C. zofingiensis were compared to four other green algae: C. reinhardtii, Coccomyxa subellipsoidea C-169, Chlorella sp. NC64A, and Monoraphidium neglectum (the closest relative with a sequenced genome), and the model plant Arabidopsis thaliana (Table 1, SI section text). Similar to most green algae, C. zofingiensis has a genome that is approximately half the size of A. thaliana and C. reinhardtii; yet C. zofingiensis and all known algal genomes have more than double the number of chromosomes of A. thaliana. However, C. zofingiensis has the most balanced G+C content (both for the nuclear genome and just coding sequence) of the six organisms (~51% and 53%, respectively); while C. subellipsoidea C-169 is similar to C. zofingiensis, the other algal genomes have high G+C content, and A. thaliana has low G+C content. High G+C content is associated with more fragmentary assemblies. C. sp. NC64A has large number of regions with distinct G+C content, but C. zofingiensis does not. The relative repetitive content of the C. zofingiensis genome, like C. subellipsoidea C-169, appears to be low (≈6%); in contrast, the M. neglectum genome has ≈50% higher and C. sp. NC64A≈100% higher relative repetitive content despite comparable genome sizes among these four algae. The large genomes of C. reinhardtii and A. thaliana have roughly double the relative repetitive content compared to the highest of the other four. After C. subellipsoidea C-169, C. zofingiensis contains the most repetitive fraction from novel repeats not known in Repbase Update (19), which presently focuses on A. thaliana and C. reinhardtii. In C. zofingiensis, gene density is quite uniform over chromosomes, and there are no grand scale gradients in genes or repeats as found in, for example, A. thaliana where each chromosome has megabasepairs of pericentromeric heterochromatin (20). However, some smaller scale gradients in repeats are found near large assembly gaps and putative (peri)centromeres. RepeatMasker in conjunction with RepeatModeler and Repbase finds ~5.0% of C. zofingiensis sequence consists of interspersed repeats (~2.0% LINEs, ~1.5% LTRs, ~1.2% unclassified, and ~0.4% DNA elements) with the remainder mostly simple repeats (~1.0%) and with some satellites, low complexity sequence, and small RNA (total ~0.1%).

Complete (circular with no gaps or IUPAC ambiguities) mitochondrial and chloroplast genomes for *C. zofingiensis* strain UTEX 56 (formerly *Bracteacoccus cinnabarinus*) were already available as NCBI accessions KJ806268.1 (21) and KT199251.1 (22), respectively. We independently assembled equivalent complete genomes de novo for strain SAG 211-14 (Table 1, SI section). These two strains were isolated from similar habitats in localities ~300 km apart by different people in sequential years. For the mitochondrial genome, the SAG and UTEX strains were resolved as 41,733 bp and 44,840 bp, respectively, with the same major protein-coding genes, tRNAs, and rRNAs in the same order (SI section) (21). However, a pairwise alignment exhibited only ~66% nucleotide identity, with divergence concentrated intergenically and in rrnL4 where splicing differs. Restricted to coding sequence, nucleotide identity rises to ~98%, and amino acid identity is ~99% in translations under the NCBI *Scenedesmus obliquus* mitochondrial genetic code. For the chloroplast genome, the SAG and UTEX strains resolved as 181,058 bp and 188,935 bp, respectively, with a ~6.7 kbp and ~6.4 kbp, respectively, rRNA-related inverted repeat (SI section) (22). Neither the Illumina short reads nor Pacific Biosciences long reads were able to resolve the relative strand orientation of the two single copy regions for the SAG strain; a single contig was constructed with an arbitrary relative orientation which is opposite that given for the UTEX strain. Again, between the strains, all major protein-coding genes, tRNAs, and rRNAs are the same in the same order. I n comparisons between strains, the single copy regions were reoriented to agree. Nucleotide identity was estimated at ~83%, with divergence concentrated intergenically and with the largest single difference being a loss in the SAG strain of almost all of a ~9.3 kbp UTEX region annotated as containing a ptz-like ORF. Coding sequence identity is ~98%, and translation under the NCBI bacterial, archaeal, and plant plastid code gives ~97% amino acid identity with lower identity in larger proteins (e.g., FtsH, RpoC2, and Ycf1).

The current *C. zofingiensis* assembly successfully extended into telomere-associated repeats for 25 of 38(=19+19) chromosome tips, and unplaced contigs may represent another 11 tips leaving only two tips unaccounted. The *C. zofingiensis* canonical unit appears to be $(CCCTAAA)_n$ at 5' ends (and the reverse complement, $(TTTAGGG)_n$, at 3' ends), similar to *C. subellipsoidea* C-169 and *C. sp.* NC64A and likely *M. neglectum*, although *C. reinhardtii* may prefer $(CCCTAAAA)_n$. A comparison of counts of apparently telomere-associated reads vs. generic nuclear reads (and constraints imposed by the optical map) suggested an average of ≈3.5 kbp of repeats per chromosome tip.

Based on experience with particularly difficult sequence during assembly phases and analysis of the chromosomal distributions of specific dispersed and tandem repeat families, one region per chromosome was identified as a putative (peri)centromeric locus in most chromosomes. These loci are complex nested insertions of a ~4.7 kbp circular consensus sequence that consists of ~4 kbp coding sequence of a Type I/Copia LTR retrotransposon together with a ~0.7 kbp spacer, as well as some 5S rDNA sequence (but apparently no large tandem arrays of a relatively short unit, such as in *A. thaliana*); the best NCBI BLASTX hits are to the filamentous green alga *Klebsormidium flaccidum* and the colonial green alga *Volvox carteri*. In the current *C. zofingiensis* version 5 assembly, 39 unplaced assembly sequences contain homology to the consensus unit. These regions are reminiscent of the Zepp clusters described in *C. subellipsoidea* C-169 (23), although the Zepp element is LINE-like and not of LTR type. Various analyses (including constraints imposed by the optical map) provided a rough estimate of only ~25 kbp on average of (peri)centromere per chromosome in *C. zofingiensis*.

The canonical rDNA repeat unit of *C. zofingiensis* became apparent early in assembly due to its presence in relatively high copy number. It assembled as a 9,702 bp circular contig annotated by RNAmmer 1.2 as ~6.6 kbp 28S followed by ~1.1 kbp of spacer followed by ~1.8 kbp 18S followed by ~0.2 kbp of spacer. From the presence of homologous sequence on chromosome 13 leading into the large sequencing gap of that chromosome, the optical tandem repeat that begins that sequencing gap, and the presence of two BamHI sites in the consensus rDNA unit (creating alternating fragments of ~6.0 kbp and ~3.7 kbp that are consistent with the optical tandem repeat), it is estimated that ~24× tandem copies of the rDNA unit predominate in the first ~40% of the large sequence gap of chromosome 13. Various analyses (e.g., Table 1) assume 24 exact copies begin this gap. The estimated number of copies is similar to *M. neglectum*, but much less than in the large genomes of *A. thaliana* and *C. reinhardtii*. The presence of other arrays of rDNA besides that of chromosome 13 cannot be completely ruled out (for example, neither sequence assembly nor the optical map reached one end of chromosome 5).

Genome Annotation and Transcriptomics

To facilitate annotation, we generated a *C. zofingiensis* transcriptome using RNA-Seq data collected from cells grown under 14 diverse conditions designed to capture a significant fraction of the cell's transcriptional repertoire (SI section). These conditions included treatments of different light intensities, nutrient limitations, and oxidative stress. Paired-end sequencing of transcriptome libraries was performed to facilitate determination of splice junctions, resolve close paralogous families, and de novo assembly (used as part of training the AUGUSTUS ab initio gene caller). In order to capture non-polyadenylated transcripts such as those from mitochondria and the chloroplast, libraries were prepared from total RNA depleted of rRNA.

RNA-Seq coverage, in conjunction with the de novo transcriptome assembly, was used to select a gene prediction method for producing gene models. Multiple pipelines, including Softberry's Fgenesh, MAKER (24), and AUGUSTUS (25) were evaluated using metrics such as RNA-Seq coverage capture and intron/exon boundary correlation with coverage. Of all evaluated pipelines, we selected AUGUSTUS as trained on the de novo transcriptome, which identified 15,274 nucleus-encoded protein-coding genes of which 15,194 are apparently complete.

When the RNA-Seq libraries were aligned to the genome assembly, 95±2% of reads aligned uniquely (mean±SD, N=10) and an additional 3±1% aligned to multiple locations, suggesting that the genome assembly represents nearly all coding genes. Further, 55±3% of RNA-Seq reads overlap by at least 80% with the coding portion of a gene model on the correct strand (mean±SD, N=10); only 1.3±0.3% overlap with a gene model on the opposite strand. Current gene models do not include 5' and 3' UTRs; extending gene models 1000 bp upstream and downstream increases the percentage of reads aligning to the correct strand to 96±2%.

Figure 2A:
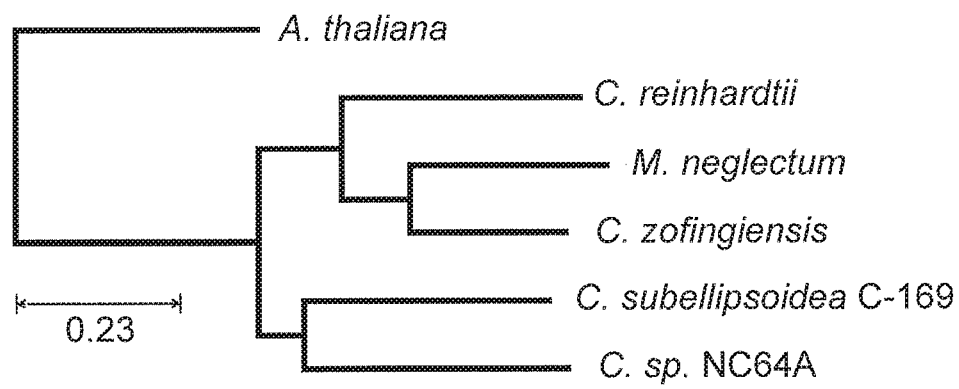
FIG. 2A-2C. Gene families. Using a procedure based on reciprocal near-best global amino acid alignments, protein-coding gene families among the six organisms of Table 1 were formed.
Figure 2B:
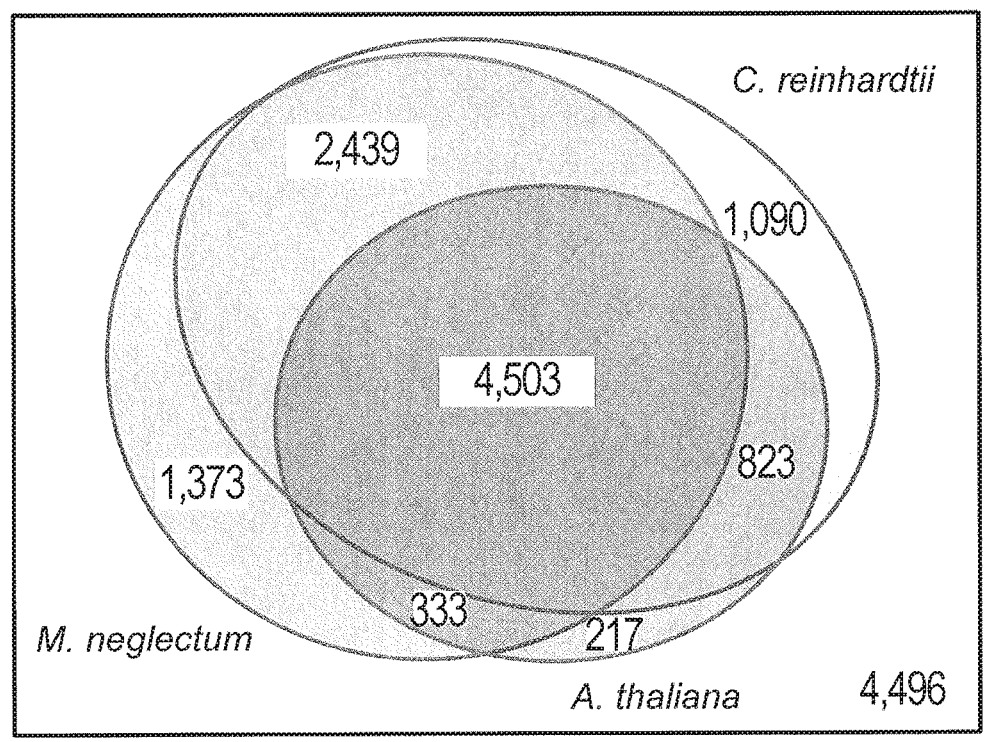
Figure 3A:
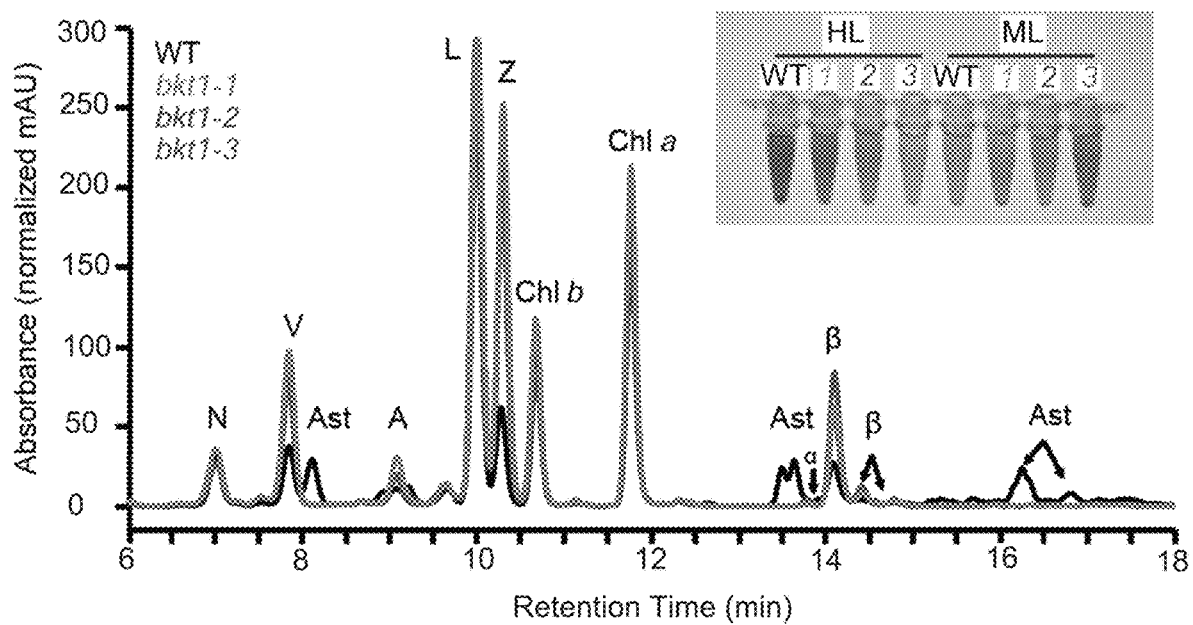
FIG. 3A-3B. *Chromochloris zofingiensis* astaxanthin-deficient mutants. Astaxanthin-deficient mutants were generated using forward genetics; mutations were identified in BKT1.
Figure 3B:
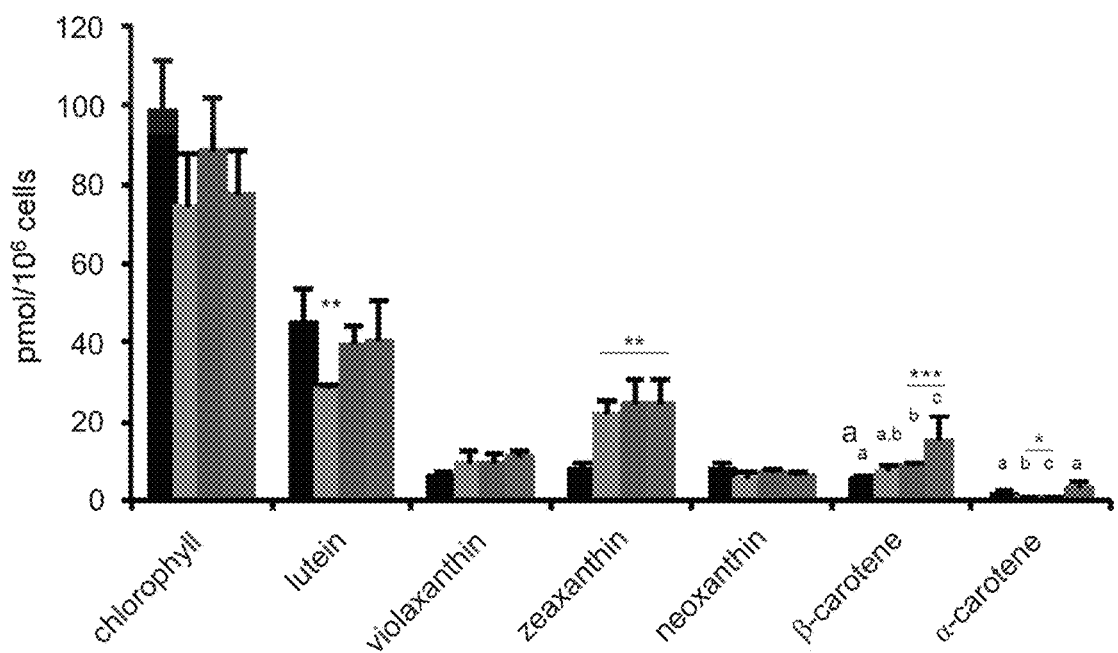

To further quantify the completeness of the assembly and annotations, an analysis was performed by BUSCO (26) to identify *C. zofingiensis* orthologs for a set of 302 genes commonly found in eukaryotes. Orthologs were identified for 90.8% of these genes in the genome, with 98% of those genes judged to be complete by BUSCO (FIG. 3B, SI section). At the proteome level, orthologs were identified for 93.1% of the set, with 90.1% of those judged to be complete. BUSCO analyses on the other photosynthetic organisms show that *C. zofingiensis* gene model quality is comparable to that of *C. subellipsoidea* C-169 and *C. sp.* NC64A, superior to *M. neglectum* but inferior to model organisms *C. reinhardtii* and *A. thaliana* (FIG. 2B). Moreover, these analyses show that *C. zofingiensis* genome quality is higher than other algae and has less fragmented and missing orthologs (FIG. 2B). As expected, *A. thaliana* has many more repeated genes orthologs than the algae (FIG. 2B).

The sequences of all *C. zofingiensis* genes submitted to the NCBI nucleotide database were compared to the assembly presented here. For 12 out of 13 different genes, there was 99% or greater identity and 1% or fewer gaps as determined by BLAST alignment to the genome (SI section, Table S4). Only one, heat shock protein 70 (accession AY072815.1), had limited homology, but was isolated from a different strain.

*C. zofingiensis* contains the highest predicted fraction (~39%) of protein-coding sequence of the six organisms in Table 1. The average length of its coding sequences (~482 aa) is the longest apart from outlier *C. reinhardtii*, which helps bring *C. reinhardtii* to almost as high a fraction of coding sequence even though its genome is much larger. The median length of *C. zofingiensis* coding sequences (~347 aa) is, however, more ordinary. The length of individual coding exons (whether by mean ~291 bp or median ~194 bp) of *C. zofingiensis* is the longest among the six organisms, while the mean (~5.0) and median (4) number of coding exons per gene is low, being more similar to *M. neglectum* and *A. thaliana* rather than the higher numbers seen in the other algae. The number of identified tRNA loci (75 and forming a complete set for the standard amino acids) is moderate like *C. subellipsoidea* C-169, rather than very low as for *C. sp.* NC64A and *M. neglectum*, or high for the two large genomes of *C. reinhardtii* and *A. thaliana*.

To compare the *C. zofingiensis* proteome to others in the green lineage, we functionally annotated gene models by forming families of genes across the six organisms of Table 1 using a method based on reciprocal near-best global amino acid alignments (SI section). This analysis generally permits one, many, or no genes per organism per family and separates genes into closer "primary" (putative orthologs) vs. further "additional" relationships (putative paralogs). The result contains 10,490 families involving more than one organism, of which 7,904 involve at most two genes per organism. There are some large families, with various histones constituting the largest families. ~73% of *C. zofingiensis* genes (and ≥~60% of every genome) are placed in a family involving multiple organisms. All six genomes (including *C. zofingiensis*) show evidence of tandem duplication of genes. A phylogram (FIG. 2A) estimated from putative 1:1:1:1:1:1 orthologs placed *C. zofingiensis* closest to *M. neglectum* and then *C. reinhardtii* (also in agreement with counts of *C. zofingiensis* genes as partitioned by their status as regards representation in *M. neglectum*, *C. reinhardtii*, and *A. thaliana*, FIG. 2B), forming a three-member Glade that joins a two-member Glade containing *C. subellipsoidea* C-169 and *C. sp.* NC64A, consistent with existing literature (27), and this whole-genome data analysis is in agreement with placing this alga into the genus *Chromochloris* (7).

Figure 2C:
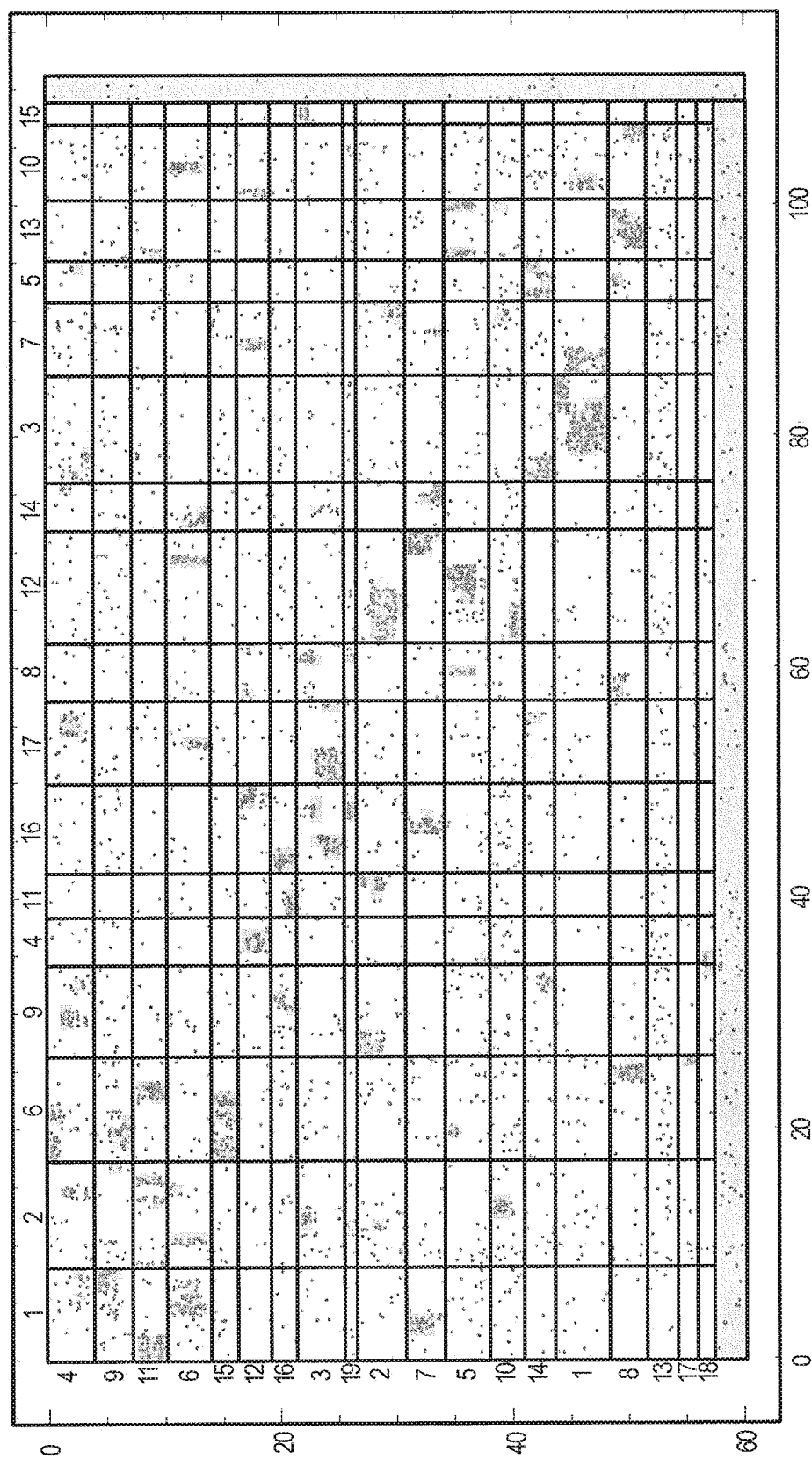

Although we do not find large stretches of nucleotide synteny between *C. zofingiensis* and the other genomes, we do find among all members in the green algal lineage (except for *M. neglectum*, whose current assembly is too fragmented for such an analysis) highly significant genomically localized blocks of genes in putative orthologous relationships (FIG. 2C and SI section), extending the result for *C. subellipsoidea* C-169 vs. *C. sp.* NC64A (FIG. 1). While block boundaries are rather well defined, gene order and coding strands within blocks are generally completely scrambled. It is likely that the blocks represent random chromosomal rearrangements that accumulate over time and diverge after speciation. Synteny analyses were also used to evaluate evolution of the green lineage, which resulted in topology consistent with the phylogram presented (FIG. 2, SI section).

To gain more insight into the metabolic function and cellular processes associated with specific proteins, we used in silico methods to predict subcellular localization of proteins encoded by the nuclear genome of *C. zofingiensis*. Using PredAlgo, an algal-specific subcellular localization prediction program trained on *C. reinhardtii* (28), we predicted nucleus-encoded proteins to distribute as ~15% to the secretory system, ~12% to the chloroplast, and ~10% to mitochondria. The majority of proteins (~63%) were predicted to be localized to other areas, which may be due to unidentified transit peptides, or the transit peptides of *C. zofingiensis* being significantly different from PredAlgo's *C. reinhardtii* training set. Additionally, errors in gene models, especially in terminal regions, may result in inaccurate localization predictions. The predicted distribution is similar to what has been noted for *C. reinhardtii* (29).

Mitochondrial and chloroplast genes were highly expressed over a wide range of conditions (SI section). Despite the organellar genomes being significantly smaller and expressing many fewer genes, the transcripts expressed by the chloroplast and mitochondria represent a substantial portion of the total cellular mRNA. In an analysis of the transcriptomic data from 14 diverse growth conditions, 31±9% and 7±2% of total RNA-Seq reads uniquely mapped to the chloroplast and mitochondrion genomes, respectively (mean±SD). With few genes, this translates to dramatically higher expression per gene: for the 73 protein-coding genes encoded in the chloroplast and 22 in the mitochondria, median transcript abundance across conditions was 686 and 419 FPKMs, respectively, in contrast to 5 FPKMs across all nuclear-encoded genes.

To identify genes that were more highly regulated under specific conditions, we compared expression of every gene over the 14 conditions and selected those with z-scores beyond ±2, plotting these as heatmaps (SI section, data not shown). The most prominent treatment to affect nuclear and plastid gene expression was oxidative stress by hydrogen peroxide (SI section), which significantly affected 3,934 genes. These genes were enriched for ABC-transporter domains ($p=1.0\times10^{-6}$), suggesting that export of toxics and xenobiotics is a significant mechanism for handling environmental stress in *C. zofingiensis*. Similarly, singlet oxygen stress induced by the chemical Rose Bengal affected 1,477 genes (SI section) and heterotrophic growth on glucose identified 853 genes (SI section). Nutrient deprivation had similar effects on most genes and far fewer genes were identified by analyses; for example, only 21 genes were detected as highly enriched in the iron-deficient sample.

Cryptic Sex and Motility in *C. zofingiensis*.

While *C. zofingiensis* has long been assumed to be asexual and non-motile, we investigated the presence of putative cilia/flagella and meiosis genes in its genome via the computationally identified gene families in conjunction with examination of associated gene expression across our conditions. The sequencing of the genome of C. sp. NC64A established a precedent for this type of analysis in green algae; similar to C. zofingiensis, no sexual cycle nor flagella has been observed in C. sp. NC64A, yet its genome revealed meiosis-specific and primarily motile flagella genes suggesting a cryptic sexual cycle (30). In the C. zofingiensis genome, we found putative orthologs of 73 of 78 genes (~94%) in the CiliaCut (31) suggesting that it is likely that there could be a previously unobserved motile life cycle stage with flagella in this organism. C. zofingiensis was missing only five genes: DLC4, FAP111, FBB5, IFT20, and Tctex1 (all gene symbols in this work are with implicit "[v5.2]" suffixes). In C. reinhardtii, the ift20 deletion mutant lacks flagella and is immotile (32), but perhaps C. zofingiensis has an as-yet unidentified gene with similar function. C. zofingiensis does seem to have critical C. reinhardtii genes for flagella motility (FLA14, 33) and forming flagella (PF15, PF19), including conservation of functional residues in these two genes (34, 35). Additionally, FLA14, PF15, and PF19 were expressed in a variety of conditions, which suggests that these genes are functional despite lacking a visible flagella. Furthermore, we identified putative orthologs of 25 of 40 C. reinhardtii meiosis-associated genes (30, 36), which was more than we observed for C. sp. NC64A (only 22 of 40). In C. zofingiensis, most of these genes are transcribed under many conditions, but a few such as GSP1, MER3, and DMC1 had low transcript abundance except under a low dose of Rose Bengal (5 µM Rose Bengal, 0.5 h dark and 1 h 100 µmol photons m$^{-2}$ s$^{-1}$). Eleven of the families not found in C. zofingiensis were specific to C. reinhardtii. While these data cannot rule out the possibility of that a sexual cycle was recently lost, it is more likely that the high number of apparent cilia/flagella and meiosis genes suggest the existence of sexual reproduction and a motile stage that has not yet been observed in C. zofingiensis. Life cycle studies and in particular investigations for a cryptic sexual cycle, which may require specific conditions, should be the subject of future research in C. zofingiensis.

Astaxanthin Biosynthesis Pathway and Astaxanthin-Deficient Mutants.

Astaxanthin is an important and valuable algal bioproduct. In microalgae, astaxanthin is often produced in high abundance under stressful conditions, consistent with the hypothesis that it confers protection against oxidative stress. However, astaxanthin is not coupled functionally or structurally to the photosynthetic apparatus. Instead, astaxanthin functions as an internal sunscreen and antioxidant by absorbing excess light and quenching reactive oxygen species (13, 15). Additionally, astaxanthin accumulates in cytoplasmic lipid droplets where it could prevent peroxidation of fatty acids (13, 15). Astaxanthin is synthesized via the carotenoid biosynthetic pathway, which has been previously reviewed (15, 37, 38); however, key steps in its biosynthesis are still undetermined. Most of what is known about astaxanthin biosynthesis in algae comes from studies of H. pluvialis, for which we lack a sequenced genome. It is thought that β-carotene is exported from the chloroplast into lipid droplets in H. pluvialis where astaxanthin is synthesized by the introduction of two keto-groups catalyzed by a di-iron beta-ketolase (BKT), which is followed by the introduction of two hydroxyl groups catalyzed by a hydroxylase (CHYB) (15, 39). However, the mechanisms of export and transport remain elusive. In contrast, it is hypothesized that, in C. zofingiensis, the hydroxylation of β-carotene occurs first and that astaxanthin is formed by the ketolation of zeaxanthin (13). In vitro enzymatic studies of C. zofingiensis genes show that BKT catalyzes the ketolation of β-carotene to canthaxanthin and zeaxanthin to astaxanthin, while CHYB catalyzes the hydroxylation of β-carotene to zeaxanthin but not of canthaxanthin to astaxanthin (13). Liu et al. (13) also concluded there was only one copy of BKT and CHYB present in C. zofingiensis, however a recent study suggests there are two copies of BKT (40). For comparison, H. pluvialis has three BKT genes that are differentially regulated by environmental factors (41). In both microalgae, astaxanthin is esterified and stored in lipid droplets, however the acyltransferase enzyme involved has not been identified.

The genome of C. zofingiensis provides new insights into the astaxanthin pathway. The annotated carotenoid biosynthetic pathway in this alga (SI section, Table S2) appears to be very similar to that in C. reinhardtii (42). For example, there are four putative carotene hydroxylase genes, encoding three cytochrome P450s (two CYP97A and one CYP97C) and one di-iron type hydroxylase (CHYB). In addition, we found two putative BKT genes in the genome, in accordance with recent results (40). BKT1 and BKT2 contain highly conserved histidine motifs present in H. pluvialis and bacterial beta-ketolases (43, 44). These motifs are involved in iron binding and, in bacteria, mutations in them abolish the ability to form ketocarotenoids (44). The BKT genes from microalgae share highly conserved regions and are more similar to each other than those from bacteria. PredAlgo predicts the localization of both BKT1 and BKT2 to "other" areas of the cell, which could support localization of these enzymes to the cytosol. However, this prediction has not yet been verified experimentally. The genome also shows that there is a wide distribution of carotenoid biosynthesis genes across many chromosomes as is typical in eukaryotes.

To study C. zofingiensis astaxanthin production using a non-biased approach, a genetic screen was conducted to identify genes essential for astaxanthin synthesis. C. zofingiensis cells were randomly mutated using ultraviolet radiation, grown on glucose medium to induce astaxanthin accumulation (13), and 65 colonies were identified that were visibly green rather than pink due to lack of astaxanthin production, which was subsequently confirmed by HPLC analysis (SI section). Similar HPLC chromatograms were observed for all mutants (data not shown). Initially, three strains were selected for sequencing of BKT1 and BKT2, and all three showed different single mutations in highly conserved areas of BKT1 but no mutations in BKT2, and thus these mutants were named bkt1-1, bkt1-2, and bkt1-3 (SI Appendix, Table S3, Table S4). When grown in high light, the mutants accumulated increased levels of astaxanthin precursor compounds, especially zeaxanthin but also β-carotene, as well as more violaxanthin, despite similar levels of other pigments (FIG. 3, SI section). BKT1 was sequenced in an additional 13 mutants, and all showed mutations in conserved regions of the gene (SI section, Table S3). These data suggest that the disruption of BKT1 alone is sufficient to abolish astaxanthin production, but we cannot unambiguously distinguish if the committed step toward astaxanthin begins with β-carotene or zeaxanthin. While the screen demonstrates that the BKT1 enzyme is required for astaxanthin biosynthesis, based on these results we cannot determine if BKT2 is non-functional or if it may act in a secondary reaction downstream of BKT1. Both BKT1 and BKT2 were highly expressed in response to $H_2O_2$-stress (876 and 367 FPKMs, respectively), and both were identified in the screen for $H_2O_2$ treatment-enriched genes. To a lesser extent, both were expressed in response to Rose Bengal treatment (394 and 35 FPKMs). It is unlikely that BKT1 and BKT2 form an obligate heterodimer or function in parallel pathways, as then mutations in either BKT1 or BKT2 should have been detected in different mutant strains.

High Light Induced Gene Expression.

To investigate the physiological changes associated with acclimation to high light and to elucidate unidentified genes in the astaxanthin biosynthesis pathway in *C. zofingiensis*, an RNA-Seq experiment was conducted in which cultures were moved from normal growth light intensity (100 µmol photons $m^{-2}$ $s^{-1}$) to high light intensity (400 µmol photons $m^{-2}$ $s^{-1}$) (SI Appendix, SI Text). Cultures were collected for nuclear, plastid, and mitochondrial gene expression analyses at 0, 0.5, 1, 3, 6, and 12 h (N=4) after the shift to high light, as well as in control cultures, which were maintained at the normal growth light intensity (SI section).

Figure 4A:
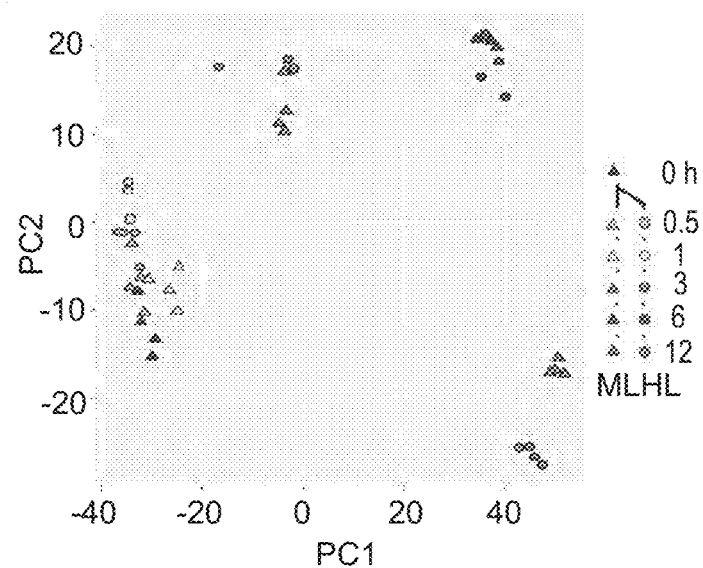
FIG. 4A-4B. *Chromochloris zofingiensis* RNA expression during transition to high light. Cultures of *C. zofingiensis* were grown diurnally (16 h light, 8 h dark) in 100 μmol photons m$^{-2}$ s$^{-1}$ medium light (ML). At t=0, cultures were transferred to 400 μmol photons m$^{-2}$ s$^{-1}$ high light (HL). Samples were collected in quadruplicate at 0, 0.5, 1, 3, 6, and 12 h for ML cultures and at 0.5, 1, 3, 6, and 12 h for HL. Transcript abundances for each sample were determined by RNA-Seq.

A principal component analysis of the regularized $log_2$-transformed counts from the resulting transcriptome profiles shows that time and treatment explain nearly all observed variation in gene expression between the conditions (95%, FIG. 4A). Time induces the largest variation for both the control and treatment cultures, which may have been caused by the diurnal lighting regime; these cultures were maintained on a day-night cycle (16 h light, 8 h dark) with sampling during daylight hours. The large changes throughout the day are not surprising given that in *C. reinhardtii* over 80% of the transcriptome is differentially expressed with diurnal periodicity (45). In addition to time-of-day changes, there is also a substantial effect from the shift to high light, as evidenced by the distinct groupings of control and treatment samples. Control cultures at each time point were used to separate the effects of time from high light.

Figure 4B:
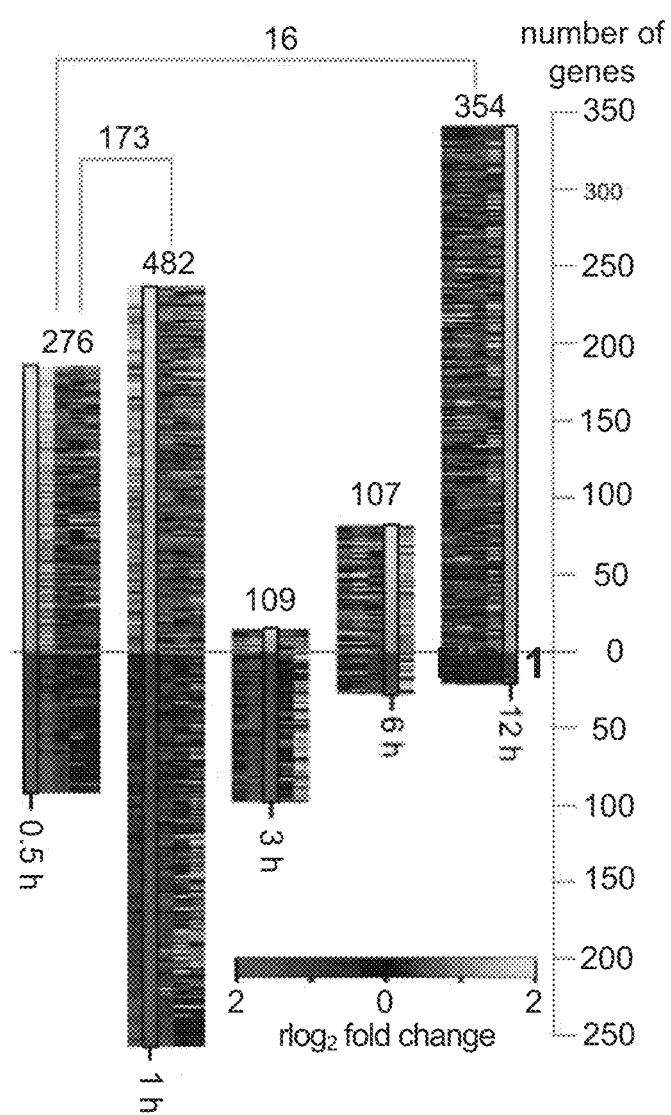

To further evaluate the effect of high light, differentially expressed genes at each time point were identified. Those genes whose expression had a greater than two-fold change (p<0.01) in either direction between the high light-treated cultures and controls were determined and visualized in a heatmap, scaled relative to the number of genes in each group (FIG. 4B). Most genes were differentially expressed either early in the experiment (276 genes at 0.5 h and 492 genes at 1 h) or late (362 genes at 12 h). The greatest overlap of significantly differentially expressed genes was during the early time points (0.5 and 1 h), unsurprising given that these samples were collected closest together in time. Additionally, during these early time points, high light had a greater effect than time (FIG. 4A). Over the course of the experiment, there was greater upregulation of significantly differentially expressed genes with 67%, 75%, and 94% of genes upregulated at 0.5, 6, and 12 h, respectively, but more genes were significantly downregulated at 1 h (52%) and 3 h (86%). Most genes had relatively modest changes (<4 fold) in the cultures shifted to high light, although expression of ELIP8 (early light-induced protein) and ELIP10 had >20-fold increases at 0.5 h. Among chloroplast-encoded genes, both psaA and atpF had significant upregulation at 1 h. No significantly differentially expressed mitochondrial genes were found during the shift to high light.

Figure 5:
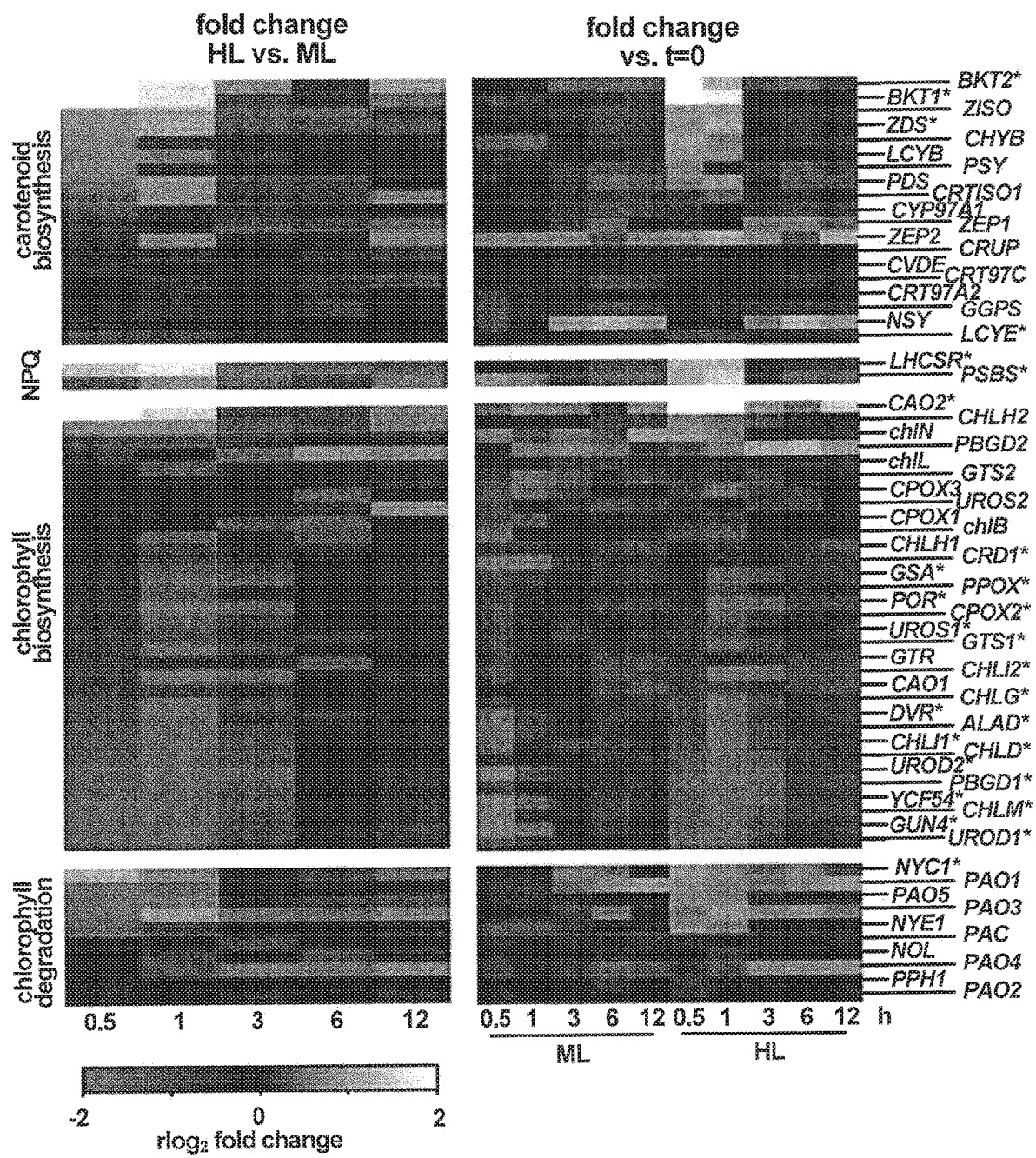
FIG. 5. *Chromochloris zofingiensis* RNA-Seq expression of select genes during the transition to high light. RNA-Seq was performed on cultures following a shift from medium light (ML, 100 μmol photons m$^{-2}$ s$^{-1}$) to high light (HL, 400-450 μmol photons m$^{-2}$ s$^{-1}$) as described in FIG. 4. *C. zofingiensis* genes potentially involved in carotenoid biosynthesis, non-photochemical quenching (NPQ), and chlorophyll biosynthesis and degradation were identified by manual curation. On the left, the regularized log 2-transformed fold-change between HL and ML for each of these genes at each time point is plotted as a heatmap. On the right, the regularized log$_2$-transformed fold-change between each time point relative to t=0 is plotted. Significantly differential genes that are over two-fold up- or down-regulated are indicated by an asterisk and bold text (p<0.01).

Because of the high level of interest in astaxanthin production in *C. zofingiensis*, we examined the genes involved in carotenoid biosynthesis during the shift to high light. High light causes an accumulation of secondary carotenoids (in particular, astaxanthin) in *C. zofingiensis* (46-48). In the present study, both BKT1 and BKT2 have the highest increase in gene expression, which occurs immediately after the light shift at 0.5 h (FIG. 5). Despite the increase in BKT2 gene expression in high light, its role in carotenoid biosynthesis has not been established. Many genes at various points in the carotenoid biosynthesis pathway were upregulated early (0.5 h and 1 h) in response to the high light treatment, including phytoene synthase (PSY) (FIG. 5), which catalyzes the committed step in carotenoid biosynthesis. Previous studies have reported similar upregulation of PSY, PDS, BKT, and CHYB at longer time points in response to increases in light (46, 49, 50). However, our study also revealed a significant increase in expression of ZDS at 1 h and a significant decrease in LCYE shortly after the shift to high light. Further, downregulation of many genes in the carotenoid biosynthesis pathway was observed at later time points (6 and 12 h) in both the treatment and control cultures; this is likely an effect of the diurnal cycle. A higher expression of carotenoid biosynthesis genes would support an increase in secondary carotenoids, but does not exclude the possibility that post-translational modifications of carotenoid biosynthetic enzymes may also account for the accumulation of secondary carotenoids during high light.

The high-quality genome and transcriptome we generated in combination with the high light RNA-Seq experiment allowed us to identify candidates for additional genes involved in astaxanthin biosynthesis and accumulation. As mentioned above, little is known about the mechanism of translocation of the astaxanthin precursor(s) out of the chloroplast, the hydroxylation of the astaxanthin precursor, transport of astaxanthin into lipid droplets, or the esterification of astaxanthin. We identified putative genes involved astaxanthin biosynthesis through examining the significantly differentially expressed genes with high increases in gene expression during the shift to high light for genes with protein activity compatible with hypothetical mechanisms of astaxanthin biosynthesis. Genes that are upregulated early during high light that may be implicated in the astaxanthin pathway include four ABC transporters (Cz04g21110, Cz05g17060, Cz09g27180, and Cz08g16130), two cytochrome P450 proteins (Cz10g28330 and Cz11g14160), and an acyltransferase (Cz02g29020). The ABC transporters may form a complex that exports the astaxanthin precursor(s) from the chloroplast. The cytochrome P450 proteins could be involved in hydroxylation of astaxanthin precursors in the cytosol, and the acyltransferase could be involved in esterification of astaxanthin.

In addition to changes in carotenoid biosynthesis, we also investigated other algal high light responses, including photoprotective mechanisms and chlorophyll metabolism. In photosynthetic organisms, excess light must be safely dissipated to prevent oxidative damage. *C. reinhardtii* transiently expresses PSBS at the onset of high light and LHCSR proteins accumulate under high light, and this accumulation is correlated with non-photochemical quenching capacity (51, 52). While *C. reinhardtii* has multiple copies of both LHCSR and PSBS (51, 52), we found only single copies of LHCSR and PSBS in *C. zofingiensis*, despite having high non-photochemical quenching capacity (9). As expected, both LHCSR and PSBS were upregulated at the early time points during the shift to high light and, in particular, at 1 h, which is consistent with observations of *C. reinhardtii* during the dark-to-light transition (45). Similar to the carotenoid biosynthesis genes, under the diurnal cycle LHCSR and PSBS are downregulated by the end of the day (6 and 12 h) in both conditions (FIG. 5). Reduction in chlorophyll is another common physiological response of algae exposed to high light (53). Accordingly, during the shift to high light, many *C. zofingiensis* genes involved in chlorophyll synthesis were downregulated and chlorophyll degradation genes were upregulated (FIG. 5). The combination of these would lead to a reduction in chlorophyll content either during acclimation or as a stress response to high light.

Annotation of Metabolic Pathways and Photosynthesis-Related Gene

Genes encoding homologs of the primary metabolic pathway enzymes involved with carbon, carotenoids, chlorophyll, fatty acids, and lipids, as well as proteins involved in the composition, assembly, and regulation of the photosynthetic apparatus, were preliminarily identified using the BLAT sequence search tool (54) against one of our *C. zofingiensis* draft genomes (SI section, Table S2). Based on the quality of the alignments and comparison to well-characterized, closely related plant and algal query sequences, the targeted gene models in *C. zofingiensis* were submitted as queries in reciprocal BLAST searches against the NCBI RefSeq non-redundant protein database to confirm coverage, domain architecture, and similarity across closely related homologs. Because of the high quality of the *C. zofingiensis* assembly, this procedure resulted in a nearly complete list of putative genes needed to complete each pathway. Identified gene models were used to assess the quality of the automated gene family analysis across the six species of Table 1, and the automated analysis was used to confirm additional candidate models and expand the set of annotations. Based on high sequence similarities and conservation of functional domains, we are generally confident in the assignments of homology for these models. However, it is possible that additional functional isoforms composed of more divergent sequences may also be present, having been missed by the parameters used for BLAT, BLAST, and the automated gene family analysis.

Identification and annotation of genes involved in lipid biosynthesis can provide targets for exploitation of *C. zofingiensis* for biofuel production. Using other oleaginous organisms as a guide, we would expect a robust oil-producing microalga to have an expanded family of acyltransferases. The *C. zofingiensis* diacylglycerol acyltransferases (DGAT) are too divergent from the protein sequences of Type 1 DGAT and DGTT (Type 2 DGATs, 55) in *C. reinhardtii*, *A. thaliana*, and *M. neglectum* to identify the corresponding genes via BLAT. Using a more sensitive BLAST search with both types of DGAT sequences from *C. subellipsoidea* C-169 (gi|545360296), *Chlorella vulgaris* (gb|ALP13863 0.1), *Nannochloropsis gaditana* (gb|EWM23187.1), *A. thaliana* (gi|15224779, gi|18409359), and *C. reinhardtii* (Cre01.g045903, Cre03.g205050), additional copies of DGAT Type 1- and DGTT-encoding genes were identified in *C. zofingiensis*, and yet more were identified using the automated gene family analysis. In total, 11 genes were identified that have either an LPLAT (lysophospholipid acyltransferase) domain or a closely related MBOAT (membrane bound O-acyltransferase) domain (SI Appendix, Table S2). We have tentatively assigned these genes as encoding proteins with diacylglycerol acyltransferase activity, however some of these *C. zofingiensis* gene models have higher similarity to predicted proteins of unknown function than to annotated Type 1 or Type 2 DGAT proteins from other closely related organisms. Our finding of multiple copies of putative DGAT and DGTT genes in *C. zofingiensis* is consistent with transcriptome results from the closely related ATCC 30412 strain (40). Of course, it is also possible, though unlikely, that one or multiple additional copies of DGAT or DGTT may be yet unidentified due to a gene modeling or assembly problem.

Homologous gene models were also identified for components of the photosynthetic apparatus and its assembly, including proteins that compose PSI, PSII, the major and minor light harvesting antennae, the cytochrome b6f complex, the chloroplast ATP synthase complex, and soluble electron carriers, as well as known assembly factors for these complexes (SI Appendix, Table S2). Thirteen of the *C. zofingiensis* light-harvesting complex (LHC) genes are predicted to be more like PSI-associated LHC genes (LHCAs) rather than nine PSII-associated LHC genes (LHCBs) (SI Appendix, Table S2), in contrast to the distribution found in *C. reinhardtii*, which has nine of each of LHCA and LHCB. Further experimental work is needed to confirm the expression profiles and photosystem association of each of these putative LHC proteins, especially under different light and stress conditions. Of note is one LHC model (Lhcb-like3, Cz04g24050) with little to no transcriptional expression detected in any of our RNA-Seq conditions.

Brief Summary of Above Examples

Our analyses of the *C. zofingiensis* genome, transcriptome, astaxanthin-deficient mutants, and RNA expression changes under high light reveal new insights into the basic biology of the green lineage of photosynthetic organisms and the carotenoid biosynthesis pathway. We present a high-quality chromosome-level assembly with independent genome validation including identification of (peri)centromeric loci for each chromosome and an assembly extending into telomere-associated tips for the majority of chromosomes. The compact ~58 Mbp genome has balanced G+C content and is rich in protein-coding sequence with few long exons per gene and relatively little repetitive sequence. We identified ortholog families for the majority of *C. zofingiensis* genes. The gene density is uniform over chromosomes and a syntenic comparison with other algae uncovered highly significant genomically localized blocks of genes in putative orthologous relationships; however, gene order and strands within blocks are scrambled. We have shown that BKT1 is critical for the production of astaxanthin and have identified candidate genes that could be involved in missing steps in astaxanthin biosynthesis and accumulation. The addition of genomics to the experimental toolkit for *C. zofingiensis* makes it a very attractive alga not only for fundamental studies of its biology but also the economically viable and environmentally sustainable production of biofuels and important bioproducts.

Table 1 shows the features of the *Chromochloris zofingiensis* genome in comparison to selected previously sequenced genomes. The *C. zofingiensis* genome was compared to four other green algal genomes (*Chlamydomonas reinhardtii*, *Coccomyxa subellipsoidea* C-169, *Chlorella* sp. NC64A, and *Monoraphidium neglectum*) and the model plant *Arabidopsis thaliana*. Quantities were generally computed with uniform rules applied to most recently available genome assemblies and annotation releases (SI Appendix, SI Text).

TABLE 1

Features of the *Chromochloris zofingiensis* genome in comparison to selected previously sequenced genomes. The *C. zofingiensis* genome was compared to four other green algal genomes (*Chlamydomonas reinhardtii*, *Coccomyxa subellipsoidea* C-169, *Chlorella* sp. NC64A, and *Monoraphidium neglectum*) and the model plant *Arabidopsis thaliana*. Quantities were generally computed with uniform rules applied to most recently available genome assemblies and annotation releases (SI Appendix, SI Text).

| | *Coccomyxa subellipsoidea* C-169 | *Chromochloris zofingiensis* | *Arabidopsis thaliana* |
|---|---|---|---|
| Nuclear genome | JGI Phytozome 2.0 assembly and gene models | This work ("ChrZofV5"): chroms. + unplaced + 24x copies of rDNA as single contig | TAIR10 assembly and gene models |
| Sequenced genome size | 49 Mbp | 57 Mbp | 119 Mbp |
| Sequenced genome presentation | 29.5 Mbp in 12 contiguous chroms., 19.1 Mbp in 16 contiguous chrom. arms (pairing not known for half), 333 Kbp in 17 unplaced contigs | 54.4 Mbp in 19 chroms. (4 ctg. + 15 scaf.), 2.4 Mbp in 198 unplaceds (171 ctg. + 27 scaf), 9.7 Kbp in 1 canonical rDNA unit contig | 119.0 Mbp in 5 scaffolded chromosomes |
| Sequenced genome: total # of stretches of pure "A"/"C"/"G"/"T" basepairs | 45 | 296 | 359 |
| Genome project primary initial strategy, average basepair coverage at earliest stage | Sanger WGS, ≈12x | HiSeq PE100, ≈460x | BAC/P1/TAC, complex |
| Scaffold N50 (taking genome size as sum of scaffolds as-are) | chromosomes/arms | chromosomes | chromosomes |
| | 1,960 Kbp | 1,444 Kbp | 10,898 Kbp |
| Contig N50 (taking genome size as sum of contigs as-are) | 20 (asm. subtelo./PFGE/Southerns) | 19 (optical map) | 5 (incontrovertible) |
| Number of chromosomes | | | |
| Percent G + C in sequenced genome | 53% | 51% | 36% |
| Basepairs called as coding (in any transcript model) in sequenced genome | 25% | 39% | 28% |
| Percent G + C in basepairs called as coding (in any transcript model) | 61% | 53% | 44% |
| Number of called protein-coding gene loci (collapsing transcript forms) | 9,629 | 15,274 | 27,206 |
| Number of "complete" called protein-coding gene loci (collapsing transcripts) | 8,815 | 15,194 | 27,197 |
| Number of rDNA units estimated to exist in true monoploid genome | unknown, no estimate | ≈24 on chrom. 13 | ≈375 NOR2 + 375 NOR4 |
| Number of tRNAs called in sequenced genome | 91 | 75 | 631 |
| Taking a single representative transcript model per called protein-coding gene locus: | | | |
| Number of amino acids: average | 427 aa | 482 aa | 407 aa |
| Number of amino acids: median | 333 aa | 347 aa | 350 aa |
| Number of exons containing coding sequence: average | 8.1 | 5.0 | 5.2 |
| Number of exons containing coding sequence: median | 7 | 4 | 3 |
| Exon length (restricted to coding sequence): average | 159 nt | 291 nt | 237 nt |
| Exon length (restricted to coding sequence): median | 144 nt | 194 nt | 133 nt |
| Intron length (between exons with coding sequence): average | 284 nt | 267 nt | 157 nt |
| Intron length (between exons with coding sequence): median | 246 nt | 260 nt | 98 nt |
| Percentage with at least one intron (between exons with coding sequence) | 94% | 82% | 76% |
| % of seq. basepairs RepeatMasker'd with Repbase Update "eukaryotic" | 2.2% | 3.7% | 18.0% |
| % of seq. basepairs RepeatMasker'd with RepeatModeler | 5.7% | 4.5% | 16.9% |
| % of seq. basepairs RepeatMasker'd with RepeatModeler + Repbase Update "eukaryo | 6.0% | 5.9% | 20.8% |
| Chloroplast genome | NCBI NC_015084.1 (with one gap and no large inv. rpt.) and annots. | This work ("ChrZofV5") | NCBI AP000423.1 sequence and annotations |
| Sequenced genome size | 176 Kbp | 181 Kbp | 154 Kbp |
| Number of annotated protein-coding genes, including hypotheticals | 80 | 71 | 86 |
| Number of annotated rRNAs | 3 | 6 | 8 |
| Number of annotated tRNAs | 32 | 31 | 37 |
| Percent G + C in sequenced genome | 51% | 31% | 36% |

TABLE 1-continued

Features of the Chromochloris zofingiensis genome in comparison to selected previously sequenced genomes. The C. zofingiensis genome was compared to four other green algal genomes (Chlamydomonas reinhardtii, Coccomyxa subellipsoidea C-169, Chlorella sp. NC64A, and Monoraphidium neglectum) and the model plant Arabidopsis thaliana. Quantities were generally computed with uniform rules applied to most recently available genome assemblies and annotation releases (SI Appendix, SI Text).

| Mitochondrial genome | NCBI NC_015316.1 sequence and annotations | This work ("ChZoIV5") | NCBI JF729201.1 sequence and annotations |
|---|---|---|---|
| Sequenced genome size | 65 Kbp | 42 Kbp | 367 Kbp |
| Number of annotated protein-coding genes, including hypotheticals | 31 | 22 | 32 |
| Number of annotated rRNAs | 3 | 6 | 3 |
| Number of annotated tRNAs | 26 | 24 | 21 |
| Percent G + C in sequenced genome | 53% | 36% | 45% |

| Nuclear genome | Chlamydomonas reinhardtii | Chlorella sp. NC64A | Monoraphidium neglectum |
|---|---|---|---|
| | JGI Phytozome 5.5 assembly and gene models | JGI release 2014-08-18 assembly and "best genes" models only | NCBI KK100223 thru KK106940 version. sequences and gene models |
| Sequenced genome size | 107 Mbp | 42 Mbp | 67 Mbp |
| Sequenced genome presentation | 105.1 Mbp in 17 scaffolded chromosomes, 2.0 Mbp in 37 unplaceds (15 contigs + 22 scaffolds) | 41.9 Mbp in 216 unplaced scaffolds + 322 Kbp in 198 unplaced contigs | 43.4 Mbp in 3,257 unplaced scaffolds + 23.7 Mbp in 3,461 unplaced contigs |
| Sequenced genome: total # of stretches of pure "A"/"C"/"G"/"T" basepairs | 1,547 | 3,957 | 12,074 |
| Genome project primary initial strategy, average basepair coverage at earliest stage | Plasmid/fosmid, ≈13x | Sanger WGS, ≈9x | MiSeqPE250, ≈49x |
| Scaffold N50 (taking genome size as sum of scaffolds as-are) | chromosomes | 1,470 Kbp | 16 Kbp |
| Contig N50 (taking genome size as sum of contigs as-are) | 215 Kbp | 28 Kbp | 9 Kbp |
| Number of chromosomes | 17 (linkage groups) | 12 (PFGE/asm. subtelo.) | unknown, no estimate |
| Percent G + C in sequenced genome | 64% | 67% | 65% |
| Basepairs called as coding (in any transcript model) in sequenced genome | 37% | 32% | 26% |
| Percent G + C in basepairs called as coding (in any transcript model) | 70% | 69% | 70% |
| Number of called protein-coding gene loci (collapsing transcript forms) | 17,741 | 9,791 | 16,734 |
| Number of "complete" called protein-coding gene loci (collapsing transcripts) | 17,685 | 8,509 | 14,268 |
| Number of rDNA units estimated to exist in true monoploid genome | ≈840 total chr. 1 + 7 + 15 | unknown, no estimate | ≈23 total |
| Number of tRNAs called in sequenced genome | 259 | 43 | 38 |
| Taking a single representative transcript model per called protein-coding gene locus: | | | |
| Number of amino acids: average | 736 aa | 456 aa | 348 aa |
| Number of amino acids: median | 500 aa | 358 aa | 265 aa |
| Number of exons containing coding sequence: average | 8.5 | 8.3 | 5.0 |
| Number of exons containing coding sequence: median | 7 | 7 | 4 |
| Exon length (restricted to coding sequence): average | 261 nt | 166 nt | 207 nt |
| Exon length (restricted to coding sequence): median | 133 nt | 119 nt | 129 nt |
| Intron length (between exons with coding sequence): average | 269 nt | 207 nt | 302 nt |
| Intron length (between exons with coding sequence): median | 228 nt | 171 nt | 254 nt |
| Percentage with at least one intron (between exons with coding sequence) | 92% | 98% | 82% |
| % of seq. basepairs RepeatMasker'd with Repbase Update "eukaryotic" | 17.8% | 8.9% | 8.1% |
| % of seq. basepairs RepeatMasker'd with RepeatModeler | 21.8% | 12.3% | 8.9% |
| % of seq. basepairs RepeatMasker'd with RepeatModeler + Repbase Update "eukaryo | 23.0% | 12.6% | 9.3% |

TABLE 1-continued

Features of the *Chromochloris zofingiensis* genome in comparison to selected previously sequenced genomes. The *C. zofingiensis* genome was compared to four other green algal genomes (*Chlamydomonas reinhardtii*, *Coccomyxa subellipsoidea* C-169, *Chlorella* sp. NC64A, and *Monoraphidium neglectum*) and the model plant *Arabidopsis thaliana*. Quantities were generally computed with uniform rules applied to most recently available genome assemblies and annotation releases (SI Appendix, SI Text).

| Chloroplast genome | NCBI FJ423446.1 sequence and annotations | NCBI KP271969.1 sequence (no large inv. rpt.) and annotations | NCBI CM002678.1 seq., paper's annotations |
|---|---|---|---|
| Sequenced genome size | 204 Kbp | 125 Kbp | 135 Kbp |
| Number of annotated protein-coding genes, including hypotheticals | 67 + 1 ncRNA (tscA) | 79 | 67 |
| Number of annotated rRNAs | 10 | 3 | 6 |
| Number of annotated tRNAs | 29 | 31 | 29 |
| Percent G + C in sequenced genome | 34% | 34% | 32% |

| Mitochondrial genome | NCBI NC_001638.1 sequence and annotations | NCBI NC_025413.1 sequence and annotations | NCBI CM002677.1 seq. (with two gaps) and annotations |
|---|---|---|---|
| Sequenced genome size | 16 Kbp | 78 Kbp | 93 Kbp |
| Number of annotated protein-coding genes, including hypotheticals | 8 | 32 | 17 |
| Number of annotated rRNAs | 14 | 3 | 0 |
| Number of annotated tRNAs | 3 | 27 | 23 |
| Percent G + C in sequenced genome | 45% | 28% | 46% |

REFERENCES

1. Stephens E, et al. (2010) Future prospects of microalgal biofuel production systems. *Trends Plant Sci* 15(10):554-564.
2. Wijffels R H, Barbosa M J (2010) An outlook on microalgal biofuels. *Science* 329(5993):796-799.
3. Breuer G, et al. (2012) The impact of nitrogen starvation on the dynamics of triacylglycerol accumulation in nine microalgae strains. *Bioresour Technol* 124:217-226.
4. Liu J, Mao X, Zhou W, Guarnieri M T (2016) Simultaneous production of triacylglycerol and high-value carotenoids by the astaxanthin-producing oleaginous green microalga *Chlorella zofingiensis*. *Bioresour Technol* 214:319-327.
5. Mulders K J M, et al. (2014) Effect of biomass concentration on secondary carotenoids and triacylglycerol (TAG) accumulation in nitrogen-depleted *Chlorella zofingiensis*. *Algal Res* 6:8-16.
6. Dönz O C (1934) *Chlorella zofingiensis*, eine neue Bodenalge. *Ber Schweiz Bot Ges* 43:127-123.
7. Fucikova K, Lewis L A (2012) Intersection of *Chlorella, Muriella* and *Bracteacoccus*: Resurrecting the genus *Chromochloris* KOL et CHODAT (Chlorophyceae, Chlorophyta). *Fottea* 12(1):83-93.
8. Goodenough U W (1970) Chloroplast division and pyrenoid formation in *Chlamydomonas reinhardii*. *J Phycol* 6(1):1-6.
9. Bonente G, et al. (2008) The occurrence of the psbS gene product in *Chlamydomonas reinhardtii* and in other photosynthetic organisms and its correlation with energy quenching. *Photochem Photobiol* 84(6):1359-1370.
10. Ip P F, Wong K H, Chen F (2004) Enhanced production of astaxanthin by the green microalga *Chlorella zofingiensis* in mixotrophic culture. *Process Biochem* 39(11):1761-1766.
11. Ghazi H, et al. (2006) Astaxanthin, a carotenoid with potential in human health and nutrition. *J Nat Prod* 69(3):443-449.
12. Yuan J-P, Peng J, Yin K, Wang J-H (2011) Potential health-promoting effects of astaxanthin: A high-value carotenoid mostly from microalgae. *Mol Nutr Food Res* 55(1):150-165.
13. Liu J, et al. (2014) *Chlorella zofingiensis* as an alternative microalgal producer of astaxanthin: biology and industrial potential. *Mar Drugs* 12(6):3487-3515.
14. Capelli B, Bagchi D, Cysewski G R (2013) Synthetic astaxanthin is significantly inferior to algal-based astaxanthin as an antioxidant and may not be suitable as a human nutraceutical supplement. *Nutrafoods* 12(4):145-152.
15. Solovchenko A E (2015) Recent breakthroughs in the biology of astaxanthin accumulation by microalgal cell. *Photosynthesis Res* 125(3):437-449.
16. Liu J, et al. (2013) Utilization of cane molasses towards cost-saving astaxanthin production by a *Chlorella zofingiensis* mutant. *J Appl Phycol* 25(5):1447-1456.
17. Zhu L, et al. (2013) Scale-up potential of cultivating *Chlorella zofingiensis* in piggery wastewater for biodiesel production. *Bioresour Technol* 137:318-325.
18. Liu J, et al. (2014) Genetic engineering of the green alga *Chlorella zofingiensis*: a modified norflurazon-resistant phytoene desaturase gene as a dominant selectable marker. *Appl Microbiol Biotechnol* 98(11):5069-5079.
19. Bao W, Kojima K K, Kohany O (2015) Repbase Update, a database of repetitive elements in eukaryotic genomes. *Mobile DNA* 6:11.
20. The *Arabidopsis* Genome Initiative (2000) Analysis of the genome sequence of the flowering plant *Arabidopsis thaliana*. *Nature* 408(6814):796-815.
21. Fucikova K, Lewis P O, Gonzalez-Halphen D, Lewis L A (2014) Gene arrangement convergence, diverse intron content, and genetic code modifications in mitochondrial genomes of Sphaeropleales (Chlorophyta). *Genome Biology Evol* 6(8):2170-2180.
22. Fucikova K, Lewis P O, Lewis L A (2016) Chloroplast phylogenomic data from the green algal order Sphaeropleales (Chlorophyceae, Chlorophyta) reveal complex patterns of sequence evolution. *Mol Phylogenet Evol* 98:176-183.
23. Blanc G, et al. (2012) The genome of the polar eukaryotic microalga *Coccomyxa subellipsoidea* reveals traits of cold adaptation. *Genome Biol* 13(5):R39.
24. Cantarel B L, et al. (2008) MAKER: An easy-to-use annotation pipeline designed for emerging model organism genomes. *Genome Res* 18(1):188-196.
25. Stanke M, Schoffmann O, Morgenstern B, Waack S (2006) Gene prediction in eukaryotes with a generalized hidden Markov model that uses hints from external sources. *BMC Bioinf* 7:62.
26. Simao F A, et al. (2015) BUSCO: assessing genome assembly and annotation completeness with single-copy orthologs. *Bioinformatics* 31(19):3210-3212.
27. Leliaert F, et al. (2012) Phylogeny and molecular evolution of the green algae. *Crit Rev Plant Sci* 31(1):1-46.
28. Tardif M, et al. (2012) PredAlgo: a new subcellular localization prediction tool dedicated to green algae. *Mol Biol Evol* 29(12):3625-3639.
29. Lopez D, et al. (2015) Dynamic changes in the transcriptome and methylome of *Chlamydomonas reinhardtii* throughout its life cycle. *Plant Physiol* 169(4):2730-2743.
30. Blanc G, et al. (2010) The *Chlorella variabilis* NC64A genome reveals adaptation to photosymbiosis, coevolution with viruses, and cryptic sex. *Plant Cell* 22(9):2943-2955.
31. Merchant S S, et al. (2007) The *Chlamydomonas* genome reveals the evolution of key animal and plant functions. *Science* 318(5848):245-251.
32. Engel B D, et al. (2009) Total internal reflection fluorescence (TIRF) microscopy of *Chlamydomonas flagella*. *Methods Cell Biol* 93:157-177.
33. Pazour G J, Wilkerson C G, Witman G B (1998) A dynein light chain is essential for the retrograde particle movement of intraflagellar transport (IFT). *J Cell Biol* 141(4):979-992.
34. Dymek E E, Smith E F (2012) PF19 encodes the p60 catalytic subunit of katanin and is required for assembly of the flagellar central apparatus in *Chlamydomonas*. *J Cell Sci* 125(14):3357-3366.
35. Dymek E E, Lefebvre P A, Smith E F (2004) PF15p is the *Chlamydomonas* homologue of the katanin p80 subunit and is required for assembly of flagellar central microtubules. *Eukaryot Cell* 3(4):870-879.
36. Ferris P J, Armbrust E V, Goodenough U W (2002) Genetic structure of the mating-type locus of *Chlamydomonas reinhardtii*. *Genetics* 160(1):181-200.
37. Lemoine Y, Schoefs B (2010) Secondary ketocarotenoid astaxanthin biosynthesis in algae: a multifunctional response to stress. *Photosynthesis Res* 106(1-2):155-177.
38. Takaichi S (2011) Carotenoids in algae: distributions, biosyntheses and functions. *Mar Drugs* 9(6):1101-1118.
39. Grunewald K, Hagen C (2001) β-carotene is the intermediate exported from the chloroplast during accumula- 40. Huang W, et al. (2016) Transcriptome analysis of *Chlorella zofingiensis* to identify genes and their expressions involved in astaxanthin and triacylglycerol biosynthesis. *Algal Res* 17:236-243.

41. Huang J C, Chen F, Sandmann G (2006) Stress-related differential expression of multiple beta-carotene ketolase genes in the unicellular green alga Haematococcus pluvialis. *J Biotechnol* 122(2): 176-185.

42. Lohr M, Im C S, Grossman A R (2005) Genome-based examination of chlorophyll and carotenoid biosynthesis in *Chlamydomonas reinhardtii. Plant Physiol* 138(1):490-515.

43. Huang J, et al. (2012) Cloning and selection of carotenoid ketolase genes for the engineering of high-yield astaxanthin in plants. *Planta* 236(2):691-699.

44. Ye R W, Stead K J, Yao H, He H (2006) Mutational and functional analysis of the beta-carotene ketolase involved in the production of canthaxanthin and astaxanthin. *Appl Environ Microbiol* 72(9):5829-5837.

45. Zones J M, Blaby I K, Merchant S S, Umen J G (2015) High-resolution profiling of a synchronized diurnal transcriptome from *Chlamydomonas reinhardtii* reveals continuous cell and metabolic differentiation. *Plant Cell* 27(10):2743-2769.

46. Li Y T, Huang J C, Sandmann G, Chen F (2009) High-light and sodium chloride stress differentially regulate the biosynthesis of astaxanthin in *Chlorella zofingiensis* (Chlorophyceae). *J Phycol* 45(3):635-641.

47. Del Campo J A, et al. (2004) Accumulation of astaxanthin and lutein in *Chlorella zofingiensis* (Chlorophyta). *Appl Microbiol Biotechnol* 64(6):848-854.

48. Rise M, et al. (1994) Accumulation of secondary carotenoids in *Chlorella zofingiensis. J Plant Physiol* 144(3): 287-292.

49. Cordero B F, et al. (2011) Enhancement of carotenoids biosynthesis in *Chlamydomonas reinhardtii* by nuclear transformation using a phytoene synthase gene isolated from *Chlorella zofingiensis. Appl Microbiol Biotechnol* 91(2):341-351.

50. Huang J C, Liu J, Li Y T, Chen F (2008) Isolation and characterization of the phytoene desaturase gene as a potential selective marker for genetic engineering of the astaxanthin-producing green alga *Chlorella zofingiensis* (Chlorophyta). *J Phycol* 44(3):684-690.

51. Correa-Galvis V, et al. (2016) Photosystem II subunit PsbS is involved in the induction of LHCSR-dependent energy dissipation in *Chlamydomonas reinhardtii. J Biol Chem* 291(33):17478-17487.

52. Peers G, et al. (2009) An ancient light-harvesting protein is critical for the regulation of algal photosynthesis. *Nature* 462(7272):518-U215.

53. Erickson E, Wakao S, Niyogi K K (2015) Light stress and photoprotection in *Chlamydomonas reinhardtii. Plant J* 82(3):449-465.

54. Kent W J (2002) BLAT—the BLAST-like alignment tool. *Genome Res* 12(4):656-664.

55. Boyle N R, et al. (2012) Three acyltransferases and nitrogen-responsive regulator are implicated in nitrogen starvation-induced triacylglycerol accumulation in *Chlamydomonas. J Biol Chem* 287(19):15811-15825.

Supplemental Information for Examples

*Chromochloris zofingiensis* Strains and Culture Conditions

*Chromochloris zofingiensis* strain SAG 211-14 was obtained from the Culture Collection of Algae at Goettingen University. The cells were grown at 25° C. in liquid cultures shaking at 100-150 rpm in diurnal (16 h light, 8 h dark) conditions with light intensity of 90-100 µmol photons $m^{-2}$ $s^{-1}$ unless stated otherwise. Cells were grown in Proteose Medium (UTEX Culture Collection of Algae) with Chu's micronutrient solution (2 mL/L, UTEX Culture Collection of Algae) unless stated otherwise. Cells were counted with the Multisizer 3 Coulter Counter (Beckman Coulter). Cells were harvested by centrifugation (2,200-4,620 g for 5-10 min), discarding the supernatant, resuspending the cells in media and transferring to an eppendorf tube, pelleting by centrifugation (15,000 g for 5 min), discarding the supernatant, and freezing the cell pellet in liquid nitrogen unless stated otherwise.

X-Ray Tomography

Cells were grown until log phase, pelleted by centrifugation (700 g for 2 min), and then loaded into custom-made thin-walled glass capillaries (1). Glass capillaries had been previously dipped in a solution of 100 nm gold nanoparticles (EMGC100, BBI International, Cardiff, CF14 5DX, UK), which were subsequently used as fiducial markers for alignment of the X-ray projections. Once loaded into capillaries, cells were cryo-preserved by plunging the tip of the specimen capillary into a ~90 K reservoir of liquid propane at 2 m $s^{-1}$ using a custom-made fast-freezing apparatus.

Soft X-ray tomographic data were acquired using the cryogenic soft X-ray microscope in the National Center for X-ray Tomography (NCXT) at the Advanced Light Source in Berkeley, Calif. The microscope and image acquisition have been described in detail previously (2, 3). Projection images were collected at 517 eV using a Fresnel zone plate with a resolution of ~50 nm as the objective lens. For each data set, 90 projection images were acquired spanning a range of 180°. During data acquisition, the specimen was kept in a stream of helium gas that had been cooled to liquid nitrogen temperatures to maintain cryo-preservation of the sample. Depending on the thickness of the specimen, exposure times for each projection image varied between 200 and 350 ms. 3-D reconstructions of the X-ray projections were calculated using the software package IMOD after manually tracking fiducial markers on adjacent images for alignment (4). AMIRA (FEI) was used to semi-automatically segment the 3-D volumetric reconstructions into subcellular compartments (lipid droplets, chloroplasts, starch, mitochondria) based on their different gray level ranges. Segmentation of the nucleus was performed manually.

DNA Preparation and Quality Assessment

Genomic DNA was prepared as follows. Total cellular DNA was extracted from cells grown in 1 L cultures to ~5×10$^6$ cells/mL. Harvested cells were resuspended in 300 µL Milli-Q purified water and 500 µL lysis buffer (100 mM Tris-HCl pH 8.0, 40 mM EDTA, 400 mM NaCl, 2% SDS) and incubated for 2 h at 65° C. while rotating. 170 µL of 5 M NaCl and 135 µL of 10% w/v CTAB in 700 mM NaCl were added. After incubation for 10 min, the DNA was extracted by adding phenol:chloroform, vigorously shaking, and centrifuging (~15,000 g for 5 min) to separate phases. The aqueous phase was removed and placed in a new tube with 5 µL of RNase A, incubated for 20 min at 37° C., and followed by two additional phenol:chloroform extractions and one chloroform extraction. To precipitate the DNA, 0.1× sample volume of 5 M NaCl and 0.7× sample volume of isopropanol were added to the resulting aqueous phase, the sample was mixed, and pelleted by centrifugation (15,000 g for 15 min at 4° C.). The supernatant was removed and pellet was washed with cold 70% ethanol, centrifuged (15,000 g for 5 min at 4° C.), and the supernatant removed. The DNA was cleaned with an ethanol precipitation step (100% ethanol, 100 mM sodium acetate pH 5, overnight at 20° C.), centrifuged (~15,000 g for 5 min at 4° C.), and followed by an ethanol wash. The DNA pellet was briefly air-dried and resuspended in Milli-Q purified water. DNA concentration and quality was assessed by optical absorbance on a Nano-Drop 2000 spectrophotometer (Thermo Scientific).

To obtain high molecular weight DNA (≈270 Kbp) for optical mapping, 1 L of cells were grown to ~5×10$^6$ cells/ml. The harvested cell pellet was washed twice with cold ethanol and resuspended in buffer (200 mM NaCl, 100 mM EDTA, 10 mM Tris, pH 7.2). An equal volume of 1% agarose was gently mixed with the cells and the cell-agarose suspension was aliquoted into plug molds and cooled (4° C. for ~60 min). The cell wall was digested by incubating the cell plugs in protoplasting solution (4% w/v hemicellulose, 2% w/v driselase, 1 M sorbitol, 5 mM sodium citrate, 240 mM EDTA pH 8.0, 10 mM 2-mercaptoethanol) overnight at 37° C. while shaking. To lyse the cells, the protoplasting solution was removed and the cell plugs were incubated in lysis solution (0.5 M EDTA pH 9.5, 1% w/v N-lauroylsarcosine, 5 mg/ml proteinase K) overnight at 50° C. The lysis solution was removed and the cell plugs placed in 0.5 M EDTA pH 9.5 and shipped to OpGen, Inc. for optical mapping using BamHI enzyme.

RNA Preparation and Quality Assessment

RNA was prepared as follows. Cells were washed with cold ethanol on dry ice and ethanol was removed by centrifugation (2,200 g for 3 min at 4° C.). To break cells open, cells were homogenized with lysing matrix D on dry ice for 2×60 s with the FastPrep-24 (6.0 m s$^{-1}$, MP Biomedicals). Buffer (50 mM Tris-HCl pH 8.0, 200 mM NaCl, 20 mM EDTA, 2% SDS, 1 mg/mL proteinase K) was added, samples were vortexed and incubated for 3 min at room temperature, and cell debris was pelleted by centrifugation (20,000 g for 3 min). One mL of sample was added to 10 mL of TRIzol in MaXtract HD tube and incubated for 3 min at room temperature. To extract RNA, 1/5 volume chloroform was added, samples were vigorously shaken, incubated for 5 min at room temperature, and phases were separated by centrifugation (800 g for 5 min at 22° C.) and decanting. Total RNA was precipitated by adding cold ethanol on the aqueous phase and purified using the miRNeasy mini kit (Qiagen). RNA was eluted with DEPC-treated water and cleaned with an ethanol precipitation step (100% ethanol, 85 mM sodium acetate pH 8.0), centrifugation (~15,000 g for 5 min at 4° C.), and ethanol washing. The pellet was briefly air-dried and resuspended in DEPC-treated water. RNA concentration and integrity was assessed by NanoDrop 2000 spectrophotometer (Thermo Scientific) and Agilent 2100 Bioanalyzer.

RNA-Seq

Total RNA was purified from each culture as described above. The rRNA was selectively depleted with the Ribo-Zero rRNA Removal Kit (Plant Leaf) according to the manufacturer's instructions (Illumina). The remaining RNA was converted into cDNA and made into sequence-ready libraries with the KAPA Stranded RNA-Seq Kit (Kapa Biosystems). The 14 de novo transcriptome RNA-Seq libraries were pooled and sequenced with 150+150 bp paired-end reads on two lanes of a HiSeq 2500 high-throughput sequencer according to manufacturer's instructions (Illumina). The 44 high light RNA-Seq libraries were combined into three pools and sequenced with 50 bp single-end reads on three lanes of a HiSeq 2500.

The resulting data was demultiplexed with in-house scripts. Adapter sequences were trimmed with Scythe (5) and aligned to the ChrZofV5 release of the *C. zofingiensis* genome with RNA STAR (6). Determination of counts per gene and transcript abundance in terms of fragments per Kbp of gene per million mapped fragments (FPKMs) were made with Cuffdiff (7). Further analyses and figures were generated with cummeRbund package in the R statistical computing environment (8). PCA was performed with plotPCA( ) from the R affy package (9). Two-fold differentially-expressed genes and regularized log$_2$-transformation were performed with the R DESeq2 package (10).

De Novo Transcriptome Conditions

Transcriptome material was derived from 100 mL cultures of cells (~4-9×10$^6$ cells/mL) from 14 different conditions: high light (400 µmol photons m$^{-2}$ s$^{-1}$), medium light (100 µmol photons m$^{-2}$ s$^{-1}$), low light (10 µmol photons m$^{-2}$ s$^{-1}$), glucose (20 mM), 48 h darkness, 4 h anaerobic, 4 h dark and anaerobic, 1 h without sulfur (Bristol's Medium without MgSO$_4$, UTEX Culture Collection of Algae), 1 h without nitrogen (Bristol's Medium without NaNO$_3$), 1 h without phosphorus (Bristol's Medium without K$_2$HPO$_4$, KH$_2$PO$_4$), 1 h without iron (Bristol's Medium), low oxidative stress (5 µM rose bengal, 0.5 h dark followed by 1 h 100 µmol photons m$^{-2}$ s$^{-1}$), high oxidative stress (5 µM rose bengal, 0.5 h dark followed by h 100 µmol photons m$^{-2}$ s$^{-1}$), and hydrogen peroxide oxidative stress (1 mM H$_2$O$_2$). Cells were collected by centrifugation (2,200 g for 5 min at 4° C.), the supernatant was discarded and the cell pellet was frozen in liquid nitrogen.

Changes in Gene Expression During Shift to High Light

The gene expression light intensity experiment from medium light (100 µmol photons m$^{-2}$ s$^{-1}$) to high light (400 µmol photons m$^{-2}$ s$^{-1}$) was conducted as follows. 1 L cell cultures were grown to log phase (~3.0×10$^6$ cells/mL) under medium light (100 µmol photons m$^{-2}$ s$^{-1}$). Cultures were mixed and divided into 75 mL cultures in sterile 250 mL beakers. After acclimating overnight, the light treatment cultures were moved from 100 µmol photons m$^{-2}$ s$^{-1}$ to 400 µmol photons m$^{-2}$ s$^{-1}$, while control cultures were maintained under 100 µmol photons m$^{-2}$ s$^{-1}$. Replicates (N=4) were collected at 0, 0.5, 1, 3, 6, and 12 h, harvested by centrifugation (200 g for 5 min at 4° C.), and frozen in liquid nitrogen. RNA was extracted, processed, and analyzed as described above.

Assembly Overview

Next-generation sequencing and associated software has made draft assemblies via short-read whole genome shotgun sequencing easy and relatively automatic. For eukaryotic organisms, these drafts are typically highly fragmentary by traditional standards of model organisms, with fragments often of size spanning only one to a few genes at a time. For *Chromochloris*, a chromosome-level assembly comparable to model organisms was aimed for, and initial drafts purely via automated short-read methods were only of "genespace" quality and did not meet the goal. Hence, additional data—a global optical restriction fragment map from OpGen, Inc. and long reads via Pacific Biosystems ("PacBio")—were collected. No software was found able to automatically incorporate this additional data well enough to meet the assembly goal; hence, extensive manual integration effort was expended to meet the goal starting from automated assemblies as a base.

Genomic and RNA-Seq Sequences

Two Illumina paired-end libraries—"S" with shorter and "L" with longer inserts—were prepared as described earlier for genomic (combined nuclear, chloroplast, and mitochondrion) sequencing, including Illumina inline controls and a small amount of Illumina PhiX. Each library was run as an entire single lane of a HiSeq 2000 V3 flowcell at the UCLA BSCRC Sequencing Core to obtain ~104M ("S") and ~66M ("L") paired end 100+100 nt reads with ~96% of pairs passing RTA PF=1 (PF=0 pairs were discarded). (Pacific Biosciences genomic reads are discussed later.)

Fourteen Illumina TruSeq paired-end RNA-Seq sub-libraries were prepared as described above. A single equimolar pool was run on both lanes of a HiSeq 2500 V1 rapid flowcell at the UCLA BSCRC Sequencing Core to obtain ~476M 151+151 nt read pairs with 7 nt TruSeq index reads with ~86% of pairs passing RTA PF=1 (PF=0 pairs were discarded). Demultiplexing for assembly by perfect match to expected 7-mers gave ~23M to ~34M read pairs per sub-library and ~397M (~97% of PF=1) read pairs total.

Analyses of reads, a multitude of in silico-targeted subsets of reads, and various fractions of reads (e.g., heads or tails of first or second ends) were made over many iterations, starting with exploratory preliminary analyses under minimal assumptions and proceeding toward final analyses as conclusions and partial results accumulated. Tools used included assemblers Ray (11), ABySS (12), and ALL-PATHS-LG (13, 14); aligners Bowtie (15), Bowtie2 (16), HISAT/HISAT2 (17), BLAST (18), BLAST+(19), LAST (20), LASTZ (21), BLAT (22), OpGen, Inc.'s MapSolver, BLASR (23), and Parasail (24); error correctors/double-sequenced end overlappers/adapter trimmers Proovread (25), SeqPrep (26), and Cutadapt (27); sequence analyzers Jellyfish (28), MUMmer (29), TRF (30), IRF (31), Repeat-Masker (32) with Repbase Update (33), and RepeatModeler (34); gene callers AUGUSTUS (35) and tRNAscan-SE (36); visualization/analysis tools Savant (37), IGB (38), IGV (39), Biomatters Limited's Geneious, and Circos (40); GUI automaton Keyboard Maestro of Stairways Software Pty Ltd.; standard UNIX text-processing tools as well as bioinformatic utilities such as SAMtools (41), DEXTRACTOR (42), HTSeq (43), and EMBOSS (44); databases of biological knowledge such as NCBI (45), Pfam (46), and Rfam (47); as well as custom one-off programs and scripts written in languages such as C++, Perl, Wolfram's Mathematica, and MathWorks's MATLAB. Some computations were carried out on the UCLA Hoffman2 computing cluster.

Insert Lengths, and Read Preparation/Composition

From preliminary and later assemblies, mode insert lengths exclusive of adapters were ≈156 nt for "S" and ≈370 nt for "L", with "S" fairly Gaussian with standard deviation ≈16 nt, but "L" bimodal with approximately one third in a wide mode at ≈200 nt and two thirds in a non-Gaussian narrower mode at ≈370 nt skewed longer. Inserts below 100 nt read into adapters (empirically verified to be as expected: for "S", first end A+TruSeq #6+dark/poly-A, second end reverse complement of TruSeq universal adapter+dark/poly-A; for "L", same except with TruSeq #12). Little of the "S" and "L" distributions is so short, and only ~150K (<~0.2%) of "S" and ~271K (<~0.5%) of "L" pairs contain ≥1 16-mer of consensus adapter ignoring dark/poly-A tails. Preliminary analyses often did not try to identify and remove adapters, while later analyses generally had them stripped via SeqPrep or Cutadapt.

Inserts below 200 nt have overlapping ends: almost all of the "S" distribution is as such, and a fraction of the shorter "L" mode is as well. Early analyses identified overlapped ends (merging double-sequencing to form consensus virtual single end reads) via unique overlaps of ≥16 nt with ≤3 mismatches; ~88% of "S" pairs and ~7% of "L" pairs were merged. The resulting pool of reads used for initial assemblies was then ~89M and ~5M virtual single end reads of total sizes ~14 Gnt and ~0.7 Gnt, and ~12M and ~59M read pairs of total sizes ~2 Gnt and ~12 Gnt, for a grand total of ~28.6 Gnt. Later analyses used SeqPrep for overlap detection and merging.

Rough composition is ≈1.3%/1.0% of "S"/"L" pairs as Illumina inline process controls (with ~95%/97% of pairs with ≥20% of 16-mers hitting a known control having ≥80% of 16-mers being hits) and ≈1.8%/2.9% as PhiX (with ~94%98% of pairs with ≥5% of 16-mers hitting de novo circular PhiX having ≥2/3 of 16-mers being hits), leaving ≈97%/96% for nuclear genome+chloroplast+mitochondrion. Once organelle genomes became available, ≈0.5%/0.7% and ≈0.2%/0.2% was estimated as chloroplast and mitochondrion, respectively.

With (1) coverage plentiful relative to the ≈58 Mbp assembly size estimate (see next section), (2) ≈70%/80% of "S"/"L" PhiX read pairs manifestly error-free, and (3) several dozen not unlikely corruption possibilities of comparable probability existing for a typical read (e.g., although PhiX errors concentrated as expected at the tails of reads, error position probability was substantial across more than 20 nt), it was decided to not generally perform spectral-based read "error correction" procedures on the Illumina reads. (However, correction of the Pacific Biosciences reads was critical for their use in refining the assembly.)

Nuclear Assembly Phases 1 and 2: Automated Base Assemblies

Histograms of the number of times distinct strand-collapsed (e.g., Jellyfish "canonical") k-mers appeared in the prepared Illumina read pool for various k suggested that potential diploidy was not a great concern, multi-copy repeats (although surely present) did not constitute an excessive fraction of the genome, and there were no large contaminants (e.g., bacterial genomes), suggestions later supported by data such as the ~58 Mbp optical size estimate and BLAST comparisons of final genome products against the universe of NCBI sequences. Plateaus visible in the cumulative plot provided one of the filterable signals by which the assembly of non-chromosomal sequences began.

The main automated draft assembly used in the first years of the project ("Phase 1") was an ABySS k=95 "gene-space" one on the prepared Illumina reads consisting of 3,513 scaffolds with longest ~407 Kbp, N50 ~79 Kbp, N90 ~19 Kbp, L50=217, and L90=754. This assembly guided further decisions (e.g., use of optical mapping and with BamHI) and was the point at which downstream analyses such as gene prediction began. Because Phase 1 contigs were slightly shorter than needed for high-likelihood automatic optical map placement, in Phase 2 additional assemblers were tried in an effort to find a slightly better automated base; a Ray k=51 "gene-space" one on the prepared Illumina reads consisting of 1,335 contigs with longest ~479 Kbp, N50 ~88 Kbp, N90 ~25 Kbp, L50=193, and L90=652 was chosen.

Nuclear Assembly Phase 3: Optical Map and Chromosome-Level Scaffolding, Joining, Filling OpGen, Inc. was contracted to construct an "optical map" of *Chromochloris* by imaging immobilized complete restriction digests of linearly-combed large molecular weight pieces ("hunks") of genomic DNA we provided. Based on Phase 1, they chose BamHI (G|GATCC) as digest enzyme due to the range of predicted fragment lengths being mostly accessible to their technology. They ran 12 high-density MapCards to obtain approximate fragment length fingerprints for ~318K hunks, which they assembled into 19 maptig chromosomes of total size ~58 Mbp whose constituents are not A/C/G/T nucleotide calls, but approximate fragment lengths under complete BamHI digestion (SI Files S6-S7). (As they omit all small maptigs, chloroplast and mitochondrion do not appear.) The final nuclear genome nucleotide sequences described in this work—the "ChrZofV5" version 5 release that Phase 4 (described later) ends with—adopt chromosome numbering and '+' strand decisions from this optical assembly.

During optical assembly, hunk fingerprints are piled up in multiple alignments with typical coverage of several dozens; chromosome ends are manifest as consensus locations beyond which hunk fingerprints do not extend (up to uncertainty in optically-estimated fragment lengths). OpGen observed both ends of all chromosomes except the right end of chromosome 5, the tail of which assembled into an approximate optical inverted repeat that, as discussed further later, likely is just the beginning of a much longer true sequence inverted repeat. (Due to this, the optical length of chromosome 5 is likely underestimated by ~0.56 Mbp and chromosome numbering does not reflect true size largest to smallest.)

OpGen's MapSolver software visualizes the optical map and aligns sequence contigs/scaffolds to it. (A degree of mismatch is allowed due to optical length uncertainty, the tendency of small fragments to be lost optically, and the possibility of small basecall sequence errors creating or deleting cutsites.) Experience suggests a contig/scaffold needs ≥5 interior fragments of non-small length (≥≈2 Kbp) for MapSolver to have a reasonable probability of placing it. This translates into a wide variety of contig/scaffold lengths due to *Chromochloris* BamHI fragment size variation, and Phase 1 scaffolds were often near this threshold with only ~12% covering ~37.6 Mbp being automatically placeable, even allowing non-unique placements and multiple coverage; the slightly longer contigs of Phase 2 improved to ~29% covering ~38.2 Mbp. However, by Phase 4's end with extensive hand work, ~93% of the optical map was uniquely covered (see main text FIG. 1) with just a single sequence scaffold per optical chromosome.

Most automated assemblers have as a design goal to be conservative, in that they would prefer to give a more fragmented result (which could be pasted together in an unknown way to get "truth") rather than one with mis-assemblies (in which some contigs/scaffolds would need to be taken apart before pasting could arrive at truth). Consistent with this, only a handful of Phase 1/2 scaffolds/contigs were found to be mis-assemblies via alignment to the optical map, increasing confidence that base sequence at finer resolution than the optical map was generally correct.

The per-chromosome single sequence scaffolds were formed from iterative rounds of optical placements of smaller subsequences (longer and longer as hand work proceeded), with the optical map providing global, externally-validated subsequence ordering and strand orientations and enabling approximate but accurately-sized N-filled gaps among subsequences and chromosome edges. Placements that resulted in overlapping or touching subsequences up to optical length uncertainty were, e.g., inspected at the sequence level for nucleotide overlap agreement of shorter lengths than automatic assemblers might otherwise require; reads and read pairs (including Pacific Biosystems long reads once Phase 4 began) touching and spanning gaps were isolated; and ambiguous placements could sometimes be resolved in favor of those not covering already well-covered parts of the optical map.

The optical map was useful: as hand work proceeded, speculative contig joins and extensions became reliable, as once further BamHI sites were reached, independent verification by the optical map was attained and possibilities were eliminated. Similar to the physical maps used in model organism projects, the optical map provided a global ground truth and acted as a ratchet for making positive progress that kept hand work from compounding mistakes. Each additional placement generally made other placements easier, as one could focus on gaps and not only were gaps getting fewer and smaller, but the pile of contigs, scaffolds, and reads to fill them with was also shrinking. Sources for speculation included: alignments of contigs and scaffolds to themselves; re-alignments of reads and read pairs to contigs and scaffolds; and, most importantly, the Pacific Biosciences long reads of Phase 4. Consensuses of supporting evidence spanning gaps was used to fill gaps; in some cases, these gap fills are of low quality (e.g., naked single-read PacBio sequence) but as long as the evidence supporting the join was substantial it was preferable to provide some representative sequence and close gaps rather than fret for first public release over every basepair being absolutely certain.

Nuclear Assembly Phase 4: Pacific Biosciences Reads, Contig Joining, and Gap Filling Numerous barriers in the draft assemblies evidently arose from the use of only short, paired end Illumina reads. Many difficulties were near repetitive sequence, either: (1) non-short segments of moderate/high entropy DNA that occur multiple times in the genome; or (2) low entropy DNA (e.g., microsatellites), these being trouble because of either (a) ambiguous continuations due to only having short reads, or (b) coverage collapse of multiple orders of magnitude (even so far as to completely deplete our nearly half-a-thousand-fold average coverage). Difficulties of type (2b) were common at points of very high G+C content as short as a dozen or two basepairs (as has been the authors' experience on other projects with the Illumina platform), and there appear to be many such loci in this genome (ChrZofV5 has 191 clusters of G+C runs of length ≥24 nt).

To overcome some of these obstacles and better scaffold subsequences, four 75 fps 3 h PacBio RS-II/Springfield 1.1 runs of genomic DNA with BluePippin selection were performed at the DNA Sequencing & Genotyping Center of the Delaware Biotechnology Institute to obtain long reads, but of relatively low quality. Each SMRT cell contained 163,482 ZMWs ("wells"). Of wells with ≥1 insert called by the PacBio basecaller, ~94% had only a single insert; hence, only a single longest interval per well was retained from the intersection of the "insert" and "HQ" regions, and no circular consensuses were made. The result was 149,364 "subreads" (from ~30% of wells) of 12 nt to ~34 Knt (median ~3.1 Knt) of total length ~692 Mbp.

Per-base error rates were estimated by the PacBio base-caller as very high compared to Illumina reads and as mostly indels rather than substitutions. No subread basecalls were given combined substitute/insert/delete/merge Phred qualities ≥15 (~3% chance of error or better), the mode was Phred 13 (~5% error), ~25% had Phred quality 0 to 7 (~20% to ~100% error), and the average chance of error per base was ~18%. Hence, pre-correction alignments of subreads to assemblies used PacBio-aware BLASR. While each default 12-mer seed only has ≈9% chance of being uncorrupted, queries ≥≈220 nt long have estimated chance ≥≈99% of ≥1 uncorrupted seed. Most BLASR parameters were left at defaults, but filtering was lowered to impose no minimum read/subread length and no percent identity requirement, and best alignments per query was raised to 250 internal and 100 emit as (1) the shortest target contigs were ≈200 bp and longest PacBio reads ≈50× longer; and (2) alignments descending into false positives were desired so that their statistics could be inferred from their great numbers.

From histograms of query and target alignment spans, a threshold of ≥140 nt was chosen for both spans to separate most true hits from very short false positives as well as short sequences repetitively occurring in *Chromochloris*, resulting in alignments. (Repetitive sequences of longer lengths remained; pre-alignment masking by tandem repeat finder TRF was sometimes used to help.) In subreads with ≥1 alignment, ~88%/~7%/~5% of PacBio bases on average participated in exactly one/zero/multiple alignments. For draft contigs participating in ≥1 alignment, mode coverage by PacBio bases was typically 8, with ≈0.1%/≈0.6%/≈97% of bases uncovered/covered exactly once/covered 2 to 23 times. PacBio reads did not show nearly as much coverage variation across sequence the Illumina platform found difficult (e.g., at runs of G+C's). The top alignment by BLASR score per subread was enriched for near-full length alignment span on the query. Once organelle genomes became available (discussed later), estimates put ≈0.1%/≈0.2% of aligning subreads as mitochondrion/chloroplast.

PacBio subread alignments were repeatedly used to help make assembly subsequence joins and to fill gaps as mentioned in Phase 3. A typical pass began by extrapolation of the unaligned ends of each aligned subread by the average compression/expansion ratio from indels in the aligned portions. Extrapolations might ("overhang") or might not extend beyond a subsequence's boundary, but overhangs of ≥1 Knt were not uncommon and, similar to earlier filtering, those of ≥140 nt were deemed "interesting". Based on histograms of distance of alignment starts and stops to subsequence edges for subreads with interesting overhangs, it was decided to consider alignment starts and stops within 9 bp of a subsequence's edge as having reached the edge. A subread alignment with an interesting overhang to a subsequence was considered "linkable" if it reached the same end of the subsequence (both ends for those with interesting overhangs on both ends). Subreads with a single linkable alignment on each end and to different subsequences on each end were declared "linking"; each of these suggests a merging of two subsequences with a particular relative distance and orientation with explicit sequence to fill any gap. Suggested merges from linking subreads were collected into a directed graph (that was typically enriched for linear paths) and evidence weighed at nodes with multiple incident arcs to determine if one arc had much more support (e.g., 6-fold more) than others, in which case only the dominant arc was retained and otherwise all arcs removed. The resulting directed graph of linear chains provides a round of up to a few hundred tentative assembly subsequence joins and gap fills to participate in the hand work process discussed in Phase 3. It was always satisfying to merge two or several subsequences into a subsequence large enough that optical placement became probable, and then finding the new subsequence had a unique optical placement that perfectly filled a hole in existing placements.

Using the pool of prepared but unassembled Illumina short reads as reference, the Proovread error corrector was also run on PacBio reads from three of the SMRT cells to obtain 83,069 polished trimmed reads of total length ~292 Mnt whose lengths were primarily between 500 nt and ~21 Knt (median ~3.0 Knt), with almost all bases explicit A/C/G/Ts (rare isolated Ns) and almost all per-base Phred-scale quality scores ≥19 (≈1 in 79 chance of error or better). These were very useful, as they enabled use of non-PacBio-aware tools (BLAST) to query and manipulate the long read dataset, and were used both in ways similar to the uncorrected reads (e.g., in procedures like the previous paragraph) as well as more targeted questions that arose once two subsequences were placed near each other on the optical map. (During operations such as subsequence joining, the larger pile of untrimmed corrected reads also produced by Proovread was queried as well; in certain cases, this was the only way to make progress and gap fill exposes naked single-read PacBio sequence.)

Periodically, and one last time at the end of Phase 4, prepared Illumina reads not aligning to the working assembly were re-de novo assembled to maintain an accurate pool of unplaced contigs/scaffolds. Only those of length ≥1 Kbp with less than one third of their 31-mers already represented were retained for the final chrUn##### unplaced contigs/scaffolds in the ChrZofV5 assembly release. To simplify naming, a few had a small number of Ns suffixed to make all their lengths unique.

Overall Structure of the Nuclear Genome

Telomeres.

As Phases 3 and 4 progressed and chromosome-level contigs/scaffolds approached optical ends of a chromosome, junctions with telomere repeats became apparent, and efforts were made (returning to Illumina and PacBio reads as necessary) to extend all sequences near such junctions at least partially beyond the junctions. As evident from chromosomes 1-4, 6-9, 13, 15, and 18-19 of the final ChrZofV5 assembly, the canonical *Chromochloris* telomeric repeat is apparently $(CCCTAAA)_n$ at 5'-ends of chromosome strands, and from chromosomes 1-3, 6, 8-11, 14-17, and 19 is $(TTTAGGG)_n$, the reverse complement, at 3'-ends. Examination of edges of assembly sequences from the algal genomes in Table 1 of the main text suggests *Coccomyxa* and *Chlorella* and possibly *Monoraphidium* are the same as *Chromochloris*, although *Chlamydomonas* appears to use $(CCCTAAAA)_n$ and $(TTTTAGGG)_n$. In *Chromochloris*, commonly observed non-canonical units are $(CCTAAAA)_n$ and $(CCCTGAA)_n$ near 5'-ends, and $(TTTTAGG)_n$ and $(TTCAGGG)_n$ near 3'-ends.

A prepared pool of Illumina reads was aligned with Bowtie2 in single end mode keeping top hit only to the ChrZofV5 assembly with PhiX; parameters were end-to-end "--sensitive" defaults, which allow short indels and up to ~10% mismatches. Total pool nucleotides aligning to nuclear components was ~26.8 Gnt, and the total size of pool members with ≥2 adjacent copies (not necessarily the same) of TAAACCC, TAAAACC, or TGAACCC or ≥2 adjacent copies (not necessarily the same) of AGGGTTT, AGGTTTT, or AGGGTTC was ~62 Mnt. As the nuclear genome is ≈57 Mbp, this suggests *Chromochloris* telomeres total ≈133 Kbp (≈3.5 Kbp/end).

The beginning (relative to nominal '+' strands) of chromosomes 5, 10-12, 14, and 16-17 and the end of chromosomes 4-5, 7, 12-13, and 18 were not reached in ChrZofV5. However, the presence of repeat units suggests that unplaced contigs chrUn97886, chrUn83064, chrUn12635, and chrUn01845 and possibly chrUn07087, chrUn06996, and chrUn06817 involve 5'-end telomeric junctions; and chrUn10942, chrUn10872, and chrUn03315 and possibly chrUn57207 involve 3'-end telomeric junctions.

Centromeres.

From experience with difficult sequence and gaps from Phases 3/4, candidate loci for centromeres (or, more likely, pericentromeric repetitive sequences surrounding them) were known for several chromosomes. For an unbiased scan, a visual examination was made of the whole genome distribution of each common TRF canonical tandem repeat unit. Focusing on units tending to concentrate in at most one zone per chromosome, iterative examination of sequence in and near these zones (by dotplots, BLASTing, local reassembly, and visualization of genome-wide occurrences) led to an expanding collection of putatively centromere-associated sequences; these were consistent with candidate locations. The collection converged on "ChrZofCen" (given later), a single circular ~4 Kbp Type 1/Copia LTR retrotransposon with ~0.7 Kbp spacer, together with TRF canonical units AAACATCTAG (SEQ ID NO: 22), AATCTGTGGTAGG (SEQ ID NO: 23), AAACATCTAGACACATCTAG (SEQ ID NO: 24), and AAACATCTAGACACATCTGG (SEQ ID NO: 25), with some 5S rDNA sequence.

TABLE S1

| Chrom. | Start ('+' strand, bp) | End ('+' strand, bp) | Nominal width (Kbp) | Comments |
|---|---|---|---|---|
| 1 | ≈3,418,656 | ≈3,457,392 | ≈39 | strong |
| 2 | 2,093,247 | 2,141,774 | 49 | strong, extra at 1,065,500-1,069,989 |
| 3 | 2,551,134 | 2,571,108 | 20 | strong |
| 4 | 2,648,641 | 2,651,949 | 3 | possibly 2,719,643-2,722,347 (with asm. gap after) or 937,962-943,022 |
| 5 | 1,034,650 | 1,047,659 | 13 | strong |
| 6 | 709,495 | 716,341 | 7 | strong, with assembly gap after |
| 7 | 2,360,779 | 2,420,790 | 60 | weak, with assembly gap inside |
| 8 | 639,124 | 644,655 | 6 | weak, with assembly gap after |
| 9 | in a gap | in a gap | ? | no good candidates even though no large assembly gaps on this chrom. |
| 10 | 860,629 | 862,963 | 2 | weak |
| 11 | 1,205,545 | 1,222,695 | 17 | strong, with assembly gap inside |
| 12 | 1,369,284 | 1,377,652 | 8 | strong, with assembly gap inside |
| 13 | 1,675,799 | 1,692,810 | 17 | weak, with assembly gap inside; chromosome has large assembly gap |
| 14 | 443,632 | 450,078 | 6 | possibly 736,796-739,088 (with assembly gap before) |
| 15 | 1,526,503 | 1,537,899 | 11 | strong, with assembly gap before |
| 16 | 490,261 | 510,147 | 20 | strong, extra at 772,237-776,289 |
| 17 | 1,793,652 or 126,717 | 1,796,217 or 127,771 | 3 or 1 | first option is at end of chrom., second with asm. gap after; 5 large asm. gaps |
| 18 | in a gap | in a gap | ? | no good candidates; chromosome has three large assembly gaps |
| 19 | 935,605 | 973,134 | 38 | weak, with assembly gap inside |

There are 39 unplaced contigs likely containing (peri)centromeric fragments:

chrUn{42003, 22516, 18154, 16591, 13058, 12366, 09183, 08437, 08040, 06312, 05306, 04914, 04275, 04018, 03492, 03384, 03059, 03028, 02729, 02724, 02655, 02649, 02593, 02484, 02398, 02352, 02284, 02246, 02034, 01939, 01933, 01883, 01678, 01641, 01499, 01429, 01415, 01238, 01183}.

ChrZofCen (with IUPAC ambiguous nucleotides and '{option₁, option₂, . . . }' curly braces capturing the most common variations observed) consists of the following coding portion (which, in all expansions, starts and ends on a codon boundary with ATG and TAA):

ATGACAGAACTGGAGAAGCTGGGTATCCCAArACTkAACGACCACAACTA

TGTCTTCTGGCACATCAAGATGCGAGCCTACCTyGTTGCAAGAGGATACA

GCGCAGCAATAACGAACGCAGAAGACGCCAACAGTGACAAGGCTCTTGCT

TCCATCACTTTGGCTGTGGAAGATCATTTTCTACCTACAGTrTACAAwGC

TGCAAGTGCGAAGGCAGCATGGGACGCGCTGGAGGCGTTGTTTCAGCAGC

GGAGCGTTGCCAACCAGCTGAACCTCACGCAGGAACTGAACAACCTCACA

CTGCAGCCTGGGGAGACCATCACACAGCTACTTGCTCGTGCCAGAATCAT

ATGGGAGCAGCTTAAGGCAGCTGGTATCGACAAGTCAGAGCAGGAGGTGG

CGTTATCAGTGTTGTCAGGACTTCCTGCCGACTTCAACACCTTAGTGACA

GTACTACAGAATCAGTCTGGTCCmCTyACyCTGrGTGGCATCCAGAAGGC

TGTCTTGACAGAACAGCAACGTGCAAATAAGGTTGGGGCATCAACGTCTA

CTGCAGCAAGCACCAAGGCTTTCTACACTCAGAACGGTCCCAACCrTGGC

ArGCTTGGTGACAGCGGTACCAGGACCAGCAACTT{, CAACCAGGGGAAC rG}CAACACCAAGCAGCAGGAGCAGCGTAAGTGCTACTACTGTGGCAAGA

AGGGGCACCTGAAAAGGGACTGCAGAAAGAAGAAGGCAGACGAGCAGCGT

GGCCCCAGTACCAAGGCTTCAACAACAATGGCATGGACTGCAGCCTGCAA

CACCAGCATCAGCCTCAGCTCAGGTACCTGGGTCCTCGACTCTGGAGCAT

CAAGACACGTCTGCAAAGAACGCAGCCTGATGCAGAACCTGCAACAGCTG

AACCAGCCAGTCTACATCACGTACGGCAACGGTAGCACAGGGGTGGCACA

GACTATGGGGAGGTTGTTCTCAACGACAGGATCCGTCTACGGAACGTTT

TGTTTGATCCCACTGCTGTTGGCAATCTCCTTTCCATCCsTACAGCAGCT

GCryGTGGAGCACAGTTTAACTTTGsAGCCArTTGCTGCACCATTCGAGT

AAATGGCAGACTGGTGGCAATAGCACAGCAGCAwGAyGGTCACTAyTGCT

TGCACTCTGAGCAwrCAsAGTCAGCCACTGCACTGGCAGCCCAGACCCCG

CAGCTGTGGCATCGTCGTTTTGGCCATCTCAGCTACCAGAATATGGCCAA

GGTCCCCAACTTGGTAACGGGCGTCCAAGTsCCAACTGArGCCTTTCAGG

CAGCAGGTCAGCAGGTGTGTGAGCCATGTCTACTkGGCAAACAGACACGA

-continued

CTGTCTTTCCCCGAGTCAGArACTGTCAGGCAGCAGyCACTkGArCTGGT

GCATATGGACCTCTGTGGACCTCTyCCTGTCAAGTCACTTGGAGGCAGCC

AGTACATTGCTACGTTCCTGGAyGACTAyACAGGACTGTCAGTrGTGGCA

TTGCTCAAACAGAAGTCAGACATTTCyAArGTTGTGCCTGACGTCTTCAA

CATGCTAGAGAAACAGAGCAACAATCAGGTGAAGGGCGTCCGCACTGACA

ACGGCGGGGAGTATGTCAACAATGTGmTGAACAGCTACTACAGCAGCAAG

GGCATCATCGCACAGCACACAGTACCATACAGTCCTCAGCAGAATGGCAA

GGCAGAAAGACTCAACCGAACCCTACTGGACAAGGCACGTTCCATGCTGG

CAGATGCArGGCTACCTTCTCAGCTrTGGGGTGAGGCCGTGGTAACAGCC

AATTATCTTAGGAACCGTTCACCAGCAGCTGGCAAGACAGCAACACCCTG

GGAACTGTTTTTGGGTCACGGCCCTCTGTCTCTCATCTTCGCGTGTTTG

GGGCCAAGGCGTTTGCACAGATCCCCAAGGAGAAACGTGGCAAGCTGAC

CCAAGGAGTCAGCGTGGCATCATGGTTGGATATGAGCCyAATGTAAAGGG

GTACCGTCTACTGCTTCCAAACAACACCATCACAGTCAGCCGGGACGTTG

TATTTGATGAAGGTGACCAGCCAGGAGCArTAGACACCAACTTCTATCCA

GACTTGGAAGATGAGCTTGATGTTACTGCAGCCATCAACACTGGATCTAA

TGCAGCACCTTCTGTCAATACTTCTGGAACAGCTGAGCCACCACCATCAG

TTGCAGCACCCGTCGACCCACCAATTTCGGCACAGACCATGGAAAACGTG

GGAGCCAGCAACAGCTCAACACCACAAGGCAGyGAGGAAGATCAGCATCA

GCAATCACGTAGAAGTAGCCGGGCCAACATTGGCATGGCACCAGGCAACT

ACTGGGAGGCCAACTACATTCCCACATCCAAGCGTACAGCTACCGGACTG

TTGGCACAGACATCAGAAATTGTTGAGCCAGCAACCTATGAmGAAGCACT

ACAGTCAGACTGTGCAGAGCAGTGGCAGCAAGCCATGGACAGCGAGTACG

CATCGCTGATAGCCAATGGAACTTGGACCTTGGAAAAACCCCCAACAGAC

ATTAGGCCCATCCCTGTCAAGTGGGTGTATAAGGTGAAACGTGACACCAG

CGGGAACATTGAGCGGTTCAAGGCACGCCTGGTGGCCAAGGGTTTTTGGC

AACAGGAAGGTGTGGATTATGACGAAGTGTTCGCCCCGGTAAGCAAGTAT

GCTACCTTTCGGGCACTAATGGCCAAGGCAGCAGAAGAGGACATGGAACT

ACACAAATTGGATGTCAAGACTGCGTTCCTTCAAGGCAACCTGGAAGAAG

ATGTTTGGATCCAGCAGCCTCGTGGCTACGAGGArGGCAGCAGTGAACTm

GCCTGTCATCTwCAyAAACCTTTGTACGGGCTCAAGCAGGCyCCTCGrGC wTGGCATCAGCGGCTACAACAGGAACTACTGGCAGTAGGCTACACAGCAT

CAGCAGCAGACCCCAGCCTGTACTGGTACTGCATCAACGGGACTATGTG

TACCTCCTGGTCTAyGTGGATGATATCCTGATTGCAGCCAAGCAGCTTGA

GTCAGTCAAGGCAGTCAAGCAGCAGCTrTTAGGCTTATTTGAGTCGCGTG

ACCTTGGAGAAGCwACATCCTACCTTGGTATGAGCATTCAGCGCAACAGA

CAGACAGGCAyCATCAAGATyGGGCACCGACTCATGATCACAGAGTTACT

GGArArGTATGGyGCAGTmGACAGCAAAAThAAGTCArTACCACTGTCTC

CATCTATCAArCTrGCyAAAGATGAAGGCGryCCCCTAGACAAGGAACAT

TACCCTTACAGCCAACTGGTTGGGAGTCTCATGTACCTTGCAATCACCTC

-continued

CAGGCCAGACCTCGCCTTTTCTGTGGGGGCTCTTGCACGCTACATGTCAT

GCCCAACCACwGTCCAyTGGCArGCAGCTAAGGGrGTrCTACGCTACTTG

GGAGGAACCCTGGACTATGGCATCACCTTTGGTAGCGACAGCAATGACCT

CATTGGCTACTGTGACGCAGACTATGCGGGAGACACAGACACACGCAAGT

CCACCAGTGGCTACATATTCATACTGCACGGAGGGGCCATyACkTGGAGT

AGTAAGCGCCAGGCAACAGTTGCAGCmTCAACCACGGAGGCTGAGTACAT

GGCAGCAGCAGCAGCAGTCAAGGAAGCTCTATGGCTGCGTACACTCTTGA

GCGAGCTGCAGCTAGACATAGACAACATCACTATCATGGCAGACAACCAG

TCAGCAATCAAGCTTCTGCGCAATCCTATCTCATCCATGAGAACCAAGCA

CATTGAyGTGGCTTATCACTTTGCTAGGGAACGCGTGGTGCGCAAGGAGG

TTGTGTTCAGGTTCGTTTCCACAGAGAACATGGTGGCAGACATCATGACC

AAGGCTCTGAGCGAAGTCAAGCATGTGCGATGTTGCAAGGGCATGGGGGT

TGGAGTTTAA
(SEQ ID NOS: 26-27)

followed by a more variable spacer region

AGAAACTTGAAATGCGTGGGAGCATCTTTGACAGTACATGCCTGACTGC

GTGGGAGTGTTGAAATACGGCCTTTATTCAGTCAGACCTGCACTGCCAG

AATCCAGAAGTTGAGCATCTTTGACAGTACATGCCTGACTGCGTGGGAG

TGTTGAAATACGGCCTTTATTCAGTCAGACCTGCACTGCCAGAATCCAG

AAGTTTCCAGATGGTTCTGGAAGyCCCCAGATGTTTCyAGATGTTTCyA rATGTkTCy{,AAATGTGTCC}{,AGAAGTTTCTAGAGGTGTCTAGATG

TTTCT}AGAATATTGGTGCATGACACGTGTCAGTCACTTTGTGGTr{,G

TAGGAATCTGTG,GTAGGAATCTGTGGTAGGAATCTGTG}GTAGGAATC

TGTGGTAGGAATCTGTGGTAGGAATCTGTGGTAGGATTCCCAGTAGGTG

AACACAGTTGCCAGTGGATTGCCATTGTGTCGTGAGTATATAAAGACAC

AGACTTGTCCCAATCTGTAAyAyTGTCCAGCCCGAGysCCACCGAGGCC

CCACGCTTAAACACAGACCGCAACACAGAGCTGAGGATACTGAGTCGCT

AGAACGACTwAGrCAACAGATTTCCATCAGGTTATGGGCCCACrCCCAC

ACGCACAATCGCTGTGCTGCTCAGAAATTTGTTGTGTTCGGCCATAAGT

GTTGTGTACAGTTCGTCArCmAGGTCACd
(SEQ ID NOS: 28-39 which then circles back to the beginning of the coding region. The Type 1/Copia LTR retro-transposal nature is clear from NCBI web conserved domain hits to its amino acid translation, these being DUF4219 (a domain associated with the N-terminus of gag-pol proteins), UBN2 (gag of LTR Copia type), ZnF_C2HC/zf-CCHC (zinc knuckle associated with retroviral gag), gag_pre-integrs (part of gag lying just upstream of integrase), rye (the integrase core domain), RVT_2 (reverse transcriptase), and RNase_HI_RT_Tyl (RNase H for Type I/Copia LTR retroelements), in that order. NCBI web BLASTX had best hit to filamentous green alga *Klebsormidium flaccidum* with second best organism being colonial green alga *Volvox carteri*.

Due to the difficulty of assembling such large-unit repetitive sequence occurring in multiple tandem arrays (and reads suggest each array consists of complex nested insertions of mixed orientation with some divergence), ChrZofV5 in (peri)centromeres—even when given as gapless pure A/C/G/is—may have considerable errors. Almost all putative (peri)centromeric intervals given in the table on the previous page are associated with major assembly gaps and/or fine size differences between in silico BamHI fragment lengths and the optical map (with the assembly generally being too small; see also the discussion later about known assembly problems). However, borders and entry into pericentromeric sequences should be of quality comparable to the assembly generically, the optical map prevents massive errors (and constrains sizes), and sequence presently in ChrZofV5 should be representative. An estimate of the total size of (peri)centromeres was obtained in two ways. First, there is ≈195 Kbp of N-free sequence in the called intervals of the table and ≈231 Kbp of N-free sequence in the identified unplaced contigs/scaffolds (although all of such may not belong, as edges may be ordinary nuclear sequence), a total of ≈426 Kbp. Second, an analysis similar to that using Bowtie2 for the telomeric sequences (except selecting prepared Illumina reads as those having at least one 19-mer hit to either strand of all IUPAC-ambiguity and curly brace expansions of ChrZofCen or any rotation of (AAACATCTAG)$_2$ (SEQ ID NO: 22), (AATCTGTGGTAGG)$_2$ (SEQ ID NO:23), AAACATCTAGACACATCTAG (SEQ ID NO:24), or AAACATCTAGACACATCTGG (SEQ ID NO: 25)) finds ≈290 Mnt of (peri)centromeric reads vs. the ~26.8 Gnt of nuclear reads, suggesting total centromeric nuclear sequence of ≈618 Kbp. Thus, *Chromochloris* may have a total of ≈0.5 Mbp of (peri)centromere, an average of ≈25 Kbp per chromosome.

Ribosomal DNA (rDNA).

The canonical rDNA repeat unit for *Chromochloris* became apparent early in assembly during analysis of k-mers observed with high frequency, and is given as contig chrRr. It assembled as a 9,702 bp circular consensus which RNAmmer (8) annotates as follows (the consensus was oriented so that annotations fall on the '+' strand, and the de-circularizing linearization cut was placed just before the 28S rRNA annotation):

Typically, rDNA exists in at least one large tandem array; such sequence is, however, difficult to assemble. As with the (peri)centromeres, bordering sequence and entry into such regions is expected to be less problematic. From the plot, the tail of chromosome 13 (relative to its '+' strand) leads into a large assembly gap with rDNA sequence at the left border (indicated by purple oval). Further, the rDNA consensus contains two BamHI sites which, in circular form, produce fragments of sizes ~6.0 Kbp and ~3.7 Kbp that are both in the range in which the optical mapping worked well, and this region of chromosome 13 has an optical tandem repeat of copies of an alternation of fragments ≈6 Kbp and ≈4 Kbp in size. This suggests that the large assembly gap at the end of chromosome 13, estimated to be ≈593 Kbp in size, begins with ≈24× copies of the rDNA unit (likely with divergence among copies); these copies would represent ≈233 Kbp or ≈40% of the gap. Various analyses (e.g., that of Table 1 in the main text) assume this gap begins with 24× exact copies of chrRr.

Repetitive Sequence.

There are repetitive sequences beyond the telomeres, (peri)centromeres, and rDNA already discussed. The nuclear fraction of the ChrZofV5 assembly was analyzed with RepeatMasker 4.0.6open (using slow search and gccalc options with engine RMBlast+ 2.2.28) in combination with all of Repbase Update 2016-08-29 ("eukaryota") and de novo identified repeats from RepeatModeler 1.0.8open with RepeatScout 1.0.5, RECON 1.08, TRF 4.04, and RMBlast+ 2.2.28 (SI File S8). About 6% of the assembly (excluding N-runs) was masked, mostly in interspersed repeats (~5.0% of sequence) as primarily LINEs (~2.0%), LTRs (~1.5%), unclassified elements (~1.2%), and DNA elements (~0.4%). The remainder was mostly simple repeats (~1.0%), with some satellites, low complexity sequence, and small RNA (total ~0.1%).

Per chromosome plots of repeat and gene density were prepared. Gene density is rather uniform, and there are no grand scale gradients in genes or repeats as found in, e.g., *Arabidopsis*, a genome approximately twice as large that has megabasepairs of pericentromeric heterochromatin (49). Some smaller scale gradients in repeats are found near (peri)centromeres and especially large assembly gaps (e.g., the large gaps of chromosomes 17 and 18). There are a few localized concentrations of particular kinds of repeats. As apparent from Table 1 of the main text, *Chromochloris*, like *Coccomyxa*, has relatively few repeats compared to other algal genomes of comparable size (*Chlorella* or *Monoraphidium*) and much fewer than larger genomes (*Chlamydomonas* or *Arabidopsis*).

Known Assembly Issues.

From the hand word and detailed comparison of the final ChrZofV5 assembly to the optical map, 100 areas where the assembly has issues are known. (These are in addition to a likely number of very localized errors, e.g., individual basepairs; assembly polishing by variant detection using re-aligned reads is pending for the next assembly release.) About half of issues (52/100) are represented in the ChrZofV5 assembly by runs of one or more N bases (typically with length a multiple of 1,000 bp sized approximately correct via the optical map); another half (47/100) are deviations in number of BamHI fragments or fragment lengths between the assembled sequence and optical map beyond norms; and a final one (1/100) is the optically-troubled tail of chromosome 5 mentioned earlier. Issues are detailed in SI File S4 and summarized in SI File S5. Below is a brief discussion of the summary and largest issues.

The largest assembly gaps (≥≈100 Kbp) are: one in the interior of chr. 4 (issue V5.04.4) of ≈193 Kbp; one at the beginning of chr. 11 (V5.11.1) of ≈107 Kbp; one at the end of chr. 13 (V5.13.6) of ≈593 Kbp of which, as already discussed, the first ≈220 Kbp of which is likely copies of the rDNA repeat unit (so the amount missing is more like ≈373 Kbp); one in the interior of chr. 14 (V5.14.2) of ≈128 Kbp; three in the interior of chr. 17 (V5.17.2, 0.4, and 0.6) of ≈120, ≈295, and ≈138 Kbp; and two in the interior of chr. 18 (V5.18.1 and 0.2) of ≈248 and ≈208 Kbp. Chromosomes 17, 18, and 13 have by far the most assembly gap as a proportion of optical length. The presented sequence of chromosomes 1, 2, 3, and 9 is gapless, although, as discussed earlier under, e.g., centromeres, this does not imply they are perfect. Much of the "missing" sequence is expected to be among the unplaced contigs/scaffolds.

OpGen did not observe the right end of chromosome 5 (issue V5.05.10); its map ends in an inverted optical repeat of ≈150 Kbp per arm. From patterns of chromosomal coverage by reads and detailed hand examination of Illumina and PacBio reads aligning and partially aligning in this region, it was determined after the ChrZofV5 assembly was frozen and this publication was initially submitted that the likely resolution is this inverted repeat is much larger—fully ~564 Kbp per arm—with the right arm exiting directly into telomere repeats. Using 1-based inclusive-inclusive '+' strand coordinates in ChrZofV5, a full left arm is given as chr05:3230407-3794116 and a full spacer between the two arms is given as chr05:3794117-3795139, but the end chr05:

3795140-3801251 only gives ~6 Kbp of a right arm (and with chr05:3796510-3798042 being naked single-read PacBio sequence). A quick patch is to tack revComp(chr05: 3230407-3788934): AAGGGTTTAGGGTTTAGGGTT-TAGGGTTTAGGGTTTAGG GTTTAGGGTTTAGGGTT-TAGGGTTTAGGGTTTAGG (SEQ ID NO:40) onto the end of ChrZofV5 chr05, making chr05 longer by 558,602 bp, but it is planned for the next genome release to use the PacBio reads to phase the two arms (which appear to have some variation) and give a better representation (as the sequence currently in ChrZofV5 is presumably randomly phased). Note there are 155 current gene models affected (Cz05g32080, . . . , Cz05g37220 in the left arm and Cz05g37230 and Cz05g37240 in the right); there will be another ~153 once the rest of the right arm is added. Except for this paragraph, this disclosure assumes a genome with most of the right arm absent.

ChrZofV5 chromosomes 1 to 19 total 57,719,290 bp (including N placeholders); the optical map totals 57,763, 775 bp (with only the first half of the chromosome 5 optical repeat counted). These agree to ≈1 part per thousand and, when quoting lengths as fractions of the nuclear genome, it does not matter much which is taken as reference whole. (The total differs by under 45 Kbp and single chromosomes by under ±42 Kbp.) About 5% of total (≈3 Mbp) is missing over the 52 runs of Ns; the unplaced contigs/scaffolds presumably provide ≈2.4 Mbp of this (≈80%). Over the 47 BamHI fragment disagreement issues, assembled sequences are estimated to be missing ≈512 Kbp and have ≈45 Kbp extra; this is under 1% of total and a smaller class of problem than the runs of Ns. Thus, ≈6% of total is missing or otherwise troubled, but ≈94% is placed and in tight agreement with the optical map. Although current data is not exhausted and additional refinements can be made, in the interest of timely availability to the community of the already high quality genome, the ChrZofV5 version is being publically released.

Genomes of the Chloroplast and Mitochondrion

Assemblies of organelles took place between nuclear assembly phases and also required multiple hand-managed passes (as they were not assembled whole by any of the automatic processes). Various methods were used to identify potentially relevant contigs and reads, including relatively high coverage, low G+C content, alignments and synteny to existing NCBI chloroplast and mitochondrion sequences, and alignments to seed contigs once some were in hand.

Mitochondrion.

The mitochondrion (for SAG 211-14, the strain of this study) was completely assembled as a single circular 41,733 bp contig chrMt with no IUPAC ambiguous nucleotides; the strand orientation and linearizing cut were chosen to agree with NCBI accession KJ806268.1, the 44,840 bp complete mitochondrion of Chromochloris zofingiensis strain UTEX 56. Annotation of protein-coding genes, tRNAs, and rRNAs of chrMt was by BLASTN/BLASTX and BLASTP to the NCBI 'nt' and 'nr' databases, tRNAscan-SE, RNAmmer, Rfam, syntenic alignments to closely related known sequences (e.g., to KJ806268.1), and visual examination of RNA-Seq alignments (which suggest some UTRs, although these were not kept in the final annotations). The overall structure of chrMt is highly similar to KJ806268.1, having the same major protein-coding genes, tRNAs, and rRNAs in the same order, however there is considerable divergence at the nucleotide level with a global pairwise alignment (Geneious 93% similarity cost matrix, gap open penalty 30, gap extension penalty 1; only ~66% identical. Divergence is concentrated intergenically and the splicing structure of rrnL4 is different. Globally aligning just the coding sequences results in ~98% nucleotide identity. Translating the coding sequences via NCBI genetic code #22 (the Scenedesmus obliquus Mitochondrial Code) and globally aligning (Geneious BLOSUM62, gap open penalty 12, gap extension penalty 3) estimates ~99% amino acid identity.

Chloroplast.

Similarly, the chloroplast (for strain SAG 211-14) was completely assembled as a single circular 181,058 bp contig chrCp, also with no IUPAC ambiguous nucleotides; the strand orientation and linearizing cut were chosen to be in agreement with NCBI accession KT199251.1, the 188,935 bp complete chloroplast of C. zofingiensis strain UTEX 56. Again, annotation of protein-coding genes, tRNAs, and rRNAs was by BLASTN/BLASTX and BLASTP to NCBI 'nt'/'nr', tRNAscan-SE, RNAmmer, Rfam, syntenic alignments to closely related known sequences, and visual examination of RNA-Seq alignments (which again suggested some UTRs, although as before these were not kept in the final annotations). As with many chloroplast genomes, there is a large rRNA-related inverted repeat (~6.7 Kbp in SAG 211-14, ~6.4 Kbp in UTEX 56) separating two single copy regions. It is difficult to resolve the arms with short reads; they assembled as identical except for a tandem repeat CTTGGTATTGGGGC (SEQ ID NO: 41) estimated as 8× in the first arm and 9× in the second (where SAG 211-14 inserts ≈300 bp relative to UTEX 56). The relative strand orientation of the single copy regions is ambiguous, and no PacBio reads were found able to resolve this. The single copy regions were assembled in opposite relative strand orientation compared to KT199251.1, and so in further comparisons the second single copy region of KT199251.1 was reverse complemented.

With the second single copy region of KT199251.1 reverse complemented, the overall structure of chrCp is highly similar to KT199251.1, with the major protein-coding genes, tRNAs, and rRNAs again in the same order. Aligning in the same way as with the mitochondrial genomes, global alignment gives overall nucleotide identity of ~83% and global alignment after restriction to coding sequences gives ~98%; divergence is again concentrated intergenically. The largest difference is the loss in SAG 211-14 of almost all of a ~9.3 Kbp region in UTEX 56 annotated as containing a ptz-like ORF. Translating the coding sequences via NCBI genetic code #11 (the Bacterial, Archaeal, and Plant Plastid Code) and globally aligning results in ~97% amino acid identity, with lower percent identity in the larger genes (e.g., ftsH, rpoC2, and ycf1). The gene psaA remains trans-spliced (with RNA-Seq in concurrence); an in silico effort to identify a homolog of the Chlamydomonas tscA gene involved in this process was unsuccessful.

From the Bowtie2-based analysis introduced in the telomere discussion earlier, coverage on chrMt and chrCp from prepared Illumina reads is ≈1,280× (≈0.2% of sequencing effort) and ≈890× (≈0.6%), respectively. Coverage of PhiX is ≈150,000× (≈2.8%), and the nuclear genome (chromosomes, rDNA, and unplaceds) is ≈460× on average (293.9%). The remaining ≈2.6% of effort is in reads that did not align; ≈1.5% is accounted for in a re-alignment to Illumina inline controls, leaving ≈1.1% of effort unaligned. At nuclear coverage, this could be ≈0.7 Mbp of additional sequence, very close to the ≈0.6 Mbp more expected beyond current unplaced contigs/scaffolds as discussed under "Known assembly issues" above. The high fraction (≈98.9%) of original reads accounted for is encouraging;

there is not much sequence missing from the ChrZofV5 assembly, even if it is not yet in perfectly contiguous form.

Transcriptome Assembly Used in Training AUGUSTUS

To assist with training the AUGUSTUS ab initio gene modeler for *Chromochloris*, a draft transcriptome was de novo assembled from the 151+151 nt pool of ~397M read pairs from the fourteen RNA-Seq sub-libraries described earlier, using the Ray assembler with k=51. Such de novo transcriptome contigs are generally presented in random strand and codon frame, generally contain UTRs, and may contain introns (and many of large number of shorter, lower-coverage contigs may be wholly introns, and introns may change codon frame). To bootstrap AUGUSTUS, PASA 2.0.2 was used to extract a training set of genes (50).

Details of Main Text Table 1

Nuclear Genomes.

Sequences and annotations (especially those of model organisms) are often updated after initial publication, and details of definitions and statistical analyses can often greatly affect summaries. For these reasons, Table 1 was completed by analyzing freshly-downloaded current copies of reference genome sequences and gene models and uniformly applying the same criteria and methods to every organism rather than, e.g., copying nominal quantities from existing publications. Sources of nuclear genomes and annotations were TAIR10 for *Arabidopsis thaliana* ("AraTha"), JGI Phytozome 5.5 for *Chlamydomonas reinhardtii* ("ChlRei"), ChrZofV5 of this work (with 24× copies of the rDNA unit) for *Chromochloris zofingiensis* ("ChrZof"), JGI Phytozome 2.0 for *Coccomyxa subellipsoidea* C-169 ("CocSub"), JGI release 2014-08-18 with 'best genes' for *Chlorella* sp. NC64A ("Chlore"), and NCBI accessions KK100223.1-KK106940.1 for *Monoraphidium neglectum* ("MonNeg").

Sequenced Genome Size:

number of non-N/n bases in assembly (other IUPAC ambiguities were retained), rounded to nearest Mbp. Sequenced genome presentation: a "scaffold" is defined as a nucleotide sequence having at least one N/n (with other IUPAC ambiguities being irrelevant) and presuming every other sequence to be a "contig". For CocSub, all sequences are called "scaffolds" in distributed files and chromosome vs. arm vs. unplaced is not indicated; however, the distinctions are clear from presence of telomere-associated repeats at one, both, or neither sequence edge, and the number of chromosomes plus half the number of arms as thus determined equals the stated 20 chromosomes in the associated genome paper (51), which also mentions that, via Southerns, the pairing of half the arms was determined. Genome project primary initial strategy, average basepair coverage at earliest stage: per best evidence available and literature, including CocSub (51), AraTha (49), ChlRei (52), Chlore (53), and MonNeg (54).

Scaffold N50 (Taking Genome Size as Sum of Scaffolds as-are):

ordering scaffolds by decreasing size (and keeping all IUPAC ambiguous nucleotides), take scaffolds until total size is at least as large as half total size of all scaffolds, and report size of the smallest taken scaffold after rounding to the nearest Kbp. This was not performed for assemblies at chromosome/arm scale, as this quantity is then essentially as large as it can be and is controlled by the organism's distribution of chromosome sizes and is no longer connected to assembly quality. Contig N50 (taking genome size as sum of contigs as-are): form "contigs" by splitting scaffolds at every N/n (tolerating other IUPAC ambiguities) and removing all N/ns; order contigs by decreasing size, take contigs until total size is at least as large as half total size of all contigs, and report size of the smallest taken contig after rounding to the nearest Kbp. Number of chromosomes: per best evidence available and literature. For Chlore, although not mentioned in the associated genome publication (53), the largest scaffolds are large and one can look for telomere-associated repeats; 11 of their scaffolds begin with such a repeat and 7 end with one (and none have both ends thus associated), which is more or less consistent with the genome publication's determination of 12 chromosomes by Pulsed-Field Gel Electrophoresis (PFGE), with chr. 12 being difficult.

Protein-coding genes are taken as those directly declared as such by the annotations; in cases (MonNeg) without a direct indication, a GFF file gene was taken as protein-coding if and only if it had non-empty intersection with at least one GFF file CDS interval. Three of the releases here (for ChrZof, MonNeg, and CocSub) do not provide multiple transcript models per gene locus. (Although the CocSub release includes versions of files named so as to distinguish all models vs. "primary transcript only", such versions are the same and no protein-coding locus is actually modeled with multiple isoforms.) For AraTha, when desired, the canonical transcript model for each gene locus is per TAIR's file TAIR10_representative_gene_models.gz. For ChlRei, when desired, the canonical model is that marked longest=1 in the annotation GFF files (and all GFF files in the release agree on this designation). For Chlore, there is no issue since the only gene models used in this work are those from the release's 'best genes' files. Note that MonNeg is a highly fragmented assembly and one may expect (in agreement with the BUSCO analysis of main text FIG. 2B) its gene models to suffer due to, e.g., true coding sequences often reaching edges of assembly sequences; for this reason, numerous of its gene-related summary statistics may be more divergent from "truth" than for the other organisms.

Percent G+C in Sequenced Genome:

using only A/C/G/i nucleotides (no IUPAC ambiguities) in an all-uppercase version of the assembly, report fraction (#C+G)/(#A+C+G+T) as a percent, rounded to the nearest integer. Basepairs called as coding (in any transcript model) in sequenced genome: over all transcript models of all protein-coding genes, take union of coding sequence bases (ignoring strands) to get a target subset of assembly basepairs; restrict to the N/n-free fraction of this subset and the whole assembly (other IUPAC ambiguities being tolerated), and report percentage of the whole in the subset after rounding to the nearest integer. Percent G+C in basepairs called as coding (in any transcript model): over all transcript models of all protein-coding genes, take union of coding sequence bases (ignoring strands) to get a target subset of assembly basepairs; using only A/C/G/i bases (no IUPAC ambiguities) in an all-uppercase version, report fraction (#C+G)/(#A+C+G+T) as a percent, rounded to the nearest integer. Number of "complete" called protein-coding gene loci (collapsing transcripts): same as the row "Number of called protein-coding gene loci (collapsing transcript forms)" except restricted to coding sequences that satisfy all of the following: (1) are pure A/C/G/i (i.e., contain no IUPAC ambiguities); (2) have length a multiple of three nucleotides; (3) start with ATG; (4) end with TAA/TAG/TGA; and (5) do not contain an internal TAA/TAG/TGA codon.

Number of rDNA Units Estimated to Exist in True Monoploid Genome:

MonNeg and AraTha are via (54) and (55); for ChrZof, this work as, e.g., already described in subsection Ribosomal DNA (rDNA). For ChlRei, the original genome paper (52) contains some information but not quantitation. Seven paired-end 76+76 nt Illumina GA-II lanes of a *Chlamydomonas* genomic library were available from an unrelated project. Extremely high coverage 39-mers from the reads were de novo assembled, rDNA-related seed contigs selected via NCBI web BLASTN, paired-end reads having at least one 31-mer from the seed contigs and seen multiple times were extracted and re-de novo assembled to obtain a 6,543 bp consensus chunk of a presumed *Chlamydomonas* rDNA unit. The chunk contains a whole 18S followed by a whole 28S. Comparison of median Jellyfish 39-mer coverages for the consensus chunk of rDNA unit vs. some generic "1×" ordinary sequence in the nuclear genome (that N/n-free chunk of chr. 1 with length 440,320 bp, with a coverage threshold to remove empirically non-unique regions) provides an estimate of rDNA unit copy number as 840× (independent of the chunk's tandem circle not being closed), and ~5.5 Mbp as a lower bound on total length (dependent on the fraction of the unit the chunk represents).

Number of tRNAs Called in Sequenced Genome:

counts are for all types (including with introns, unclassified, selenocysteine, and pseudo). For AraTha, the TAIR release contains explicit tRNA annotations, and the table entry '631' counts these. For the other organisms, even though, e.g., the original genome papers generally discuss tRNAs (implying that predictions were made), the annotation releases do not identify tRNAs and so for this work ab initio scans with tRNAscan-SE 1.3.1 were performed with default parameters. (This scan finds 639 for AraTha.) For MonNeg, the ab initio scan found 38 in the nuclear genome, 29 in the chloroplast, and 23 in the mitochondrion, while the original genome paper (54) states "40+1× Pseudo Ser-tRNA" for nuclear, "29+1× Pseudo Leu-tRNA" for the chloroplast, and "21+1× Pseudo Met-tRNA" for the mitochondrion in its Table 3 but shows 23 in its FIG. 5. For ChlRei, the '259' shown in Table 1 is taken from the original genome paper (52), as even though the current JGI 5.5 release does not contain tRNA annotations, the original genome paper states that tRNAscan-SE is known to overestimate in *Chlamydomonas* due to tRNA-associated SINE retrotransposon elements; the ab initio scan predicts 353 tRNAs in the current nuclear assembly. Regarding ChrZof, the scan only identifies 75 tRNAs (SI File S9)—more than Chlore and MonNeg, the small algal genomes of high G+C and moderate repeat content, and similar to CocSub, the other algal genome of moderate G+C and low repeat content, but much less than the relatively large genomes of AraTha and ChlRei; there are no large clusters, although there are runs of up to four on the same chromosome with spacing smaller than would be expected at random (e.g., with some adjacencies closer than 1 Kbp).

TABLE S2

| Organism: | # selenocysteine: | # pseudo: | # undetermined: | missing std. AAs: |
|---|---|---|---|---|
| CocSub | 0 | 3 | 4 | none |
| ChrZof | 0 | 0 | 0 | none |
| AraTha (ab initio) | 0 | 8 | 1 | none |
| ChlRei (ab initio) | 1 | 2 | 2 | none |
| Chlore | 1 | 0 | 0 | Ile |
| MonNeg | 2 | 1 | 1 | Asn, Glu, Trp, Tyr |

From the ab initio scans, all standard amino acids are covered for all six organisms, except for one in Chlore and four in MonNeg, perhaps because these are the most fragmented assemblies, or perhaps due to tRNAscan-SE misclassifications as selenocysteine/pseudo/undetermined (of which there are exactly one and four in Chlore and MonNeg, respectively). The phylogenetic profile of anticodons (ignoring predicted pseudogene status) is as follows: universal in all six=AGC, AGG, AGT, CAA, CAC, CAT, CGC, CTG, CTT, GAA, GCA, GCC, GTC, GTG, TCG; missing from all six=AAA, ACA, ACT, ATA, ATG, ATT, CTA, GAC, GCG, GGC, GGG, GGT, TTA; missing from just MonNeg=AAC, AAG, ACG, CAG, CCA, CGA, CGG, CTC, GTA, GTT, TAA, TGG; missing from MonNeg and Chlore=AAT, CCG, CCT, TAC, TCC, TGA, TGC, TGT, TTC, TTG; missing from just Chlore=CCC, CGT, GCT, TAG, TAT, TCT; missing from MonNeg, Chlore, and ChrZof=AGA, TTT; just AraTha=ACC, GAG; just ChlRei=ATC; just MonNeg=GAT; just AraTha and CocSub=GGA; and just ChlRei, Chlore, and MonNeg=TCA.

Number of amino acids: {average, median}: gene models are taken without question (e.g., even if one does not start with a start codon, end with a stop codon, has coding sequence not a multiple of three nucleotides in length, the coding sequence contains IUPAC ambiguities, the coding sequence is very long) and the result rounded to the nearest integer. Number of exons containing coding sequence: {average, median}: gene models are taken without question (e.g., no matter how many exons they have) and the result rounded to the nearest tenth. Exon length (restricted to coding sequence): {average, median}; Intron length (between exons with coding sequence): {average, median}; Percentage with at least one intron (between exons with coding sequence): same comments as for "Number of amino acids: average".

% of Seq. Basepairs RepeatMasker'd with {Repbase Update "Eukaryotic", RepeatModeler, RepeatModeler+ Repbase Update "Eukaryotic"}:

the RepeatMasker/Repbase/RepeatModeler analysis discussed earlier for ChrZof under subsection Repetitive sequence was applied to the other five organisms with the same parameters. Masking was variously with just known repeats (Repbase only), just de novo repeats from RepeatModeler, and the combination of the two.

Chloroplasts.

For chloroplast genomes, reference sequences and annotations were as follows. CocSub: NCBI accession NC_015084.1 (with one sequence gap and lacking a large inverted repeat) and annotations. ChrZof: chrCp of the ChrZofV5 release of the present work. AraTha: NCBI accession AP000423.1 sequence and annotations. ChlRei: NCBI accession FJ423446.1 sequence and annotations. Chlore: NCBI accession KP271969.1 sequence (lacking a large inverted repeat) and annotations. MonNeg: NCBI accession CM002678.1 sequence, but with annotations from FIG. 4 of the original genome paper (54) as the annotations deposited at NCBI are manifestly highly incomplete. Sequenced genome size. The number of non-N/n bases in the assembly (other IUPAC ambiguities being tolerated) is reported, rounded to the nearest Kbp. Number of annotated protein-coding genes, including hypotheticals; Number of annotated {rRNAs, tRNAs}: if the genome contains large repeats (as common in chloroplasts), genes are counted as +1 copy for each copy of the parent repeat. For tRNAs, as with the nuclear genome, if no annotations were provided, an ab initio tRNAscan-SE scan was performed (and all types counted). Percent G+C in sequenced genome: using only A/C/G/T bases (no IUPAC ambiguities) in an all-uppercase version of the assembly, the fraction (#C+G)/(#A+C+G+T) is reported as a percentage rounded to the nearest integer.

Mitochondria.

For mitochondrial genomes, reference sequences and annotations were as follows. CocSub: NCBI accession NC_015316.1 sequence and annotations. ChrZof: chrMt of the ChrZofV5 release of the present work. AraTha: NCBI accession JF729201.1 sequence and annotations. ChlRei: NCBI accession NC_001638.1 sequence and annotations. Chlore: NCBI accession NC_025413.1 sequence and annotations. MonNeg: NCBI accession CM002677.1 (with two sequence gaps) and annotations. Rows are the same as for chloroplasts, except for the following note not already mentioned elsewhere: the MonNeg mitochondrial sequence has no rRNA annotations (and two sequence gaps); RNAmmer does not find any rDNA, but Rfam finds four zones with LSU/SSU fragments.

Calling of Protein-Coding Gene Families Across the Six Organisms of Main Text Table 1

To call gene families simultaneously across AraTha, ChlRei, ChrZof, CocSub, Chlore, and MonNeg (the six organisms of Table 1 of the main text), the amino acid sequences of the genes corresponding to row "Number of called protein-coding gene loci (collapsing transcript forms)" of Table 1 were collected. Alignment seeds were formed by running NCBI BLASTP+ 2.4.0 with E-value threshold $10^{-5}$ and soft masking (segmasker window 12, locut 2.2, hicut 2.5) on both queries and subjects (and otherwise defaults, including BLOSUM62 scoring). For every distinct ordered pair (query, subject) with at least one BLASTP+ result, global Needleman-Wunsch alignment was performed with the C++ library Parasail (BLOSUM62 scoring with gap open and extend penalties 10 and 1, respectively). Compared to the local alignments of BLASTP, the global alignment score captures not only sequence similarity, but also aspects of the fraction of the entirety of query and subject aligned and the ordering of homologous fragments (e.g., component protein domains).

In the first phase, "self-prefamilies" were formed within each organism. For Parasail-aligned pairs of genes (query, subject=query) with global alignment score s≥16, keep as "tentative arcs" those Parasail pairs (query, subject in same organism except query itself) with global alignment score≥85% of s. Remove tentative arcs (query, subject) for which (subject, query) is not a tentative arc, so as to obtain unordered pairs {gene, different gene in same organism} that constitute edges in an undirected graph. Partition vertices of this graph (the pieces of this partition being the self-prefamilies) by subdividing the vertices of each connected component as follows: (1) find all maximal cliques in the connected component; (2) keep only cliques of maximum size; (3) expand each clique to also contain those vertices in the connected component that are adjacent to at least half the vertices in the clique; (4) keep only expanded cliques of maximum size by number of vertices in them; (5) group vertices in the union of the surviving expanded cliques by their combination of membership status in the surviving expanded cliques, these groups becoming pieces of the final partition; and (6) recurse [going back to (1)] on any vertices remaining. Finally, each gene in the organism not represented is added as a singleton self-prefamily (of size 1). Self-prefamilies involve 1 to 31 genes (but only 1 to 4 genes each when restricting to sizes occurring ≥10 times in any single organism, and only 1 or 2 genes each when restricting to sizes seen ≥100 times in any single organism). The percent of genes in self-prefamilies of size ≥2 is ~8.4% and ~4.6% in the large genomes AraTha and ChlRei, respectively; ~2.9% and ~2.2% in the algal moderate G+C content genomes CocSub and ChrZof of low repetitive sequence fraction, respectively; and ~1.1% and ~0.9% in the algal high G+C genomes Chlore and MonNeg of moderate repetitive sequence fraction, respectively.

Self-prefamilies exhibit evidence of tandem duplication events in all six genomes. For example, consider self-prefamilies of size exactly 2. (Across organisms, this is ~73% to ~96% of self-prefamilies of size ≥2.) Given such a self-prefamily, classify it as type "Far" if the two genes are on different sequences in the reference genome or the midpoint of the bounds of their coding sequences are ≥20 Kbp apart; otherwise, classify it as type "Near$^+$" if the two genes are on the same strand or "Near$^-$" if they are on opposite strands. There is enrichment for Near and larger enrichment for Near$^+$ in every organism:

TABLE S3

| Organism: | # observed: | | | random expectation: | | | observed/expected: | | |
|---|---|---|---|---|---|---|---|---|---|
| | Far | Near$^+$ | Near$^-$ | Far | Near$^+$ | Near$^-$ | Far | Near$^+$ | Near$^-$ |
| AraTha | 714 | 214 | 30 | ~958 | ~0.181 | ~0.170 | ~0.75 | ~1,184 | ~176 |
| ChlRei | 146 | 58 | 30 | 234 | 0.040 | 0.041 | 0.62 | 1,454 | 725 |
| Chlore | 20 | 16 | 6 | 42 | 0.017 | 0.018 | 0.48 | 943 | 328 |
| ChrZof | 104 | 12 | 8 | 124 | 0.040 | 0.040 | 0.84 | 298 | 199 |
| CocSub | 41 | 13 | 1 | 55 | 0.020 | 0.023 | 0.75 | 649 | 44 |
| MonNeg | 59 | 9 | 1 | 69 | 0.006 | 0.006 | 0.86 | 1,512 | 174 |

In the second phase, "prefamilies" are formed—these target orthologs ("primaries") and generally involve more than one organism. For Parasail-aligned pairs (query, subject in different organism) sharing the same query, drop all these pairs if the best global alignment score s is <16 and otherwise keep only pairs with global alignment score ≥97% of s. Replace kept ordered pairs of genes (query, subject) with ordered pairs (self-prefamily of query, self-prefamily of subject) and thin ordered pairs seen more than once down to a single copy. Taking these as the new "tentative arcs", follow the same procedure as used to form self-prefamilies, except the resulting partition pieces now constitute the prefamilies. Each of these involves 1 to 15 self-prefamilies; ~67% and ~90% of genes in multi-organism prefamilies belong to prefamilies with at most 1 and at most 2, respectively, self-prefamilies per organism.

In the third phase, final families are formed—with paralogs now also targeted as "additional" genes in each family—by merging into each multi-organism prefamily zero or more single-organism prefamilies. Each single-organism prefamily S is considered independently one at a time: for each gene a in S, gather Parasail alignments (a, gene b in a multi-organism prefamily) and (gene b in a multi-organism prefamily, a), keep only alignments with maximum global alignment score, and note the multi-organism prefamilies that surviving b belong to; if exactly one multi-organism prefamily M is noted after all a are considered and at least one kept alignment was seen with strictly positive global alignment score, then S is merged into M as additional genes (and otherwise S is left alone). 5,258 multi-organism prefamilies receive merges, each 1 to 196 times, with ~88% of these ≤6 times. There are 41,328 final families (these partitioning all 27,206+17,741+15,344+9,629+9,791+16,734=96,445 genes from AraTha, ChlRei, ChrZof, CocSub, Chlore, and MonNeg, with each gene belonging to exactly one final family), with 30,838 and 10,490 involving single vs. multiple organisms, respectively. Of the 10,490, 5,012 have ≤1 gene (primary+additional) per organism and 7,904 have ≤2 genes. The largest families are of various histone proteins.

statistically enriched regions, each assembly sequence is partitioned into as equal-sized pieces as possible with each piece being ≈1 Mbp (small sequences are taken whole); this induces a 2-D partitioning of the plotted area, and the number of observed gene pairs (red plus green dots) in each 2-D bin is noted. Randomized versions of the plot are then generated: for each version, the identities of all genes are shuffled in each genome and new numbers of points in each 2-D bin tallied; the p-value for a 2-D bin is taken as the fraction of times the random tally is larger than the observed tally over 100,000 randomizations. These p-values are used to shade the background of 2-D bins from white (p-values above 0.01) to increasingly orange on a logarithmic scale to deepest orange for p-values near 0.00001.

TABLE S4

| Reference genome: | % of reference genes that belong to multi-organism families: | Same, except multi-orgo. family restricted to having ≤ 2 genes (primary + add'l) per organism: | Same, except multi-organism family has ≤ 1 gene per organism: |
|---|---|---|---|
| AraTha | ~60% | ~18% | ~7% |
| ChlRei | 64% | 37% | 21% |
| Chlore | 83% | 52% | 29% |
| ChrZof | 73% | 47% | 27% |
| CocSub | 77% | 50% | 26% |
| MonNeg | 63% | 39% | 20% |

Details of Main Text FIG. 2

Phylogram.

The 813 protein-coding gene families (called across the six organisms of main text Table 1) that have no additional genes and exactly one primary gene in each of the six organisms were identified. Because of the highly fragmentary nature of the MonNeg assembly (and the possibility of artificially truncated gene coding sequences), an additional condition that the shortest protein across the six organisms is ≥85% of the length of the longest protein was also imposed, resulting in 75 families with an average of ∞27K amino acids per organism. Multiple alignments and phylogram estimation were by the ETE Toolkit sptree_fasttree_all/standard_fasttree pipelines (56, 57). Alternatively, if MonNeg is ignored, there are 1,253 families before the similar length requirement, and if this requirement is loosened from 85% to 50%, 978 families with an average of ≈497K amino acids per organism proceed to the same ETE pipelines, and the resulting phylogram is very similar to that shown with just a slightly higher average rate of amino acid changes but similar proportions; this phylogram was stable when the 978 families were randomly partitioned into six groups of 163 families each. An analysis based on 16S/18S rRNA nucleotide sequences extracted from NCBI also produces a similar phylogram (but with a much lower average rate of nucleotide change). The topology of all these trees is in agreement with Leliaert, et al. (58).

Proportional Venn Diagram.

The protein-coding gene families containing the 15,274 genes of ChrZof were partitioned into eight classes based on the subset of MonNeg, ChlRei, and AraTha that have at least one gene (primary or additional) in the family. The number of ChrZof genes in each class is shown as a proportional Venn diagram using eulerAPE (59)-determined ellipses.

Scatter Plot Showing Scrambled Syntenic Blocks.

This is similar to FIG. 2 for CocSub vs. Chlore in Blanc, et al. (51), but with a finer scheme for generating statistical enrichment shading as well as permutation of genome assembly sequences to emphasize enrichments. To identify The plotted order of genome assembly sequences along each axis is determined as follows. Reordering is only performed among those sequences ("large") in an assembly ≥0.5 Mbp long. First, consider 2-D bins with p-values at or below 0.01, and form a directed graph with arcs from x-axis large sequences to y-axis large sequences with arc weights given by the total number of red plus green dots in considered 2-D bins that land in the pair of sequences, deleting arcs of weight zero. Using the Centrality method of FindGraphCommunities [ ] in Mathematica, partition the sequences into an ordered list of clusters. Start by considering in turn those clusters that involve both genomes: find a maximal-weight matching for the subgraph of the current cluster, place ordered pairs (x-axis assembly original sequence number, y-axis assembly original sequence number) for the matching is ascending lexicographic order, and take these as the next sequences in the reordering for both genomes; if the matching does not involve all sequences in the cluster, add the leftover sequences by ascending original assembly order. Finally, after all clusters involving both genomes are processed, in each genome add in all sequences not yet included in ascending original assembly order.

Gene Prediction and Functional Annotation

Ab initio gene models were constructed with AUGUSTUS 3.0.3 using default parameters except where noted as follows. PASA 2.0.2 (50) was used to extract a training set of 6,576 genes from the assembled transcriptome. Prediction hints for AUGUSTUS were created by aligning the transcriptome to the genome with BLAT 35. Functional annotations were generated from protein translations of predicted gene models. For example, BLAST2GO 6.0 (60) was used to associate Gene Ontology (GO, 61) terms as well as brief textual descriptions to genes. To generate protein domain/family annotations, protein translations were scanned against PfamA release 29 with HMMER 3.1b2 (62). Additional GO associations were derived using the Pfam2GO translation table from EMBL-EBI (63). All functional enrichment analyses were based on hypergeometric statistical tests using the annotations of the entire genome as background.

Astaxanthin-Deficient Mutants

A non-targeted forward genetics screen generated astaxanthin-deficient mutants. Cells were grown to log phase ($2-5\times10^6$ cells/mL), subjected to ultraviolet radiation (80,000 μjoules), and plated onto selection media (proteose media with 28 mM glucose). The selection media enhances the production of astaxanthin, which causes the cells to become pink; therefore green colonies were selected as astaxanthin candidate mutants. The lack of astaxanthin production was confirmed by HPLC pigment analysis. To analyze pigments, cells were scraped from plates and homogenized with acetone and lysing matrix D for 2×60 s with the FastPrep-24 (6.5 m s$^{-1}$, MP Biomedical). The cell debris was pelleted by centrifugation (20,000 g for 3 min) and the supernatant was removed. To ensure complete extraction, another aliquot of acetone was added to the cell debris pellet and the extraction process was repeated; pigments were determined by HPLC as previously described (64). To sequence the β-carotene ketolase gene from *C. zofingiensis* wild type and astaxanthin mutants, a series of synthetic primers (Table S3) were used to amplify overlapping fragments of genomic DNA. Sequences were assembled using Lasergene MegAlign (DNASTAR) and putative point mutations were identified.

Liquid cultures of wild type and astaxanthin mutants were grown until log phase under medium light (100 μmol photons m$^{-2}$s$^{-1}$) and then high light treatment cultures were moved to 400-450 μmol photons m$^{-2}$s$^{-1}$ for 10 days. Replicates (N=3 or 4) were harvested by centrifugation and the cell pellet was frozen in liquid nitrogen. Pigment determination was conducted as described above. Pigment concentrations were tested for assumptions of normality and homoscedasticity, and data were log-transformed accordingly prior to analyses. ANOVA was used to test the effects of high light. For all significant factors in the ANOVA tests, post-hoc Tukey-Kramer HSD pairwise comparisons were used to test which groups were significantly different. α-carotene concentrations were not normally distributed and the Kruskal-Wallis non-parametric test was used instead to evaluate statistical differences. Statistical differences were reported significant at the $\alpha=0.05$ level.

SUPPLEMENTAL INFORMATION REFERENCES

1. Parkinson D Y, et al. (2013) Nanoimaging cells using soft X-ray tomography. *Methods Mol Biol* 950:457-481.
2. Le Gros M A, et al. (2012) Visualizing sub-cellular organization using soft X-ray tomography. Comprehensive Biophysics, Biophysical Techniques for Characterization of Cells, ed Egelman E H (Academic Press, Oxford), Vol 2, pp 90-110.
3. Le Gros M, et al. (2014) Biological soft X-ray tomography on beamline 2.1 at the Advanced Light Source. *J Synchrotron Radiat* 21(Pt 6):1370-1377.
4. Kremer J R, Mastronarde D N, & McIntosh J R (1996) Computer visualization of three-dimensional image data using IMOD. *J Struct Biol* 116(1):71-76.
5. github.com/vsbuffalo/scythe
6. Dobin A, et al. (2013) STAR: ultrafast universal RNA-seq aligner. *Bioinformatics* 29(1):15-21.
7. Trapnell C, et al. (2012) Differential gene and transcript expression analysis of RNA-seq experiments with TopHat and Cufflinks. *Nat Protoc* 7(3):562-578.
8. Goff L, Trapnell C, & Kelley D (2013) cummeRbund: Analysis, exploration, manipulation, and visualization of Cufflinks high-throughput sequencing data. R package version 2.16.0.
9. Gautier L, Cope L, Bolstad B M, & Irizarry R A (2004) affy—analysis of Affymetrix GeneChip data at the probe level. *Bioinformatics* 20(3):307-315.
10. Love M I, Huber W, & Anders S (2014) Moderated estimation of fold change and dispersion for RNA-seq data with DESeq2. *Genome Biol* 15(12):550.
11. Boisvert S, Raymond F, Godzaridis E, Laviolette F, & Corbeil J (2012) Ray Meta: scalable de novo metagenome assembly and profiling. *Genome Biol* 13(12):R122.
12. Simpson J T, et al. (2009) ABySS: A parallel assembler for short read sequence data. *Genome Res* 19(6):1117-1123.
13. Ribeiro F J, et al. (2012) Finished bacterial genomes from shotgun sequence data. *Genome Res* 22(11):2270-2277.
14. Gnerre S, et al. (2011) High-quality draft assemblies of mammalian genomes from massively parallel sequence data. *Proc Natl Acad Sci USA* 108(4):1513-1518.
15. Langmead B, Trapnell C, Pop M, & Salzberg S L (2009) Ultrafast and memory-efficient alignment of short DNA sequences to the human genome. *Genome Biol* 10(3):R25.
16. Langmead B & Salzberg S L (2012) Fast gapped-read alignment with Bowtie 2. *Nat Meth* 9(4):357-359.
17. Kim D, Langmead B, & Salzberg S L (2015) HISAT: a fast spliced aligner with low memory requirements. *Nat Meth* 12(4):357-360.
18. Altschul S F, Gish W, Miller W, Myers E W, & Lipman D J (1990) Basic local alignment search tool. *J Mol Biol* 215(3):403-410.
19. Camacho C, et al. (2009) BLAST+: architecture and applications. *BMC Bioinf* 10:421.
20. Kielbasa S M, Wan R, Sato K, Horton P, & Frith M C (2011) Adaptive seeds tame genomic sequence comparison. *Genome Res* 21(3):487-493.
21. Harris R (2007) Improved pairwise alignment of genomic DNA. Ph.D. Thesis (The Pennsylvania State University).
22. Kent W J (2002) BLAT—the BLAST-like alignment tool. *Genome Res* 12(4):656-664.
23. Chaisson M J & Tesler G (2012) Mapping single molecule sequencing reads using basic local alignment with successive refinement (BLASR): application and theory. *BMC Bioinf* 13:238.
24. Daily J (2016) Parasail: SIMD C library for global, semi-global, and local pairwise sequence alignments. *BMC Bioinf* 17:81.
25. Hackl T, Hedrich R, Schultz J, & Förster F (2014) proovread: large-scale high-accuracy PacBio correction through iterative short read consensus. *Bioinformatics* 30(21):3004-3011.
26. github.com/jstjohn/SeqPrep
27. Martin M (2011) Cutadapt removes adapter sequences from high-throughput sequencing reads. *EMBnet.journal* 17(1):10-12.
28. Marcais G & Kingsford C (2011) A fast, lock-free approach for efficient parallel counting of occurrences of k-mers. *Bioinformatics* 27(6):764-770.
29. Kurtz S, et al. (2004) Versatile and open software for comparing large genomes. *Genome Biol* 5(2):R12.
30. Benson G (1999) Tandem repeats finder: a program to analyze DNA sequences. *Nucl Acids Res* 27(2):573-580.
31. Warburton P E, Giordano J, Cheung F, Gelfand Y, & Benson G (2004) Inverted repeat structure of the human 32. Smit A, Hubley R, & Green P (2013-2015) RepeatMasker Open-4.0. www.repeatmasker.org.
33. Bao W, Kojima K K, & Kohany O (2015) Repbase Update, a database of repetitive elements in eukaryotic genomes. *Mobile DNA* 6:11.
34. Smit A & Hubley R (2008-2015) RepeatModeler Open-1.0. www.repeatmasker.org.
35. Stanke M, Schoffmann O, Morgenstern B, & Waack S (2006) Gene prediction in eukaryotes with a generalized hidden Markov model that uses hints from external sources. *BMC Bioinf* 7:62.
36. Lowe T M & Eddy S R (1997) tRNAscan-S E: a program for improved detection of transfer RNA genes in genomic sequence. *Nucl Acids Res* 25(5):0955-0964.
37. Fiume M, Williams V, Brook A, & Brudno M (2010) Savant: genome browser for high-throughput sequencing data. *Bioinformatics* 26(16):1938-1944.
38. Freese N H, Norris D C, & Loraine A E (2016) Integrated genome browser: visual analytics platform for genomics. *Bioinformatics* 32(14):2089-2095.
39. Thorvaldsdottir H, Robinson J T, & Mesirov J P (2013) Integrative Genomics Viewer (IGV): high-performance genomics data visualization and exploration. *Briefings in Bioinformatics* 14(2):178-192.
40. Krzywinski M, et al. (2009) Circos: an information aesthetic for comparative genomics. *Genome Res* 19(9):1639-1645.
41. Li H, et al. (2009) The sequence alignment/map format and SAMtools. *Bioinformatics* 25(16):2078-2079.
42. github.com/thegenemyers/DEXTRACTOR
43. Anders S, Pyl P T, & Huber W (2014) HTSeq—a Python framework to work with high-throughput sequencing data. *Bioinformatics* 31(2):166-169.
44. Rice P, Longden I, & Bleasby A (2000) EMBOSS: the European Molecular Biology Open Software Suite. *Trends Genet* 16(6):276-277.
45. www.ncbi.nlm.nih.gov
46. Finn R D, et al. (2016) The Pfam protein families database: towards a more sustainable future. *Nucl Acids Res* 44(D1):D279-D285.
47. Nawrocki E P, et al. (2015) Rfam 12.0: updates to the RNA families database. *Nucl Acids Res* 43(D1):D130-D137.
48. Lagesen K, et al. (2007) RNAmmer: consistent and rapid annotation of ribosomal RNA genes. *Nucleic Acids Res* 35(9):3100-3108.
49. The *Arabidopsis* Genome Initiative (2000) Analysis of the genome sequence of the flowering plant *Arabidopsis thaliana*. *Nature* 408(6814):796-815.
50. Haas B J, et al. (2003) Improving the *Arabidopsis* genome annotation using maximal transcript alignment assemblies. *Nucl Acids Res* 31(19):5654-5666.
51. Blanc G, et al. (2012) The genome of the polar eukaryotic microalga *Coccomyxa subellipsoidea* reveals traits of cold adaptation. *Genome biology* 13(5):R39.
52. Merchant S S, et al. (2007) The *Chlamydomonas* genome reveals the evolution of key animal and plant functions. *Science* 318(5848):245-251.
53. Blanc G, et al. (2010) The *Chlorella variabilis* NC64A genome reveals adaptation to photosymbiosis, coevolution with viruses, and cryptic sex. *Plant Cell* 22(9):2943-2955.
54. Bogen C, et al. (2013) Reconstruction of the lipid metabolism for the microalga *Monoraphidium neglectum* from its genome sequence reveals characteristics suitable for biofuel production. *BMC Genomics* 14:926.
55. Chandrasekhara C, Mohannath G, Blevins T, Pontvianne F, & Pikaard C S (2016) Chromosome-specific NOR inactivation explains selective rRNA gene silencing and dosage control in *Arabidopsis*. *Genes Dev* 30(2): 177-190.
56. Huerta-Cepas J, Serra F, & Bork P (2016) ETE 3: Reconstruction, analysis, and visualization of phylogenomic data. *Mol Biol Evol* 33(6):1635-1638.
57. Price M N, Dehal P S, & Arkin A P (2010) FastTree 2—approximately maximum-likelihood trees for large alignments. *PLoS ONE* 5(3):e9490.
58. Leliaert F, et al. (2012) Phylogeny and molecular evolution of the green algae. *Crit Rev Plant Sci* 31(1):1-46.
59. Micallef L & Rodgers P (2014) eulerAPE: drawing area-proportional 3-Venn diagrams using ellipses. *PLoS ONE* 9(7):e101717.
60. www web address blast2go.com/
61. Consortium TGO (2015) Gene Ontology Consortium: going forward. *Nucl Acids Res* 43(D1):D1049-D1056.
62. Eddy S R (2012) A new generation of homology search tools based on probalistic inference. *Genome Informatics* 2009, (Imperial College Press), pp 205-211.
63. geneontology.org/external2go/pfam2go (2016 Sep. 17 11:36:45).
64. Baroli I, Do A D, Yamane T, & Niyogi K K (2003) Zeaxanthin accumulation in the absence of a functional xanthophyll cycle protects *Chlamydomonas reinhardtii* from photooxidative stress. *Plant Cell* 15(4):992-1008.

All patents, patent applications, accession numbers, and other published reference materials cited in this specification are hereby incorporated herein by reference in their entirety for their disclosures of the subject matter in whose connection they are cited herein.

What is claimed is:

1. An expression vector comprising a nucleic acid sequence that encodes a polypeptide involved in astaxanthin production, wherein the polypeptide has at least 95% identity to SEQ ID NO:3.

2. The expression vector of claim 1, wherein the polypeptide comprises the amino acid sequence of SEQ ID NO:3.

3. The expression vector of claim 1, wherein the nucleic acid sequence is a cDNA or genomic DNA sequence from a *Chromochloris zofingiensis* gene.

4. The expression vector of claim 1, wherein the nucleic acid sequence is operably linked to a heterologous promoter.

5. The expression vector of claim 1, wherein the expression vector is integrated into a host cell chromosome.

6. The expression vector of claim 1, wherein the nucleic acid sequence has at least 95% identity to SEQ ID NO: 10 or SEQ ID NO: 17.

7. A host cell comprising expression vector of claim 1.

8. A host cell comprising a heterologous nucleic acid sequence encoding at least one polypeptide involved in astaxanthin production, wherein the at least one polypeptide involved in astaxanthin production has at least 95% identity to SEQ ID NO:3.

9. The host cell of claim 8, wherein the at least one polypeptide comprises the amino acid sequence of SEQ ID NO:3.

10. The host cell of claim 8, comprising a heterologous nucleic acid encoding an additional polypeptide, wherein the additional polypeptide comprises an amino acid sequence of SEQ ID NO:1, 2, 4, 5, 6, or 7.

11. A method of producing astaxanthin, the method comprising culturing a host cell of claim 7 under conditions in which astaxanthin is produced.

12. An isolated nucleic acid comprising the cDNA sequence of SEQ ID NO:17.

* * * * *

SEQUENCE LISTING

```
<160> NUMBER OF SEQ ID NOS: 41

<210> SEQ ID NO 1
<211> LENGTH: 398
<212> TYPE: PRT
<213> ORGANISM: Chromochloris zofingiensis

<400> SEQUENCE: 1

Glu Ala Ala Leu Thr Thr Ala Val Asp Ala Ala Ala Ala Leu Arg Asn
1               5                   10                  15

Asn Ile Gly Phe Leu Gln Arg Ser Gln Ile Ala Ile Val Ala Ala Phe
            20                  25                  30
```

```
Leu Ser Ala Ile Tyr Leu Lys Leu Val Val Ser Arg Ile Ala Pro Gly
        35                  40                  45

Trp Lys Ser Leu Ala Leu Val Ala Pro Leu Leu Ala Leu Asn Leu Trp
    50                  55                  60

Leu Pro Leu Leu Phe His Met Arg Glu Glu Val Val Ser Arg Thr Cys
65                  70                  75                  80

Val Val Phe Leu Ile Ser Trp Leu Gly Ser Phe Lys Ala Ile Gly Met
                85                  90                  95

Cys Leu Asn Arg Gly Pro Leu Ala Ala Asp Trp Ser Val Ala Gln Met
            100                 105                 110

Ile Phe Leu Tyr Val Ala Pro Val Leu Pro Arg Gln Asp Ala Gly Gly
                115                 120                 125

Pro Val Lys Ala Gly Arg Leu Gln Asp Ser Ala Gly Thr Trp Gly Thr
            130                 135                 140

Leu Ala Ala Ser Phe Val Ile Asn Thr Thr Ile Leu Gly Val Val Ser
145                 150                 155                 160

Tyr Leu Leu Val Val Met Asp Met Pro Lys Val Val Lys Ile Tyr Ile
                165                 170                 175

Tyr Ala Leu Gly Leu Tyr Gly Phe Val Ser Phe Ile Met Glu Gly Pro
            180                 185                 190

Ala Ala Ile Ile Val Gly Leu Leu Arg Ile Glu Leu Val Pro Pro Phe
                195                 200                 205

Asp Lys Pro Trp Leu Ala Thr Ser Leu Ala Asp Phe Trp Gly Arg Arg
            210                 215                 220

Trp Asn Asn Ser Thr Ser Leu Leu Leu Arg Phe Leu Val Tyr Asp Pro
225                 230                 235                 240

Ile Ile Glu Gly Arg Leu Val Lys Lys Ala Lys Gln Glu Asp Pro Gln
                245                 250                 255

Gln Pro Ala Pro Ser Lys Gln Val Ser Asn Ser Met Arg Leu Thr Ala
            260                 265                 270

Met Leu Ala Thr Phe Ala Leu Ser Gly Leu Ile His Glu Ala Ile Leu
        275                 280                 285

Ala Tyr Val Asn Arg Pro Tyr Tyr Pro Gly Pro Trp Phe Met Phe Phe
    290                 295                 300

Phe Ile Gln Gly Pro Leu Leu Ala Val Glu Met Arg Val His Lys His
305                 310                 315                 320

Leu Arg Ala Thr His Lys Gln Leu Pro Phe Thr Ala Ala Trp Thr Leu
                325                 330                 335

Thr Thr Ala Cys Leu Leu Leu Thr Ala Tyr Met Phe Phe Phe Pro Pro
            340                 345                 350

Ile Glu Asp Trp Thr Asp Leu Ala Pro Arg Ile Ala Gln Ala Val Thr
                355                 360                 365

Ser Asn Phe Gln Ala Val Leu Gly Pro Leu Gln Gly Leu Gly Arg Gln
            370                 375                 380

Tyr Trp Ala Val Ala Ala Gly Leu Val Gln Gln Ser Ala Ile
385                 390                 395
```

<210> SEQ ID NO 2
<211> LENGTH: 375
<212> TYPE: PRT
<213> ORGANISM: Chromochloris zofingiensis

<400> SEQUENCE: 2

Pro Val Pro Val Ser Thr Thr His Pro Asn Gly Lys Gly Met Arg Ala

```
  1               5                   10                  15
Ala Asn Leu Thr Glu Leu Pro Thr Glu Gly Pro Phe Ser Arg Ser Leu
             20                  25                  30
Lys Gln Lys Glu Asp Ser Ala Asn Thr Gly Ala Asp Ala Ile Ala Leu
             35                  40                  45
Gln Thr Asn Gly Thr Ala Asp Ala Ser Leu Asp Ala Asn Ala Pro Ser
             50                  55                  60
Pro Leu Pro Glu Pro Gly Pro Ser Val Leu Val His His Leu Asp Phe
 65                  70                  75                  80
Thr Tyr Pro Gly Leu Asp Gly Arg Pro Val Pro Gly Gln Pro Pro Leu
                 85                  90                  95
Ile Thr Asp Met Cys Leu Thr Leu Gln Pro Gly Ser Arg Cys Leu Leu
                100                 105                 110
Ile Gly Ala Asn Gly Ala Gly Lys Thr Thr Leu Leu Lys Ile Leu Gly
                115                 120                 125
Gly Lys His Met Val Pro Lys Asp Ala Val His Ile Leu Gly Ala Pro
            130                 135                 140
Pro Phe His Asp Thr His Leu Thr Thr Ser Gly His Leu Ser Tyr Ile
145                 150                 155                 160
Gly Gly Asn Trp Thr Arg Asp Ile Ala Phe Ala Gly Leu Ser Ile Pro
                165                 170                 175
Leu Thr Gly Asp Phe Pro Ala Ser Arg Met Ile Asp Ala Ile Pro Glu
            180                 185                 190
Val Asp Pro Ala Arg Lys Glu Arg Leu Ile Lys Val Leu Asp Ile Asp
            195                 200                 205
Pro Asn Trp Arg Met His Thr Val Ser Asp Gly Gln Arg Arg Arg Val
210                 215                 220
Gln Ile Cys Val Gly Leu Leu Arg Pro Phe Lys Val Leu Leu Leu Asp
225                 230                 235                 240
Glu Ile Thr Val Asp Leu Asp Val Leu Gly Arg Ala Asp Leu Met His
                245                 250                 255
Phe Leu Ala Asp Glu Cys Ala Thr Arg Gly Ala Ser Ile Ile Tyr Ala
            260                 265                 270
Thr His Ile Phe Asp Gly Leu Glu Phe Trp Pro Thr His Val Ala Tyr
        275                 280                 285
Val Ala Arg Gly Arg Leu Gln Met Val Lys Ser Ala Glu Glu Ile Ser
            290                 295                 300
Glu Leu Lys Gln Gly Arg Leu Leu Glu Leu Val Thr Ser Leu Leu Arg
305                 310                 315                 320
Glu Glu Arg Glu Ala Val Lys Ala Ala Gly Val Ser Lys Pro Leu Glu
                325                 330                 335
Tyr Asp Pro Ser Leu Glu Gly Gln Val Thr Asn Phe Ser Tyr Ala Phe
            340                 345                 350
Asn Asn Gly Trp Val Pro Gly Thr Leu Ser Thr Ser Leu Ala Lys Ser
        355                 360                 365
Thr Asn Ala Val Met Arg Asn
370                 375
```

<210> SEQ ID NO 3
<211> LENGTH: 1321
<212> TYPE: PRT
<213> ORGANISM: Chromochloris zofingiensis

<400> SEQUENCE: 3

-continued

```
Leu Gln Arg Ile Val Gly Gly Leu Gln Cys Tyr Ala Arg Gln Gln Ala
 1               5                  10                 15

Val Pro Ser Val Gln Cys Pro Glu Asn Ala Tyr Leu Tyr Tyr Trp Ile
             20                  25                 30

Ile Gly Leu Ser Leu Ala Pro Leu Leu Gln Ser Leu Ala Glu Asn Ser
         35                  40                  45

Met Asn Phe Glu Leu Ser Val Ile Gly Thr Arg Met Arg Asn Gly Leu
 50                  55                  60

Met Ala Ala Ile Tyr Arg Lys Cys Leu Arg Leu Ser Asn Ser Ala Ile
 65                  70                  75                  80

Gln Ser Glu Ser Thr Gly Lys Val Val Thr Leu Met Ser Asn Asp Ala
             85                  90                  95

Gln Lys Val Gln Asp Ala Met Met Ala Ile His Thr Ile Trp Gly Ala
            100                 105                 110

Pro Ala Leu Ile Val Val Ile Thr Ile Leu Leu Tyr Gln Gln Val Gly
            115                 120                 125

Trp Ala Thr Phe Val Gly Leu Gly Ile Met Leu Ile Tyr Ala Pro Met
        130                 135                 140

Thr Gly Lys Val Ser Arg Lys Leu Val Val Leu Arg Arg Ser Ile Met
145                 150                 155                 160

Gln Trp Thr Asp Arg Arg Val Gly Leu Met Asn Glu Val Ile Asn Gly
                165                 170                 175

Met Gln Met Ile Lys Phe Tyr Ala Trp Glu Asn Ser Phe Lys Arg Gln
            180                 185                 190

Ile Leu His Ala Arg Asp Asn Glu Ala Arg Ile Leu Lys Thr Val Val
        195                 200                 205

Leu Trp Gln Ser Phe Phe Ala Met Leu Leu Phe Ser Gly Pro Val Ala
210                 215                 220

Val Ala Val Phe Cys Phe Gly Ser Trp Ala Leu Ala Gly Tyr Gly Leu
225                 230                 235                 240

Thr Ala Ala Ser Ala Tyr Thr Ala Leu Ser Leu Phe Ser Leu Leu Arg
                245                 250                 255

Met Pro Leu Val Met Leu Pro Met Met Ile Thr Met Ile Ile Asn Ala
            260                 265                 270

Leu Val Ala Leu Asn Arg Ile Ser Ala Phe Leu Leu Arg Gly Glu Ile
        275                 280                 285

Gln Thr Thr Ser Gln Pro Gly His Asp Gly Asn Ser Ser Lys Glu Lys
        290                 295                 300

Gln Glu Thr Val Gln Glu Thr Val Gln Glu Thr Val Gln Glu Thr Val
305                 310                 315                 320

Glu Pro Gly Val Val Arg Val Thr Glu Gly Thr Phe Ser Trp Asp Ser
                325                 330                 335

Ala Gly Asp Gln Ala Ala Leu Arg Asp Val Asn Phe Thr Ala Ala Pro
            340                 345                 350

Ser Ser Leu Thr Met Val Val Gly Ser Val Gly Cys Gly Lys Ser Ser
        355                 360                 365

Leu Leu Ser Ala Leu Ile Gly Gln Met Glu Lys Gln Gly Gly Glu Val
        370                 375                 380

Gln Leu Gly Gly Arg Val Ala Tyr Val Ala Gln Thr Ala Trp Ile Ile
385                 390                 395                 400

Asn Asp Met Val Gln Glu Asn Ile Leu Leu Gly Glu Ala Phe Asp Ala
                405                 410                 415

Asp Arg Tyr Arg Met Ala Val Glu Ile Ser Gln Leu Val Pro Asp Leu
```

-continued

```
                420             425             430
Glu Leu Leu Pro Asn Gly Asp Arg Thr Glu Ile Gly Asp Arg Gly Val
                435             440             445
Thr Leu Ser Gly Gly Gln Lys Gln Arg Val Ser Ile Ala Arg Ala Val
                450             455             460
Tyr Ser Asp Ala Asp Val Tyr Leu Phe Asp Asp Pro Leu Ser Ala Val
465             470             475             480
Asp Ser His Val Gly Arg Ala Leu Phe Glu Lys Cys Ile Arg Gly Val
                485             490             495
Leu Arg Asn Lys Thr Val Ile Leu Val Thr Asn Ala Leu Gln Tyr Leu
                500             505             510
Pro Ser Ala Asp Asn Ile Leu Trp Met Glu Gly Gly Ala Val Lys Ala
                515             520             525
Gln Gly Ser Tyr Ser Gln Leu Val Ala Ala Gly Met Asn Val Ala Glu
                530             535             540
Leu Val His Val Glu His Glu Ala Glu Gln Thr His Gln Arg Asp Glu
545             550             555             560
Asp Pro Ser Arg Gln Ala Gly Thr Gly Val Val Ala Glu Glu Ala Asp
                565             570             575
Leu Pro Asp Asp His Asp Ser Thr Gly Thr Ser Gly Thr Asp Ser Ala
                580             585             590
Tyr Ser Asp Asp Ile Ala Lys Ala Thr Ile Val Ser His Asp Asp Ala
                595             600             605
Asp Gly Asp Lys Ala Ala Arg His Val Lys Gly Ser Tyr Ile Pro Glu
                610             615             620
Gly Lys Pro Ser Lys Ser Ile Thr Leu Arg Lys Ile Asp Thr Val Asp
625             630             635             640
Asn Arg Asn Leu Thr Gly Ile Glu Ala Arg Glu Thr Gly Ala Val Ser
                645             650             655
Gly Lys Val Leu Lys Ser Tyr Ile Ile Ala Gly Gly Phe Ile Ile
                660             665             670
Ile Ala Phe Val Ala Leu Leu Phe Ala Ala Glu Gln Gly Ala Arg Val
                675             680             685
Phe Thr Asp Thr Trp Val Gly Leu Trp Phe Gly Asp Ala Phe Arg Gln
                690             695             700
Asn Val Trp Phe Tyr Val Gly Ile Tyr Ala Ala Leu Gly Ile Leu Tyr
705             710             715             720
Ser Phe Leu Thr Phe Leu Arg Ala Leu Arg Phe Asn Tyr Ser Ala Val
                725             730             735
Asn Ala Ala Leu Ser Leu His Asn Gln Leu Leu Asn His Ile Leu Arg
                740             745             750
Leu Pro Lys Ser Phe Phe Asp Thr Asn Pro Ala Gly Arg Ile Leu Asn
                755             760             765
Arg Phe Ser Arg Asp Thr Glu Ile Met Asp Ser Thr Val Ala Thr Ser
                770             775             780
Ala Leu Met Phe Cys Asn Cys Met Ala Thr Phe Ile Ala Ile Leu Ile
785             790             795             800
Val Ile Ser Val Ala Thr Lys Trp Phe Ala Val Ala Ile Ile Pro Ile
                805             810             815
Thr Ile Thr Tyr Met Leu Leu Gln Arg Tyr Tyr Ile Pro Ser Ala Arg
                820             825             830
Glu Leu Gln Arg Ile Glu Ser Val Ser Arg Ser Pro Ile Tyr Ser Lys
                835             840             845
```

```
Phe Ser Glu Ala Leu Ala Gly Val Pro Thr Ile Arg Ala Tyr Arg Lys
    850                 855                 860

Glu Arg Tyr Phe Thr Val Thr Ser Asp Lys Leu Met Gln Glu Asn Ala
865                 870                 875                 880

Tyr Ala Tyr Ile Ser Gln Arg Ser Ala Ala Ser Trp Leu Ala Met Arg
                885                 890                 895

Leu Asp Val Val Gly Val Leu Ile Leu Thr Leu Thr Gly Val Leu Cys
                900                 905                 910

Ile Gln Gly Thr Ile Ser Pro Gly Leu Ala Gly Leu Cys Leu Val Tyr
                915                 920                 925

Ala Leu Asp Leu Thr Arg Tyr Leu Lys Met Gly Thr Ala Met Ala Ser
    930                 935                 940

Lys Thr Glu Ser Asp Phe Asn Ser Val Glu Arg Ile Ile Gln Tyr Leu
945                 950                 955                 960

Glu Pro Ala Pro Glu Ala Asp Ala Asp Thr Pro Ala Asp Val Leu Ala
                965                 970                 975

Thr Leu Pro Ala Asn Trp Pro Ala Ala Gly Ser Ile Ser Val Arg Asp
                980                 985                 990

Val Cys Met Arg Tyr Arg Pro Gly Leu Pro Leu Val Leu Lys Gly Val
                995                 1000                1005

Ser Phe Asp Ile Ala Pro Gly Glu Lys Val Gly Leu Val Gly Arg
    1010                1015                1020

Thr Gly Ser Gly Lys Ser Ser Leu Phe Leu Ala Leu Phe Arg Met
    1025                1030                1035

Ala Glu Pro Glu Ser Gly Ser Ile Leu Ile Asp Gly Val Asp Ile
    1040                1045                1050

Arg Thr Leu Gly Leu His Thr Leu Arg Ala Ala Met Ser Val Ile
    1055                1060                1065

Pro Gln Asp Pro Phe Met Phe Ser Gly Thr Val Arg His Asn Leu
    1070                1075                1080

Asp Pro Phe Asp Glu His Pro Asp Ser Glu Leu Trp Arg Val Leu
    1085                1090                1095

Glu Ala Val Gly Leu Lys Thr Val Ile Ser Val Leu Glu Ala Lys
    1100                1105                1110

Leu Glu Ala Pro Val Val Asp Asn Gly Ala Asn Phe Ser Gln Gly
    1115                1120                1125

Gln Arg Gln Leu Phe Cys Met Ala Arg Ala Met Leu Arg Arg Ser
    1130                1135                1140

Arg Ile Leu Met Leu Asp Glu Ala Thr Ala Ser Val Asp Pro Glu
    1145                1150                1155

Thr Asp Ser Leu Ile Gln Ala Ala Ile Arg Ser Ala Phe Gln Glu
    1160                1165                1170

Cys Thr Leu Leu Thr Ile Ala His Arg Leu Asn Thr Ile Met Asp
    1175                1180                1185

Ser Asp Arg Val Leu Val Leu Asp Gly Gly Val Val Ala Glu Asn
    1190                1195                1200

Asp Gln Pro His His Leu Leu Gln Asn Asn Asn Gly Leu Phe Thr
    1205                1210                1215

Gln Met Val Asp Gln Thr Gly Lys Gln Ser Ser Thr Tyr Leu Lys
    1220                1225                1230

Gln Val Ala Arg Ser Ala Thr Thr Ser Arg Gln Thr Ala Arg Arg
    1235                1240                1245
```

Arg Met Ala Val Ala His His Asp Thr Ala Glu Ile Thr Asp Met
1250                1255                1260

Ala Gly Leu Arg Ser Glu Ser Thr Val Gly Val Val Pro Gln Leu
    1265                1270                1275

Ser Pro Thr Met Asp Pro Leu Gly Pro Ala Val Glu Ala Ala Pro
    1280                1285                1290

Ala Arg Leu Thr Thr Glu Val Ser Gln Leu Arg Arg Asn Ile Asp
    1295                1300                1305

Ala Gly Asp Val Ala Leu Thr Ser Pro Thr Val Ala Leu
    1310                1315                1320

<210> SEQ ID NO 4
<211> LENGTH: 636
<212> TYPE: PRT
<213> ORGANISM: Chromochloris zofingiensis

<400> SEQUENCE: 4

Lys Ala Asp Ala Asp Val Cys Ile Lys Asp Glu Thr Val Val Asp Met
1               5                   10                  15

Lys Arg Leu Glu Leu Asp Asn Gly Met Pro Gly Val Val Ser Gly Gly
            20                  25                  30

Ser His His Leu Pro Ala Lys Arg Gly Ser Ser Phe Gly Pro Ser Gly
        35                  40                  45

Met Thr Ile Ser Val Lys Asp Leu Thr Phe Ser Val Lys Ser Asn Ile
50                  55                  60

Glu Lys Gly Lys Thr Val His Leu Leu Lys Asn Val Thr Gly Phe Phe
65                  70                  75                  80

Glu Pro Asn Lys Met Ser Ala Leu Met Gly Pro Ser Gly Ser Gly Lys
                85                  90                  95

Thr Thr Leu Leu Asp Ile Leu Ala Gly Arg Lys Thr Ser Gly Lys Thr
            100                 105                 110

Glu Gly Thr Ile Leu Phe Ala Gly Asn Lys Pro Thr Arg Gln Phe Leu
        115                 120                 125

Arg Arg Tyr Thr Gly Tyr Val Glu Gln Phe Asp Thr Leu Leu Pro Thr
130                 135                 140

Leu Thr Val Glu Glu Met Leu Met Tyr Thr Ala Glu Leu Lys Arg Pro
145                 150                 155                 160

Ile Ser Glu Pro Leu Ser Glu Lys Lys Ala Ala Val Asp Glu Leu Ile
                165                 170                 175

Asp Lys Leu Ala Leu Glu Ser Cys Arg Lys Val Pro Ile Gly Ser Ser
            180                 185                 190

Met Ser Lys Gly Ile Ser Gly Gly Gln Ala Lys Arg Thr Asn Ile Gly
        195                 200                 205

Ile Ala Leu Ile Thr Asn Pro Arg Val Leu Phe Leu Asp Glu Pro Thr
210                 215                 220

Ser Gly Leu Asp Ser Phe Thr Ser Asn Glu Val Met Thr Val Val Lys
225                 230                 235                 240

Ala Leu Val Ser Asp Gly Val Thr Ile Val Ala Thr Ile His Ser Pro
                245                 250                 255

Thr Ala Tyr Ala Phe Asn Leu Phe Asp Lys Leu Met Met Leu Val Lys
            260                 265                 270

Gly Arg Val Val Tyr Phe Gly Ala Gln Gly Lys Pro Ala Leu Glu Tyr
        275                 280                 285

Val Arg Thr Gln Cys Pro Gln Ile Lys Glu Gln Ser Ser Gly Tyr Gly
290                 295                 300

Ser Asp Ala Glu Trp Leu Val Asp Leu Phe Thr Glu Ala Asp Arg Met
305                 310                 315                 320

Gly Lys Gly Gly Glu Phe Ala Asp Ala Tyr Asp Val Ser Gln Leu Lys
            325                 330                 335

Lys Asp Asn Asp Tyr Ile Val Asp Ser Leu Cys Ala Gln Lys His Val
        340                 345                 350

Leu Pro Ala His Val Gln Gln Glu Leu Ser Val Lys Thr Glu Thr Val
    355                 360                 365

Thr Pro Trp Trp Trp Gly Ile Lys Thr Leu Ile Lys Tyr Arg Thr Thr
370                 375                 380

His Asn Tyr Arg Asp Ala Ala Phe Leu Gly Pro Arg Ile Gly Asp Lys
385                 390                 395                 400

Leu Leu Ile Gly Leu Leu Ile Met Thr Leu Tyr Leu Gly Ile Gly Asp
            405                 410                 415

Asp Phe Ala Pro Asp Asn Val Ile Asn Ile Ala Ala Val Asn Phe Met
        420                 425                 430

Phe Val Thr Met Pro Ala Phe Gly Ala Ala Tyr Val Pro Ala Ile
    435                 440                 445

Val Leu Glu Arg Asn Leu Phe Cys Arg Glu Arg Asn Asp Gly Val Tyr
450                 455                 460

Arg Val Ile Thr Tyr Leu Met Ala Lys Met Leu Asp Glu Leu Met Ile
465                 470                 475                 480

Ala Ala Val Ala Ser Cys Val Ile Ala Ile Ala Phe Tyr Gly Ile
            485                 490                 495

Gln Leu Gln Gly Glu Phe Val Leu Phe Trp Leu Val Tyr Tyr Ile Val
        500                 505                 510

Leu Cys Thr Gly Ile Val Leu Ala Tyr Phe Val Ala Ala Leu Ser Pro
    515                 520                 525

Asn Met Asp Val Ala Asn Ala Ala Leu Pro Thr Tyr Val Thr Ser Leu
530                 535                 540

Leu Phe Phe Gly Gly Phe Leu Phe Thr Phe Asp Lys Met Pro Val Trp
545                 550                 555                 560

Trp Lys Trp Tyr Ser Tyr Ile Asp Val Ile Arg Tyr Ala Trp Thr Ala
            565                 570                 575

Ile Met Val Asn Gln Phe Glu Gly Arg Asp Ala Gln Met Phe Ser Gly
        580                 585                 590

Gln Thr Val Leu Gln Tyr Tyr Gly Ile Glu Gly Gln Asn Lys Trp Ala
    595                 600                 605

Asn Leu Gly Tyr Thr Ala Cys Phe Phe Phe Phe Thr Phe Cys Ala
610                 615                 620

Trp Val Thr Leu Ser Val Lys Lys Tyr Gln Arg Arg
625                 630                 635

<210> SEQ ID NO 5
<211> LENGTH: 767
<212> TYPE: PRT
<213> ORGANISM: Chromochloris zofingiensis

<400> SEQUENCE: 5

Gln Leu Gln Phe Thr Asn Gln Val Gly Gln Ala Arg Leu Arg Ala Ala
1               5                   10                  15

Val Pro Arg Pro Gly His Lys His Ala Gly Val Arg Ala Arg Pro Phe
            20                  25                  30

Gln Ala Ala Lys Pro Gly Cys Arg Pro Pro Thr Ile Leu Ala Ser Ser

```
                35                  40                  45
Ala Ala Leu Ser Ser Ile Asp Tyr Thr Tyr Ser Ser Ser Val Ser Asp
 50                  55                  60
Ala Lys Ser Arg Pro Phe Pro Ala Val Ala Pro Leu Pro Ser Pro Pro
 65                  70                  75                  80
Arg Thr Ala Asp Leu Gly Asn Val Leu Pro Tyr Leu Ala Lys Leu Ala
                 85                  90                  95
Val Gly Glu Arg Gln Leu Leu Trp Arg Phe Gly Val Ala Leu Ile Cys
                100                 105                 110
Met Val Thr Ser Lys Leu Ala Gly Leu Ala Gly Pro Val Leu Leu Arg
            115                 120                 125
Glu Ala Val Asn Ala Val Gly Glu Gln Ala Thr Ala Ser Leu Arg Pro
            130                 135                 140
Ala Val His Ala Val Val Cys Tyr Gly Leu Cys Gly Val Leu Gly Thr
145                 150                 155                 160
Leu Ala Lys Glu Leu Gln His Pro Thr Phe Ala Pro Val Ser Gln Ala
                165                 170                 175
Val Ala Arg Arg Val Ala Tyr His Thr Phe Ala His Val Leu Asp Leu
                180                 185                 190
Asp Ile Lys Phe His Leu Glu Arg Arg Thr Gly Arg Leu Ser Arg Ile
            195                 200                 205
Leu Glu Arg Gly Thr Arg Ser Val Gln Met Leu Tyr Arg Ala Val Leu
210                 215                 220
Phe Thr Phe Ile Pro Thr Ala Leu Glu Phe Ala Phe Val Ile Gly Leu
225                 230                 235                 240
Leu Gly Thr Gln Phe Ser Ser Thr Val Ala Gly Leu Val Ala Val Thr
                245                 250                 255
Phe Val Ala Tyr Val Ala Trp Thr Leu Ala Met Thr Gln Ser Ala Val
                260                 265                 270
Glu Val Arg Lys Gln Val Asn Thr Leu Asp Asn Leu Thr Thr Ser Lys
            275                 280                 285
Ala Val Asp Ala Leu Leu Asn Ala Glu Thr Val Thr Leu Phe Asn Asn
            290                 295                 300
Gln Ala Leu Glu Val Gln Gln Tyr Asp His Tyr Leu Arg Gly Phe Gln
305                 310                 315                 320
Arg Ala Ala Ile Gln Thr Glu Arg Leu Ser Ala Leu Leu Asn Ala Gly
                325                 330                 335
Gln Ser Ala Ile Leu Thr Ile Gly Leu Met Leu Val Leu Ile Ala Ala
            340                 345                 350
Leu Val Ser Ala Pro Ala Thr Arg Pro Val Thr Ala Gly Asp Leu Val
            355                 360                 365
Leu Leu Gln Gly Leu Leu Leu Gln Leu Trp Ser Pro Leu Gln Phe Leu
            370                 375                 380
Gly Trp Phe Tyr Arg Glu Leu Arg Gln Ser Leu Val Asp Met Glu Glu
385                 390                 395                 400
Phe Phe Glu Ile Leu Gln Thr Gln Ser Gln Leu Pro Asp Gly His Leu
                405                 410                 415
Ser Leu Pro Asn Thr Pro Pro Cys Met Val Arg Asn Ile Ala Ala Gln
                420                 425                 430
Thr Ser Asn Ser Thr Ser Arg Asn Gly Asn Ser Ser Gln Arg Leu Gly
            435                 440                 445
Ser Asn Thr Val Ser Ser Thr Gly Thr Ser Pro His His Ser His Ser
            450                 455                 460
```

Gln Gln Gln Gln Gln Pro Asp Asp Pro Thr Ala Ser Tyr His Glu Ile
465                 470                 475                 480

Pro Tyr Asp Ala Ala Cys Ile Ser Gly Phe Gly Leu Glu Val Glu Leu
            485                 490                 495

Lys Asp Val His Phe Gly Tyr His Pro Asp Arg Gln Val Leu Arg Gly
        500                 505                 510

Val Thr Leu Arg Ile Pro Pro Gly Gln Ser Val Ala Ile Val Gly Ser
            515                 520                 525

Ser Gly Ser Gly Lys Ser Thr Ile Leu Lys Leu Val Thr Arg Leu Tyr
        530                 535                 540

Asp Val Thr Thr Gly Ser Val Glu Val Asn Gly Val Asp Ile Lys Asp
545                 550                 555                 560

Leu Thr Arg Asp Ser Leu Arg Ala Ala Val Ala Val Pro Gln Asp
                565                 570                 575

Thr Val Leu Phe Asn Asp Thr Ile Leu Gln Asn Ile Arg Tyr Gly Arg
            580                 585                 590

Pro Glu Ser Thr Asp Asp Glu Val Ile Arg Ala Ala His Leu Ala His
        595                 600                 605

Leu His Asp Ala Val Val Lys Met Pro Glu Gly Tyr Lys Thr Val Val
    610                 615                 620

Gly Glu Arg Gly Leu Lys Leu Ser Gly Gly Glu Lys Gln Arg Val Ala
625                 630                 635                 640

Ile Ala Arg Ala Phe Leu Arg Ala Pro Arg Leu Leu Ile Cys Asp Glu
                645                 650                 655

Ala Thr Ser Ala Leu Asp Ser Ala Thr Glu Ala Ser Ile Met Asn Ser
            660                 665                 670

Leu Asn Glu Leu Ala Gln Gly Arg Thr Ser Leu Phe Val Ala His Arg
        675                 680                 685

Leu Ser Thr Ile Arg Asn Cys Asp Arg Ile Val Val Leu Ser Ala Gly
    690                 695                 700

Val Val Val Glu Glu Gly Thr His Asp Gln Leu Met Ser Arg Gly Ala
705                 710                 715                 720

Val Tyr Arg Asp Met Trp Glu Met Gln Ala Lys Glu Ala Ser Arg Gly
                725                 730                 735

Asn Gly Val Ala Glu Gly Thr Thr Ser Asp Ser Glu Asp Gly Glu Arg
            740                 745                 750

Thr Met Glu Pro Leu Pro Ala Ala Leu Thr Ala Lys Ser Leu Asn
        755                 760                 765

<210> SEQ ID NO 6
<211> LENGTH: 557
<212> TYPE: PRT
<213> ORGANISM: Chromochloris zofingiensis

<400> SEQUENCE: 6

Met His Thr Ser Ser Thr Leu Tyr Pro Leu Gly Ile Ile Ser Phe
1               5                   10                  15

Leu Val Ile Val Val Pro Leu Val Met His Val Leu Ser Ser Arg Arg
            20                  25                  30

Leu Asp Leu Asp Leu Leu Pro Ser Pro Ala Val Leu Leu Leu Gly
        35                  40                  45

His Ile Gln Leu Ala Leu His Val Lys Asp Met His Leu Gln Phe Leu
    50                  55                  60

Arg Trp His Asn Arg Phe Gly Lys Leu Leu Arg Ile Arg Val Leu Gln

-continued

```
                65                  70                  75                  80
Gln Asp Met Val Leu Ile Ala Asp Pro Ala Leu Ala Ser Glu Val Leu
                    85                  90                  95

Thr Leu Gly Pro Asn Tyr Cys Ala Arg Arg Pro Ala Asp Tyr Ala Thr
            100                 105                 110

Phe Asn Val Ile His Gly Leu Ser Ala Arg Pro Ser Ile Leu Thr His
        115                 120                 125

Gln Asp Glu Ala Trp Trp Lys Ala Val Arg Arg Ala Ile Ala Pro Ala
    130                 135                 140

Tyr Thr Pro Ala Ala Thr Arg Glu Leu His Ser Leu Met Val Ser Thr
145                 150                 155                 160

Met Ala Arg Val Cys Glu Arg Ile Asn Ala Asn Leu His Ser Ala Ala
                165                 170                 175

Asn Asn Gly Asn Ser Thr Ser Thr Ser Ser Asp Ser Thr Gly Ser
            180                 185                 190

Pro Ala Gly Ile Arg Met Asp Glu Glu Val Leu Val Ala Val Leu Glu
        195                 200                 205

Ile Leu Leu His Gly Ser Leu Arg Leu Pro Pro Gln Ala Met Ser Ser
    210                 215                 220

Ser Asp Val Arg Arg Thr Ala Gln Val Ala Pro Lys Leu Val Thr Ile
225                 230                 235                 240

Ala Asn Ser Phe Val Ser Leu Pro Gly Lys Gln Trp Val Tyr Thr Thr
                245                 250                 255

Leu Pro Phe Ile Cys Lys Glu Ala Arg Val Met His Gln Gly Arg Thr
            260                 265                 270

His Met Thr Asn Ile Thr Arg Gln Ile Tyr Asn His Ile Ser Ala Lys
        275                 280                 285

Tyr Thr Val Asn Gly Val Pro Ser Ala Lys Ser Asp Val Gly Gly Ser
    290                 295                 300

Glu Lys Ser Asp Thr Ser Leu Ala Ser Cys Leu Met Arg Leu Ala His
305                 310                 315                 320

Pro Gln His Thr Pro Gly Gln Thr Phe Thr Gln Asp Ile Met Ala
                325                 330                 335

Glu Ile Ala Ile Asn Ile Ile Gly Gln Gly Ser Val Pro Trp Thr Val
            340                 345                 350

Ser Trp Ala Leu Phe Gln Leu Thr Gln Arg Pro Asp Val Glu Ser Arg
        355                 360                 365

Leu Leu Ser Glu Leu Gln Gly Leu Gly Leu Pro Cys Asp Gly Asp Leu
    370                 375                 380

Ala Ala Ala Cys Asp Ala Ile Ser His Pro Glu Cys Leu Arg Asp Thr
385                 390                 395                 400

Pro Tyr Leu Thr Ala Val Ile Asn Glu Val Met Arg Met Tyr Pro Ala
                405                 410                 415

Gly Val Ser Ala Ala Pro Arg Leu Thr Glu Gln Pro Ile Lys Leu Gly
            420                 425                 430

Gly Tyr Arg Ile Pro Ala Gly Val Met Val Phe Pro Asn Leu Phe Thr
        435                 440                 445

Ile Met Asn Tyr Arg Gly Asn Trp Gln Gln Pro Asp Gln Phe Tyr Pro
    450                 455                 460

Asp Arg Trp Leu Gln Pro Asn Ser Ser Val Asp Pro Ser Ser Gly Ala
465                 470                 475                 480

Pro Arg Phe Ile Pro Phe Ser Ile Gly Pro Lys Ile Cys Ile Ala Gln
                485                 490                 495
```

His Leu Ala Ile Met Gln Cys Lys Ile Met Leu Thr Leu Leu Val Ser
            500                 505                 510

Cys Leu Lys Phe Gln Leu Ala Pro Thr Met Gly Gly Ile Glu Gly Val
        515                 520                 525

Met Lys Arg Val Glu Ala Thr Leu Glu Leu Arg Val Gln Gly Gly Leu
    530                 535                 540

Trp Phe Thr Ala Glu Ile Arg Arg Ser Asn Asn Val Lys
545                 550                 555

<210> SEQ ID NO 7
<211> LENGTH: 246
<212> TYPE: PRT
<213> ORGANISM: Chromochloris zofingiensis

<400> SEQUENCE: 7

Asp Gly Leu Ala Ile Ala Met Gly Cys Ala Ala Val Leu Val Cys
1               5                   10                  15

Tyr Thr Val Leu Pro Phe Leu Cys Ser Leu Ala Leu Ala Ile Trp Arg
            20                  25                  30

Phe His Thr Ser Lys Ile Pro Gly Pro Pro Ala Lys Asp Phe Ile Leu
        35                  40                  45

Gly His Ala Ala Ala His Leu Asn Asp Lys Ala Pro Phe Ile Phe Lys
    50                  55                  60

Arg Trp Ala Glu Lys Tyr Gly Lys Leu Tyr Lys Val Arg Met Ala Asp
65                  70                  75                  80

Asn Phe Ala Val Val Leu Thr Asp Pro Glu Val Ile Gln Ser Ile Ala
                85                  90                  95

Arg Lys Ile Gln Lys Pro Thr Lys Ser Tyr Ser Ser Leu Glu Leu Gly
            100                 105                 110

Thr Phe Pro Lys Asp His Asn Ile Leu Thr Ala Pro Asp Gly Pro His
        115                 120                 125

Trp Lys Ala Val Arg Gln Gly Ile Thr Pro Ala Phe Ser Val Ala Asn
    130                 135                 140

Leu Lys Gln Val Phe Pro Trp Leu Cys His Val Thr Lys Val Ala Ala
145                 150                 155                 160

Ala Lys Leu Gln Asp Thr Gly Pro Ser Thr Ser Phe Asp Ile Ser Asp
                165                 170                 175

Ile Ala Lys Arg Ile Thr Ser Asp Val Ile Gly Gln Leu Leu Tyr Ala
            180                 185                 190

Glu Asp Leu Gly Ala Ile Ala Tyr Arg Pro Ser Glu Tyr Leu Glu Leu
        195                 200                 205

Phe Gln Ile Gly Ile Thr Ala Ala His Lys Ser Leu Gly Arg Pro Leu
    210                 215                 220

Arg Leu Tyr Ala Ile Trp Asp Pro Glu Val Arg Arg Gln Asn Arg Ala
225                 230                 235                 240

Ile Asn Arg Leu Asp Gln
                245

<210> SEQ ID NO 8
<211> LENGTH: 2940
<212> TYPE: DNA
<213> ORGANISM: Chromochloris zofingiensis

<400> SEQUENCE: 8
atggaagcag cactgaccac tgccgtagat gcagcggcag cgttacgaaa caacataggc    60

-continued

| | |
|---|---|
| ttcttgcaaa gaagccagat agcaatcgta gcagcgttcc tgtcagcaat atacctcaaa | 120 |
| ctggttgtgt caaggatagc acctggctgg aaaagcttag cacttgtggc tccgctgctt | 180 |
| gcattgaacc tgtggctccc gctactcttt catatgagag aggaggtcgt cagcaggact | 240 |
| tgcgtggtat tcctaatatc ttggctcggc agcttcaagg tagcagtaag cataatgatg | 300 |
| tagctgttaa cgcagcaaga ctggcctgca tgcacaattg tgtggtcagg cacaccgacc | 360 |
| atagccagca gccacagcac aaccacatca gcttgtatgt atgtatgttc aatgaatgta | 420 |
| tgcatgcatc acatctagag cgcaacgtcc tcaagtacct taagttagct catgctcaga | 480 |
| atcgtgacat gtctggtgct gcaacttgcc agcagttgca ccaatgatga tgatgataat | 540 |
| ggtcatacct ggttggcatt attgtgaagc catcacacat gcatgctatc attgcaggca | 600 |
| attggtatgt gcctcaatag ggggccactg gctgctgatt ggagtgtagc acagatgatc | 660 |
| ttcctgtatg ttgcaccagt actaccccga caaggtacat ggcatggcag acacaggtcc | 720 |
| ttagttgtg gtgttgcttt tctcgttgct tacgaagcag tatgcaggaa cttaagttat | 780 |
| tgacatgcaa cacccagcaa caacagggca agaagtagga tgcttgtgaa tgcatgtcgg | 840 |
| cattttccaa tgcctctgtt ctgaactgtg gcggatgcgg accgtgcatc caccctgatg | 900 |
| aatttcagcc ctctgtctct cactctgatt ggcatatact gacacatgtg ttgtgctcct | 960 |
| gtgtcatatg cagatgctgg cggccctgtc aaagcaggcc ggctgcagga cagtgctggc | 1020 |
| acctggggaa ctcttgcggc atcatttgtg atcaacacca gtaagtaggc gccacaagca | 1080 |
| gtacatgcca gactgagagt tgaggctgcc ctctttacac agcattcctg gctcatggtg | 1140 |
| ctgtggctca ttgcaacaca actgcatcat atgacatgct gcttctacac attgtcctta | 1200 |
| cacaatggcg ccagttgttg ttgtgtgctc caccgcccat cagttgtgat gagctgaata | 1260 |
| gcgactgaca ataaccactt gcttggtgct gcttgcagca attcttggtg ttgtttctta | 1320 |
| cctactggtg gtgatggaca tgccaaaagt agtcaagata tacatctacg gtgcgcaagg | 1380 |
| cagcccacat agttgctgta atccactacg catcataact gtctatgtgt gtgtcatagg | 1440 |
| aaacttgctg ctgcgttatg acctgtagct gtcatacatt ggcagtagtt gttaccctct | 1500 |
| tgtgtgtgct tgagcgtggt cataagtcat ggtttgcatg ccagatgac atcagcttct | 1560 |
| gcccaggaat actgcatctg cctgccatcc gctacaacat tgctaaagtt gatactgaac | 1620 |
| ctgtctgtga tcctctacca tcctctacct tgcagcattg ggtttatatg gctttgtctc | 1680 |
| gtttattatg gagggtccag cagccatcat tgtgggcttg ctgaggatcg aacttgtgcc | 1740 |
| tcccttgat aaaccatggc tggtaagtgg ctgacataga cccaaagcaa agcagtaagg | 1800 |
| ccatgaggcc cttaaggcat ggaggtgtgc acagtggaca gttttgcaca cttgtctgaa | 1860 |
| acagttgagc ttcactatgg tccttgtgaa ggagctgagt ggcttgtgca tgttgcgtaa | 1920 |
| aggtagccac tgtgtctact aacactgacc ttcatgttaa aatacatacg tgtgttgtgg | 1980 |
| tgatggtgac gttgatgctg ccgctgcggt gctgatattg ttcttttttcc tgttccacgc | 2040 |
| aggcgactag tttagctgac ttctggggtc ggcgttggaa caactccact agtttgttac | 2100 |
| tacggttcct ggtgtatgat cccatcattg aaggcaggtt ggtgaagaag gccaaacaag | 2160 |
| aggatccaca gcaacctgct ccaagcaagc aagtcagcaa cagcatgagg ctgactgcca | 2220 |
| tgcttgctac gtttgcattg agtgggctga tccatgaagc catcttggcg tatgtgaatc | 2280 |
| ggccatacta cccaggaccc tggttcatgt tcttcttcat tcaggtgagc ctggtgctga | 2340 |
| atgattgata gtagatgcat aatcaatgat tgaggcacac tgatcttagg ccgtggtcat | 2400 |
| cgttgcaata caacattact gcatgtcgtt atgtggcata cttcttgttg ttggcagtgc | 2460 |

```
aacacctcag gggtggtcaa ctggccttgg gcattacagc cttgcagaca tgggtatgac    2520
aatcacacgg ttgatggtaa attgttgtct tgtaaccacg catgactcct catttggcaa    2580
gtgcccatct gggcaccact gttataccgc ttggtttgtg caactgttgt cttggctgat    2640
ttgtcgacat gttgatcatt gcaggggccc ttgttggcag tggagatgcg ggtacacaag    2700
catctgaggg caacacacaa gcagctgcca ttcactgctg catggacctt gacaacagca    2760
tgtctgctgt taacagctta catgttttct tccctccca tcgaagactg gacagacctt     2820
gcaccaagaa tagctcaagc agtcaccagc aacttccaag cagtgttagg cccgcttcag    2880
gggctggggc gccagtactg ggctgtagca gctgggttgg tgcaacagtc agccatttga    2940
```

<210> SEQ ID NO 9
<211> LENGTH: 1891
<212> TYPE: DNA
<213> ORGANISM: Chromochloris zofingiensis

<400> SEQUENCE: 9

```
atgccggtac ctgtgtccac aacccaccca aatggcaagg gaatgcgcgc agccaacctc      60
acggagttac ccacagaggg gccttttca cgatcgctga agcagaaaga ggatagtgcc      120
aacacaggag cagatgcaat agcattgcaa acaaacggca ctgctgacgc ctcgcttgat     180
gccaatgcac catcaccatt gccagagccg ggaccatcag tgctggttca tcatctagac     240
ttcacatacc cagggttagg tgggtgcctg ccacattgtc atcattggca acaggcaacc     300
gaatgtatct ttcacagtca catacatact gcaaggtgtt tatgagtccc acagacatca     360
gacgtgctgg tgcattgtac cctgtgccca attcatcaaa gtgcatgtgc actttagcaa     420
gagggatggg tattttcaca gatgctttgt acactcattg catgctctgt gtttgcagat     480
ggccgccctg tgcctggtca acctcctctg ataaccgaca tgtgcctgac gctacagccg     540
ggcagcaggt gcttgctgat tggcgctaac ggtgcaggca aaacaacgct gctcaaaata     600
ctgggtggca agcatatggt acccaaggat gctgttcata tactgggtgc accacccttc     660
catgacacac atctccaccac atcagggcac ctgtcataca ttggtggtaa ttggactcgt    720
gatattgcat tcgcaggatt aagcataccg ctaacggtga gcacaaatcc agataactgt    780
tttgtatttg tgtatgttat caccaaagct gaactgacac cacagttgct taaacagcag    840
tgcatggtgc ctggttgccc tactttgatg cctgggccat agtacttcca tatcccatct    900
tctcactgct gcaaagaagc ttgcttttgt tcctttatgg gttcagagca aagcagcttc    960
tgacaaccat tgttttaacc atgtgtttgt cagtttatga ttttgggttt gtagataatg    1020 ggtaaaacctt ttttgttttt gctgacccac tacatggtgg ctgcagggtg acttccctgc   1080
ttcacggatg attgatgcca tcccagaggt tgaccccgca cgtaaagaac gcctgatcaa    1140
ggtgctggac attgatccaa actggcgcat gcatacggtg tcagatggtc aaagaaggcg    1200
tgtgcagatc tgtgttgggt tgttcgcgcc attcaaggtg gggcttctga tggtgacaat    1260
ctttatgtca gcagctacca ccaagtaaat tgccaagctg ttggttgcgt atcaaacagg    1320
ctgggcagga cttctatgcc tacccccttg cttgctgcgc agctgggttg atatgaagtg    1380
caagtgtgca tgcatggtgt accgaacagt tcttggatgt ggcagccaac gctgaacggg    1440
tatatacttg catggctgcc tgatgcaggt gctgcttctg gatgagatta ccgtggacct    1500
ggatgtgctt ggtagggctg atctgatgca tttcctggct gatgaatgcg ccaccagagg    1560
agctagcatc atatatgcca cacacatatt tgatggtctg gagttttggc ccacacatgt    1620
```

| | |
|---|---|
| agcatatgtt gcaagagggc ggctgcagat ggtcaagtca gctgaggaga tatctgagct | 1680 |
| caagcagggc aggttgttag agcttgtcac cagcctgttg agggaggaac gcgaggcagt | 1740 |
| gaaagctgct ggcgtcagta aaccactgga gtatgatccc agtctagaag gacaggttac | 1800 |
| aaacttctca tatgccttca ataatggttg ggttcctgga acgttgagca cctccttggc | 1860 |
| caagagtact aatgctgtga tgcgtaattg a | 1891 |

<210> SEQ ID NO 10
<211> LENGTH: 6808
<212> TYPE: DNA
<213> ORGANISM: Chromochloris zofingiensis

<400> SEQUENCE: 10

| | |
|---|---|
| atgcttcaga ggatagtagg cgggcttcaa tgctacgcaa ggcagcaggc tgtaccgtcc | 60 |
| gtgcagtgtc ctgagaacgc ctatttgtac tagtaagtgc agagggagac ttattctcgc | 120 |
| tgcagctgca tgcattggct agcagcactg tcgcatgcat ggtgcatgta tggtgtgctc | 180 |
| atgcgtgtat gacgcacatg catgagcaca ttccttacgg ggagcccatt tccatgtgta | 240 |
| ggctgtcaat gttgtgtcat gctctggtta catgattgct gatgctaggg tatctgtcag | 300 |
| ctgtgccatg catgcttatg ctagcatcac tgctgctgta actattacca tacatggttg | 360 |
| cattacatct cttgctgtgt ttgtgcagtt ggatcatagg tctgtcgtta gcacctttac | 420 |
| tacagagctt agcagaaaac tccatgaatt ttgagctcag cgtcatcggc acacgcatgc | 480 |
| gcaatggact gatggcagcc atataccgca agtgtctgcg gttgtccaac tcagccatac | 540 |
| agagtgagag caccggcaag gtggtcacac ttatgagtaa tgatgctcag aaggttcaag | 600 |
| atgccatgat ggccatccac accatctggg gtgcacctgc cctcattgtg gtcattacca | 660 |
| tactgttgta ccaacaagtg ggatgggcaa cctttgtggg actaggaatc atgcttatct | 720 |
| atgcacccat gacaggtgag ggcaccggga attagtgctg cctgcttcat gttaaggtac | 780 |
| cccagatgta tcctacatgt gccatggaat gcggtctggc agtaacgtct ggcagtaacc | 840 |
| caagaggtta tcgttaccat acgcccaaac atgcatgtgc aaaccgtgtt gatgtctgtg | 900 |
| ttgcaggcaa agtgtcacgg aagctggtgg tactgcgtcg cagcatcatg cagtggacag | 960 |
| atcgccgcgt gggcctcatg aatgaggtca tcaatggcat gcaaatgatc aagttctatg | 1020 |
| cctgggagaa ctccttcaag aggcagatcc tgcatgccag agacaatgaa gccagaatcc | 1080 |
| tgaagactgt ggtgttgtgg cagtcatttt ttgcaatgct cctgttcagc ggccctgtgg | 1140 |
| ctgtagcagt attctgtttt ggttcctggg cattagctgg ctatggcctg acagcagcgt | 1200 |
| cagcctacac agcactgtca ctgttcagtc tgttgcgaat gcctcttgtc atgttgccta | 1260 |
| tgatgattac catgatcatt aatgcactgg tggccctgaa ccgcatcagc gcgttcttgc | 1320 |
| tgcgtggcga gatacagacc accagccagc caggtcatga tggcaacagc agtaaagaga | 1380 |
| aacaggagac tgttcaggag actgttcagg agactgttca ggagactgtt gaacctggag | 1440 |
| tggtgcgggt acgttgtgta gtgctgctat aatcagctgc ttaattctgg agtggcaatg | 1500 |
| tgaactcact gatatcagtc tgttgattgt ggtctgtgaa cttttgaacaa tgttgtggtg | 1560 |
| tggctggcat catccaaggt acctgtttta cagctttgca gccacatcca cagccacaat | 1620 |
| gtgagtttgt tgtatgttgc agtgttccgt ggatgtgtgt gtggaccaaa gtagtcacac | 1680 |
| atgtctaagt cagtctcaaa cactgctgtc gtcaggtgac tgagggggacc ttcagttggg | 1740 |
| actctgctgg cgatcaggca gccctgcgtg atgtcaactt cactgctgcc cctagttcat | 1800 |
| tgaccatggt ggtgggcagt gtggggtgtg gcaagagcag tctgctgtca gcattgattg | 1860 |

```
gccagatgga gaagcaagga ggagaggtgc agcttggagg cagggttgcc tatgttgcac   1920
aaacggcatg gatcatcaac gacatggtgc aggtgggtgt ggctggccac cttgtgcacc   1980
ttctttgatt cagcaaagca aagcaatgtt acagccttat cccatggtcc actctcttgg   2040
ttacctagta atggtatgcg cgtatggcaa tacaagtgcc atacaaaggg ccccacataa   2100
tctatgttgg tcatgtgttc gttctgatca gcttgagctg ttgtggttgc taggagaaca   2160
tccttttggg tgaagcattc gatgctgatc ggtaccgtat ggcagtggag atctctcagc   2220
tagtgcctga cctagagcta ctgccaaatg gtgatcgcac agagattggc gaccgcggcg   2280
tcaccctgtc cggggggccag aagcagcgtg tgtcgattgc aagggctgta tacagtgatg   2340
ctgatgtgta cctgtttgat gatcctctca gtgctgttga ttcccatgtg ggtcgagcac   2400
tgtttgagaa gtgcatacgg ggtgtcctgc gcaacaagac agtcatcctg gtgactaatg   2460
ccctccaata tctgccctct gcggataata ttttgtggat ggaaggtggt gctgtgaagg   2520
ctcagggcag ctacagccaa ttggtggccg ctggcatgaa tgtggctgag ctggtacatg   2580
ttgagcatga agctgaacag acacatcagc gggatgagga ccccagcagg caggcaggca   2640
cgggtgtagt agcagaggag gctgaccttc ctgatgatca tgacagtaca ggcacgtctg   2700
gcactgactc agcttacagt gatgacattg ccaaagctac catcgtttct catgatgatg   2760
ctgatggtga taaagcagcc aggcatgtga aggggtccta catcccagag ggaaagccat   2820
caaagtccat cacgctaagg aagatagata ctgtagacaa caggaatctg acaggtattg   2880
aggctcgtga cgggcgct gtgagtggga aggtgctcaa gtcatacatc atcgctggcg   2940
gcggcttcat cattatagcc ttcgttgcgc tattgtttgc tgctgagcag ggtgcccgtg   3000
tgttcacgga cacttgggtt gggctctggt ttggtgatgc gttcaggcag aatgtgtggt   3060
tctatgtggg tatctatgca gcactgggaa tactgtacag tttcctcact ttcctcaggt   3120
aggtaaaagt cgatctgttg ggcagtattc acatgctgtc atttgttgct ttgtattttg   3180
actttgaact tgagcgtggt tcactgctgg tactgttgac tgcataaaag gtgctgatgt   3240
atgtttcttc tggcgtgcat ggcccattca gtgtcttgtt ggtgttgctg cagtgtctgg   3300
tcagtctttg ctgtgtgaaa gaccatgcat atgtcggcag ctgcctccaa gtgtcttccc   3360
ttggaacctt tgtgtgtagg gcacttcgtt tcaactactc agccgtcaat gcagccctgt   3420
ctctccacaa ccagctgttg aatcacatcc tgcgcctgcc caaatcattc tttgacacca   3480
acccagctgg cagaattctc aacaggttca gcagagacac tgaaatcatg acagcactg   3540 ttgctacatc agcgctcatg ttctgcaact gcatggcgac attcatcgcc atcctgattg   3600
tgatcagtgt tgcaacgaaa tggtttgctg tagccatcat ccctatcacc atcacataca   3660
tgctactgca ggtgagcagc gtgtcgcaaa ttgcagtttg tttatgtgca tgtcactgtg   3720
tgcttgttgg catgcaggta cagtgtattg tgtttgcagt gccgtgcact tgcagtgaga   3780
caatcatatg tctgcaaaac aagctgtagc gctggaattg ttttctaact cagccgttct   3840
tgttgttgtc ctgcagcggt attacatccc atccgctcgt gagctgcagc gcattgaaag   3900
tgtgtcccgc agtccatct acagcaaatt cagtgaggcg ctggcaggcg tgcccaccat   3960
cagggcttac aggaaggagc ggtactttac agtcaccagt gataagctga tgcaggaaa   4020 cgcatacgct tacatcagtc agaggtctgc agcttcatgg ctggccatga gacttgatgt   4080
tgtgggtgtg ctcatcctga cattgacagg tgggtggcag gagtgcctgc acatgtctag   4140
cttcacttgt agcttgcttg ctggcagttg ttacagtgtg cattgctgct gcagcttggg   4200
```

-continued

```
ttctgatgac tgttgcacta tgtttgctgg cggcaccctc tacctgtatg ctagttttg      4260 tttgagatgg ttgctgttgg tatatggata caccagcagt caggatgaac tgcagagctg     4320
ttatcctccg gcgttggttg taagtgtgct acatatgacg tgttttgctg acaaagacga    4380
ttgctgttgt tccgccaggt gtgttgtgca ttcaaggcac catcagcccc ggcctagcag    4440
gtctgtgcct ggtgtatgca ctggacctga cacgctacct gaagatgggc acggcaatgg   4500
catccaagac agagtctgat ttcaacagtg tggagcgaat cattcagtac ctggagcctg   4560
cacctgaagc tgatgctgac acacccgcag atgtgctggc cacactgcca gccaactggc   4620
ctgctgctgg cagcatcagc gtgagggatg tgtgcatgcg ctaccgccct gggctacctc   4680
ttgtgttgaa gggcgtcagt tttgacattg cgcctggtga aaggtgggg ctggtgggca    4740 ggacaggcag tggcaagagc tcactgttcc tagcactgtt caggtgagca tcatagaggg   4800
gacgacaccg gcagcagcag cagaggcatg gcacaaactg ggagttatgt gattgcttgt   4860
tgctatgtat catcgcatac atttccaaca gacaaccgat gttgtgtgcc ggactgtgtt   4920
ggtaacgttt gcttaagtgc cacaggtcct tctacttgca acttgtacac tcctgggact   4980
gttgtgtttt taaccacacc atagcccaca gtgtactgcg tgttgttgca tcttcgcctc   5040
acttgctggt tcttgcattg tgtaggatgg ccgaaccaga gtctggcagt attctgatcg   5100
atggtgttga catccgtacc cttggcctgc acacactgcg tgctgctatg tctgtcatcc   5160
ctcaagaccc cttcatgttc agcggtactg tgcggcacaa cctggatcca tttgacgaac   5220
atcctgacag tgagttgtgg cgcgtgctag aagcggttgg gctgaagaca gtcatatctg   5280
tactggaggc aaaactagaa gctcctgtgg tggacaatgg tgccaacttt tcacaggtaa   5340
attgtagctg ctgattgaca aggcattgac agggtttgaa atccatgctt agactgatgt   5400
gctaacatgc attcacgtgt gattacctgt ttcaatcaca gaagtggcca ttatatggta   5460
agggttgctt gactgtgttg agcatccatg tcagaggatg cattgatgcg aggctatgtc   5520 acctatgct tgcagggtca acggcagctg ttttgcatgg cccgtgccat gttgcggcgt    5580
agccgtatcc tgatgttgga tgaggctact gccagtgttg accccgagac agacagcttg   5640
attcaggctg ccatcaggtc ggcgttccag gagtgtacac tgctcaccat tgcacacagg   5700
ctgaacacta tcatggattc agacaggtgg gtcactagcc gcgtagcaca gcacagcaca   5760
gcacagcaca atacagcacg attaacatgt ggtcaagcct gtcaacagat gggccatttg   5820
tgcatgtcag tatccatctg catgaatgtg ctcagataca ctcgctgtcg ctgcatgtgt   5880
gggcttgtca tgctttcaga tgcaaccagg ccagcaggct catctggcat gaaccctgtt   5940
tattttgtag tggatataca gtattgacag caggtggagg aaattctggt cgtgactgtc   6000
tagtgtacag tggtgtgcct aagtcttgcg ttttgtctct tctttcaggg tacttgtgct    6060
agacggtgga gtggtggctg agaatgatca accacaccac ctgctgcaaa acaataatgg   6120
cctgttcaca caaatggtgg accagactgg taaacagagc agtacatacc ttaaacaggt   6180
ggcacgctct gccacaacga gcaggcagac tgccaggcgg cggatggctg ttgcacacca   6240
tgacaccgca gaaataactg atatggctgg tctgcggagt gagagtactg tgggagtagt   6300
accacaacta agccctacta tggtaagtag ggatatagtt gtgtgaagaa tggatgaatg   6360
tgctggcatg ggtattgcaa aaagctacac agtgcaaggt gtccccgcat gtaacagctc   6420
acttgccgaa accaggcctt cttgccagat caacagactg cctgttgtta tataagttgg   6480
tttgaggtgc caccaaagag cgagcactca atcactcaat catcagaaat aggtttccac   6540
ctccctgcac tgccctgttc cagcccccctt gcttgccgtg catgtgagat gtggtgttat   6600
```

-continued

| | |
|---|---|
| gcagctaaag cagtttgcag ggctcagggt acagggtaac gcaggagtgc tgctgcggca | 6660 |
| tcataccttg ttgtgccatg tcctgcagga cccactgggc ccagctgttg aggcagctcc | 6720 |
| tgctcgtttg acaacagagg tgtcacagct gcgccgcaac atcgacgcgg gtgatgttgc | 6780 |
| tctgacatca cccactgttg ctctttga | 6808 |

<210> SEQ ID NO 11
<211> LENGTH: 4556
<212> TYPE: DNA
<213> ORGANISM: Chromochloris zofingiensis

<400> SEQUENCE: 11

| | |
|---|---|
| atgaaggctg acgcagatgt ctgcatcaag gacgagaccg ttgtggacat gaaacggctt | 60 |
| gaactggaca acggcatgcc gggagtagtc agtggagggt ctcaccacct ccctgcaaag | 120 |
| cgcggcagca gttttgggcc gtctgggatg accatcagtg tgaaggtaac aagacgcgac | 180 |
| cagccattga aagtccatca tgcggcagct gtgcatggtg tgtctcatag taggtagtac | 240 |
| cccgtggcct ggaacgtttg gaaactgaaa ttggctgtct gactgcataa ccaacaggta | 300 |
| gttcaaggcc agctgctggc aatgtgcagg caatacctig cagctgcagc gtttaaatga | 360 |
| tctaccagcc aacactctcc agtgtctgtt catcagcaac attgagcagc atacataaca | 420 |
| cagcaacaat gctgcatggc tcacatgtgc tgtgctatgc aggacctcac cttctctgtc | 480 |
| aagtcaaaca ttgaaaaggg caagaccgta cacttgttaa agaatgttac aggcttcttt | 540 |
| gagcctaaca gatgtccgc cttggtgagt cacatgacaa acataaaatc acttaaaact | 600 |
| gttatgtggc agctgccgga tgcatggcat agcagtgtgc agtacatgtt ggcctcctac | 660 |
| acgcagcaat tatgtggggc aatagctggc tgacaggaag actgcatgcc aacaaccatg | 720 |
| tacttgcctc taacaagaaa ctgtccacta gtgtgtcaac acagttccaa ttgtgtgatg | 780 |
| ttgctaacag atgggtccca gtggctctgg caagaccacc tgctggata tcctggctgg | 840 |
| cagaaagacc tcaggcaaga cagagggaac catactgttt gcaggcaaca aaccaacacg | 900 |
| gcagttcctg cgacgctata caggatatgt ggagcagttt ggtaagaaga cggcggttgc | 960 |
| aagcatgtgg ttgctagcct gcaacaagtt ggtgcttgca gaatttggat gtagcaacct | 1020 |
| tggccttgg acttgacagg aatattgtgg cgtgcagcat ggcagtgaca gctctgtcat | 1080 |
| gtcaagcaaa agagacaaga gagcaagttc tgtgaacaca catacactac acagcatgac | 1140 |
| tgactgtgtc atgtttgttc attttgcaga tactctgcta ccaactctta cagtagaaga | 1200 |
| gatgctcatg tacacagctg agctcaagcg gcccatctca gaacccttat ctgagaagaa | 1260 |
| ggcagcagta gatgaactta tagacaaatt ggcgctggag agttgcaggt aatgctgttt | 1320 |
| gatatacttc aagcagttga gcaatcgcat gaacatgact ggcgtcaaga cccatggaaa | 1380 |
| cctgcattgt tgctgctaag aacagctcat tttacagtat tgctgctagt acggctagat | 1440 |
| tgtgtatgaa gtcatgtaca cgcattccaa ggtgccttgc aggtagtact gtccaattgc | 1500 |
| aggctgatgg ctgctttatc cagtatgcct ttcaaccaca acgctgccct gtgtgttcca | 1560 |
| ggaaggtgcc aattggtagt tccatgagca aaggcatcag cggtggtcag gccaaaagga | 1620 |
| ccaacatcgg tatcgcactg attactaatc cacgtgtgtt gttccttgat gagcccacca | 1680 |
| gtggttttgga cagcttcacg tccaatgagg tgagtcatca gtatgacagc tgccagcaga | 1740 |
| accagaccag ggatataagt ggcgccaatg cccgtaatgg cagccccaaa actgctgcag | 1800 |
| cagaatatac tcagcagcag ctgcattggg atgcaaagcc agtggcagta ggacaggctg | 1860 |

-continued

```
taatgtttgg gcagtgtttt atggtgtagc cccatcgctt ccaagtcttg tgaatgcatt    1920
gaccaaggaa gaggtgttca gtgtgcaatt tgacattgct tgccatgcag gtgatgaccg    1980
tggtgaaagc cctggtttcc gacggtgtca cgattgtcgc caccattcat tctccaaccg    2040
cctacgcctt caacctgttt gacaagttga tgatgctcgt caaaggcagg gtggtgtatt    2100
ttggtgctca aggcaaacca gcacttgagt atgtgcgcac ccagtgcccg caaatcaagg    2160
agcagtcaag tgggtatggc agtgatgccg agtggttggt ggacctgttc actgaggcag    2220
ataggatggg taaaggcggg gagtttgcag acgcttatga tgtatcgcag ctcaaaaagg    2280
tgagcaggtt gcaagcaggt tgccttgctg tgagtacatg tactggtggg tggttgagat    2340
ggacaaatgg gggaggtggg cgtgcaccag gggacggggg catgtgggaa gagggggaac    2400
ctgccgaatg tatccgacag tgttgttgtt tagcatgaga tgcatgccta tacactgcac    2460
atgtaggaat agagcacttg ctgatgggtt gctgggctca ttttgatgca tactacctgc    2520
agcaccccat catgcatgca aatgtatgaa ccagtatctg ctctgcttgt gtatgcagga    2580
caacgactac attgtggaca gcctctgtgc gcagaagcat gttctgcctg ctcatgttca    2640
gcaggagttg tccgttaaga cagagacagt cacaccctgg tggtggggta tcaaaacact    2700
catcaaggtg agagggttaa ctgtgccaac aacacaaaca gcagaccacg gccatgttga    2760
ttgatgcagg cttggttgca tggttgctgc tgcactgggc tgagcactgc aaactccatg    2820
gttggttgtc agagacatag tggcagtgac aactgcactt catagcatgc ttgctacaga    2880
atgatgcagg tagtcacaag cagcactcac agtatcatgt gtgctgtttg gtattaatca    2940
cgtgtgtacc tcattgccgt tgcagtaccg caccactcat aactaccgtg atgctgcttt    3000
cctgggcccc cgcatcggcg ataagctgct gattgggctg ttgattatga ccctgtacct    3060
gggtattgga gatgactttg caccagacaa cgtcatcaat attgcagctg tgaacttcat    3120
gtttgtcaca atgccagctt ttggagcagc tgcttatgtg cctgccattg tactcggtga    3180
gtgggatcat tgtccagcag tggccacaga cagtctcagc agcttcacag tgcatgccaa    3240
ctgtgcggtc aggtggtaca gcaataagca accacctcag catttactgc aggcaatcat    3300
ctgccagaag ttctgcgatg tgcgtgttgg cgttgcacat gtcagcagtc tgcatgcaag    3360
tgctaggact gaggccgtac atgctgttgt tgtgcacttg ctgttgcgag taaacttctt    3420
caaatggtct tttcctgcag cctgtcagtc agtgccatgc ccacaattct tgctgttgca    3480
gagcgcaact tgttctgtcg tgagcgtaat gacggcgtgt atcgtgttat cacatacctg    3540
atggcaaaaa tgttggatga actcatgatt gcagctgtag caagctgtgt gattgcagcc    3600
atagcattct atggcattca acttcagggg gagttcgtcc tgttttggct ggtgtattac    3660
atagtgctat gcacgggcat aggtagggtg cacagtttgt gcatatgcaa cggcatgcaa    3720
tactcttgct caacaaagcg ctgagcctgc ctgtttctgg tggtatggtt catgttaacc    3780
acttggtgcc tcttacataa actgctagca atgctggatt ggagcaaatg atccagctgg    3840
acacccaata tcatatgctg ccaatgaatc atatccgttt cacctgtgta ctaagctctg    3900
ctgctgctgc tgcaatgact actgcagtgc tcgcctactt tgtggccgct ctcagcccaa    3960
acatggatgt tgctaatgct gccctaccca cctatgtgac cagcctgctg ttctttggcg    4020
ggttcctgtt cacttttgat aagatgcctg tgtggtggaa gtggtactcc tacattgatg    4080
tgatcaggta aggccaacac agggtgtggt tgcatcaata acggcagctg atattgctga    4140
tgatgctgcc tggtaccatg cagcatatgt tgggacgcca ggcataagct aatacaatcc    4200
ccaacttgca gcttggcatg atggcctgca gctacttgta tctgtgtgct tgattaccgc    4260
```

-continued

| | | |
|---|---|---|
| cttcaccagt aaccctatct gtgcttgtgt tactagcccg ttaaagagtg tgtagctagt | 4320 |
| aacacagttg ttaaggtcct gcttgtttct tgtgcagata tgcttggaca gcaatcatgg | 4380 |
| tgaaccagtt tgaaggtcgg gatgcacaga tgttctcagg ccagacagta ctgcagtatt | 4440 |
| atggcattga gggacaaaac aagtgggcca accttggcta cacagcatgc ttcttcttct | 4500 |
| ttttcacctt ctgtgcttgg gtaacactga gtgtgaagaa gtatcagagg cgatag | 4556 |

<210> SEQ ID NO 12
<211> LENGTH: 4322
<212> TYPE: DNA
<213> ORGANISM: Chromochloris zofingiensis

<400> SEQUENCE: 12

| | | |
|---|---|---|
| atgcagctgc aattcaccaa tcaagtgggc caggcacggc taagggctgc cgttccccga | 60 |
| ccagggcaca agcatgccgg tgtacgtgca aggcctttcc aagctgcaaa accagggtgc | 120 |
| agaccaccaa caatcttagc cagctctgcg gctctgtcat ccattgacta tacctattca | 180 |
| agcagcgtga gcgatgcgaa gtctcgtccc ttccctgccg tcgctccctt gccatcccca | 240 |
| ccacgaacag ctgacttggg aaacgtgttg ccataccttg ccaaattggc cgttggagaa | 300 |
| cggcagcttc tatggcgctt cggggtggca ttaatttgca tggtgacctc caaattagca | 360 |
| ggcaagcgtc tgtaaacatg cttcattcgg tgacgggggg tgatgggctt tggtacaccc | 420 |
| actgctgctt ggatgcacac ctgcatgcgt cgtctgtgta catgcgacta gccgcatgtg | 480 |
| ccttcattat gctatacagc actgtaccag tatgctgcag cttaagccct acagaagtgg | 540 |
| cattgccgta gccttggatt tatgatacac ctgttcatgg tcgacacact caaccttgtt | 600 |
| gaaccaatgc tttgtctttg ttgttctgta ggtttggcag gcccagtact gttgcgtgaa | 660 |
| gctgtaaatg cagttggcga gcaagcaacc gcatccttac gtcctgctgt gcatgctgtt | 720 |
| gtctgctacg gtttatgtgg tgtcttaggg actctggcaa aggagctgca gcaccctaca | 780 |
| tttgcacctg tgtctcaggc tgtagcaagg cgtgttgcct accacacttt tgcacatgtg | 840 |
| ctggacttgg atatcaagtt tcatctggag cgtaggactg gccggctgtc gaggatactt | 900 |
| gagcgtggtg agcaacagac aaacaccagc agcagcagct ttggcagcat tctgtagcat | 960 |
| gctagtggtt cattcaattt gtgtacatgt actcacaaag tcaagtggca ctttgttttg | 1020 |
| ctaatggtat gctcgtccct gcatggtgct gacaccctgg actgtagact taagtacgcc | 1080 |
| ctagccgtgc agcctcaggt tcactgcaat tttaactgca attcacaagc cgcacctagc | 1140 |
| atgtcttcac tttgtgtgcc aggtacacgt agtgtgcaga tgctataccg agcagtgctg | 1200 |
| ttcaccttca taccaacagc attggagttt gcctttgtca tcggcttgct ggggactcag | 1260 |
| ttcagttcaa ctgtagctgg acttgtgcca gttacatttg tagcctatgt ggcatggaca | 1320 |
| ctagcaatga cacaggtggg gctatgggcg cctcacttag gctccatggt ataatgtcag | 1380 |
| tgtgtatgat gcaacagtgc actgaagtaa agagcactgc acatgcagaa cagtgtagta | 1440 |
| gtgcacaccc tgtaagttgg ggtactacct acaacccgaa atacaaattc actctaatgt | 1500 |
| aatctgtgta caatgtaaca atcaaccccc tccatgttcc acctggcaga gtgctgttga | 1560 |
| ggtacgcaag caggtcaaca ccctggacaa cctcaccacc agcaaggcag tagatgcact | 1620 |
| gttgaatgct gaaacagtca cactgttcaa caaccaagcg ctggaagttc agcagtatga | 1680 |
| ccactacctc agaggctttc aaagagcagc aatacagact gaacgcttga gtgcgcttct | 1740 |
| caacgctggc caatctgcca tcctaaccat tggactgatg ctggtgctga ttgctgctct | 1800 |

```
tgtgagcgca cctgccactc gccctgtgac tgccggtgat ttggtgctgt tgcaaggctt      1860
gctgctacag ctctggtctc ctctgcaatt ccttggttgg ttttacaggt aaggttgact      1920
caagaagcac tccaccagct gatgtgcatg actagtgaca caatacagaa catgcattga      1980
ctggtgccgc agtgcatgat atcccctatg agcactgttg caactgtgca tgtaatttat      2040
ttatttatcc atattcgtcc acagttgaca tcacttgcct gaacaataag tgcacaatga      2100
tgcatatgtc atgagtgatc cttgcaacaa gcttgccttc tggtggttgg tactgagcat      2160
gttgttgggt gtcaatgccc cctggccacc aatcatgaca tttgacagca gcacaggtgg      2220
tgtgcatttg agaactgcgt ttttcaccct tgaggaacat cagtgcgctt gcatgctac      2280 aattggctgc ctcacagcga tagtgttagc tgctgcctac ttaccccta c ctgacactgt     2340 atgctcacat tgctgtgctg tgcatgcttt gccactgcca gggagttgag acagtccttg      2400
gttgacatgg aggaattctt tgagatactt caaacccaga gccagctgcc cgatggccac      2460
ctgtcattac ccaacacgcc cccatgcatg gtgcgaaaca ttgcagcaca aacaagcaat      2520
agcacaagcc gcaatggcaa cagcagccag cgtttgggta gtaacactgt cagcagcaca      2580
ggcacgtccc cacatcacag ccactcccag cagcagcagc aaccggatga tcctactgcc      2640
agttatcatg agatacctta tgatgcggca tgcatctcag gctttgggtt ggaggttgaa      2700
ctgaaagatg ttcactttgg ttatcatcct gatagacaag tgctgcgtgg tgtcacactg      2760
cgcataccac ccggtcaatc agtggccatc gtgggctcgt cagggtcagg caaatcaacc      2820
atactgaagt tagtcacccg gttgtatgac gtaaccaccg gcagcgtgga ggtgaatggt      2880
gtggatatta aagatctgac gagagatagt ttgagggcag ctgtggcagt tgtccctcag      2940
gacactgtgc tgttcaatga cactatactg caaaacatca ggtaagcagt agttgccctt      3000
gagctgcagt catcacctgc agctggcaca gtcagtggta ttgtgcatgc accgtcatgt      3060
ggtatgacat gcattctact caacttcatc tgtagcttgt ttcccagaaa gtttcgaata      3120
cgtggttcaa tctgtgtgaa cctggtatgt tgctgtgctg ccagagcatg catatgcatg      3180
catgcatatg agggtggggt ggtcttctgc ccagtgcaac atgcagggtc tagcgtatac      3240
tatgttacag taatagctgg tgtgctgtag atgctggtct tgctagtttc agccgcttgg      3300
tcttaattgg accaggtctt ggttccaggg gcaaccaaca ttcctgccct gttgtgctgt      3360
ttctcatcag gtacggtcgt ccagagtcaa cagatgatga ggtcattcgc gcagctcact      3420
tggcccacct ccatgatgct gttgtcaaga tgcctgaggg ctacaagaca gtagtgggtg      3480
agagaggtct aaaactctct gggggtgaga agcagcgcgt tgcgattgcg cgtgcgttcc      3540
tgcgagcacc acgtctgctg atttgtgatg aggctacgag tgcgcttgac agtgctactg      3600
aggcatccat catgaactca ctgaatgaac tggctcaggt aggacagggt tgatggaaca      3660
ggggaaatgg attgaaatgg aaatgggtat tggagggagg tggaacaggg ggaatggagt      3720
gaggtggatc atggttcagt gatgaagagg gatgtattgt agtatgttca gtgctctctc      3780
acacatattc atgttcagct gattgcattc atcgcctgtt tgagtaccaa tgatttgcac      3840
gttgtgcaat tgcgctgtgt tgccaatgct gcacactgct ggtgttcgga tagtgaacat      3900
gcaacagcaa ctgcatgcac agtgcatgct acagtatgtt atccctgcaa ttgttgttga      3960
ccatcaaaga gtgctgctta acagcatgca gtgtgagcgc cagatcaaag tggccttgca      4020
tgtacatact gagtgcccat gtgtatctgc agggtcgcac aagcctcttt gttgctcacc      4080
ggctatccac catccgcaac tgtgatcgca ttgtggtgtt atcggctggt gtggtggtag      4140
aggagggcac acacgatcag ctgatgtcac gtggtgcagt gtacagagac atgtgggaga      4200
```

```
tgcaagcaaa ggaagccagt aggggaaatg gcgttgcaga ggggaccacc tcagacagtg    4260
aagatgggga gcgaacaatg gaacccctgc cagctgcatt gacagctaag tccttgaatt    4320
ga                                                                  4322
```

<210> SEQ ID NO 13
<211> LENGTH: 3303
<212> TYPE: DNA
<213> ORGANISM: Chromochloris zofingiensis

<400> SEQUENCE: 13

```
atgatgcaca cctcgtcctc aacattgtac ccactcggta ttataagttt cctggtcatt      60
gttgtgccat tagtcatgca cgtgctgtct cccgccggc tggacctgga cctgctgccc     120
agccctcctg ctgtgctgct gttgggacac atccagctgg cactccatgt taaagacatg     180
cacctgcagt ttctacgctg cataaccgc tttggcaagc tgttgcgcat cagagtgctg      240
cagcaggata tggtgctcat tgctgaccct gccctggcgt ctgaggtgct cacgttgggt     300
ccaaactact gtgcacggcg ccagcagac tatgccacct tcaatgtggt gagtttcagt      360
gggtgcacaa ctgtgcatgt cagtccatgg tgcaagcaag ccattggggg gctgtagcat     420
gcaatgcatg atgcaacgca gtgtgcaaat cagacttttg agtatggtta tgatgcaact     480
ctgcattagc agtagcacat caaatcacat gacttctaac tgaccagacc agtcagtaca     540
caacaagcca gccagcctac acaacagagt gtcatggcat gtgctgtgtt catctggcac     600
ctgacagtac ctggccttg cagcaacatg caatgcctgc agcattttac agctggattg      660
taagaccacc cttggcagtt tgacgggtgc atgcagtgct tgccagctgg ttgtgtcac      720 acttgcgcct tggttcctca tgtccttatg atgcatcagt tgtccctcag gctctcacca     780
ccctgttgct gtttgcttgt tgttgtcatg acagattcat ggcctgtcag cacggccctc     840
catccttact catcaagatg aggcatggtg gaaggctgtc aggagagcaa tagcacccgc     900
ctacacacct gctgccacca ggtaacaata gcagtcagca gcatgctgca gctgccagct     960
ggctgctgta ggtgtgcagt tacgcagcag tccattgtgt atgcagcagc tgattgtgta    1020
tgcagcagct gtctccattt tgattacttc attgctgtct tgtgtgctgt gctgcaggga    1080
gttgcacagc ctcatggtat ccaccatggc tcgtgtctgt gagcgtatca atgccaacct    1140
gcacagtgct gccaacaacg gcaatagcac tagcaccagc agcagcgata gcactggtag    1200
tccagcaggt atacgcatgg atgaggaggt gctggtagct gtgctggaga tcctgttgca    1260
tggttcactg cggttaccac cacaagccat gtcatcatca gatgtgcggc gcactgcaca    1320
ggtggccccc aagttagtga ccattgccaa cagctttgtg tcactgccag gcaagcagtg    1380
ggtgtacacc acattgcctt tcatttgcaa ggtgggtgag ccaactgcta agaggcagtg    1440
ctcttgggtt aggtgatagc ggttgtactg gtggccacca gggtggttgc ttttggtgct    1500
tggggtggtg gttgggatgg ggcatgcagg tggacagatg tgtctggtgg ctgtgatttg    1560
acaggcacac atgacaatgt gacataatgt tgacctgcat ggggaacaca gttccttcag    1620
gttctgtggt catgtgtgat gttgaaggaa tgcatgcttg cacacagaaa acagatccat    1680
gtgggtaata tctgctatca caggggtatt gcgggcagac ccagcactag gtatgttcgt    1740
agcatcatgc aagtgtgctc agctgccaca ccatgacatg ttgtgttgct acgctgttgt    1800
ctgcaggaag ctcgtgtcat gcatcagggc cgaacccaca tgactaatat cacacgtcaa    1860
atctataatc acatcagcgc caaatacact gtgaatggtg taccgtctgc aaagagtgat    1920
```

| | | | | |
|---|---|---|---|---|
| gtgggaggct | ctgaaaagag | tgacacatct | ctcgcctcct | gcttgatgcg | cctggcccac | 1980 |
| cctcaacaca | cgcctggtca | aacattcacc | caggatgata | tcatggctga | gattgccatc | 2040 |
| aacatcatag | gacagggatc | cgtaccatgg | acagtatctt | gggcactgta | agtgcgtctg | 2100 |
| tacatgccac | attgtgctgc | tactgccagt | taactactgc | attgaggctc | gtaggttgtg | 2160 |
| ttgctggcat | ggcaggttgt | tgttcagaag | tttctgctac | ttgctgctac | ttgctgcaac | 2220 |
| ccaaatatgc | acacaggttt | tatgtgcttt | ttgacatgga | gaaggattga | caccattgat | 2280 |
| tgcagcaaag | caacttacaa | attcagcact | tacacagtat | ttacatcggt | tgcctagatc | 2340 |
| aagtcataca | tttcgcaatg | gacactcaag | ctttgtggtt | gtgttattca | tacaggttcc | 2400 |
| agctgactca | gcggcctgat | gtggagagcc | gattgctgtc | agagctacag | ggcctggggt | 2460 |
| taccctgtga | tggtgacctg | gcggcagcat | gtgatgccat | tagtcatccg | gagtgtctca | 2520 |
| gggacacccc | ctacctgaca | gctgtcatta | atgaggtgat | gcgcatgtac | ccagctggtg | 2580 |
| tgtcagcagc | tcctaggtag | ggtacagggt | tcagggcctt | agtatttcag | ggtttacgct | 2640 |
| ttgtacttgc | attgtgtttt | acgccatgga | ttgctgcagc | ttgctgttat | ccatcactta | 2700 |
| cgtgcagggt | gctgccaggc | acagaactgt | aatgcaggga | ggtctgaaga | cgcgcttaga | 2760 |
| ctgtggcgtg | tgattgattg | tgttgttggc | aaaggtgtga | ggtgtcaggc | tgaacccatt | 2820 |
| gcatgctttc | tgagcatgaa | tggaagatgt | caaatctgac | tactgttgtg | catttgtctt | 2880 |
| tcttgctgct | cctacaggtt | gacagaacag | cccatcaagc | ttgagggta | tcgcatacct | 2940 |
| gctggcgtta | tggtcttccc | aaatttattc | accatcatga | attatagagg | taactggcag | 3000 |
| cagccagatc | agttttaccc | agatcgctgg | ctgcaaccaa | actcatcagt | agaccctct | 3060 |
| tcaggcgccc | caaggtttat | ccccttcagc | atcgggccaa | agatttgcat | agcacaacat | 3120 |
| ctggccataa | tgcagtgtaa | gattatgttg | acattgttag | tcagctgctt | gaaattccag | 3180 |
| ctggcaccca | caatggggggg | aattgagggg | gtgatgaaac | gggtagaggc | gacgttggag | 3240 |
| ttgcgggtgc | agggggggctt | gtggtttact | gcagagatca | ggaggtctaa | caatgtaaaa | 3300 |
| tga | | | | | | 3303 |

<210> SEQ ID NO 14
<211> LENGTH: 1914
<212> TYPE: DNA
<213> ORGANISM: Chromochloris zofingiensis

<400> SEQUENCE: 14

| | | | | |
|---|---|---|---|---|
| atggatggac | ttgcgatcgc | catgggctgt | gccgcggcgg | tgctggtgtg | ctatacggtg | 60 |
| ttgccattcc | tgtgcagcct | tgcactagcc | atctggaggt | ttcatacaag | caagatacccc | 120 |
| gggcctccag | caaaagactt | catcctgggt | gagcttcatt | gcaacatttt | tgcatgcatg | 180 |
| cgcacgtatt | gcatgcatgt | gcaaattcat | gtgcaagttg | ttgaacactg | cttttgctgt | 240 |
| ggtggtaaat | gttacaatca | cgttgagcta | tataacactt | accttgtttg | cctcaggcca | 300 |
| tgctgcggct | cacttgaatg | acaaggctcc | tttatttttc | aaaagatggg | ctgagaaata | 360 |
| tggcaaactt | tacaaggttc | ggatggccga | caacttcgcc | gtggtgctga | ccgatcccga | 420 |
| agtcatacag | tccatagctc | gcaaaataca | aaggtaagt | agctcagccg | ctgccagcac | 480 |
| cattctgcgc | atcatccacg | ttaatcacac | ccaaccgtca | cccaaccagg | tgatgaatac | 540 |
| tgaatactgc | gcatgtactg | cagaatgaat | cagttcattg | attagctagg | aaccaagttg | 600 |
| taaacctctg | cttcttgctg | tcaggcgctc | aattggcgca | ctttgtaaac | gcactgtctt | 660 |
| ggtccagcca | agctagtgtc | aaacagctac | acccccttgat | gcaattcttg | atgcgtttgt | 720 |

| | |
|---|---|
| gaggaatttg catttatgac tccttactct gcgccctgca tgcagcctac caaatcgtac | 780 |
| agtagtcttg agctgggcac gttccccaag gatcacaaca tcttgaccgc tccagatggc | 840 |
| ccacactgga aagcagtaag acaaggcata acaccagcat tcagtgtagc aaacttgaag | 900 |
| caggtactga cgctaagtca tgtagaagca gtgcagcaca tcagcactga cgcacatcag | 960 |
| agttgacatt cagtgcatta ccatagtaca agtgtctcca tgtcagtgtc actgcgagca | 1020 |
| gcatggctgc acaagggcat ctctgctcaa gctgttgttg ttgtatacaa atggtactgt | 1080 |
| taacttggta gagcgcaata acatcctgca cactgcacaa caattacaat ttttctacc | 1140 |
| agtgttgacg acaggtcctc ctatattttg catcgtgtga tgtgcagccc tgcttgagac | 1200 |
| gtttgatgta gtgatgaggc tgctcttgtt gctctgctca gacactgctg cttgtaatgg | 1260 |
| tggagcattg tactcactgt gagcataaca ccttatggtc gtgcaactgc tggtgattgc | 1320 |
| aatgccatgc attagttgcg gtcataaact gtgagcctca tgatgtccct gcttgccgca | 1380 |
| ggtattcccc tggttgtgcc atgtcaccaa ggtggctgca gctaaactcc aggacacagg | 1440 |
| cccttccacc agctttgaca tttctgacat tgccaagcgg atcaccagtg atgtcattgg | 1500 |
| gcagctgctg tatgcggaag acctgggagc catagcatat aggtggttg tgtggtaggg | 1560 |
| ttaccactac tgatcaatgt ctagtggctg gtaactggtg tgcaaaagca gtcacatcac | 1620 |
| gctgttgatg caaacaaatg ctgctgtgta tgaagtgtta cagcacttac ctgtatcaag | 1680 |
| agccagccta tggggtcaga tatagcgctt gcacaacaac acactctggt gtgctgctat | 1740 |
| gcacatgtac atactgaagt atcattgttg tgcaggccca gtgaatacct ggagctgttc | 1800 |
| cagatcggca tcactgcagc tcataagagc cttgggagac ctttacggct gtatgccatc | 1860 |
| tgggatcctg aggtgaggcg tcagaaccgc gcaataaacc gtcttgacca gtag | 1914 |

<210> SEQ ID NO 15
<211> LENGTH: 1200
<212> TYPE: DNA
<213> ORGANISM: Chromochloris zofingiensis

<400> SEQUENCE: 15

| | |
|---|---|
| atggaagcag cactgaccac tgccgtagat gcagcggcag cgttacgaaa caacataggc | 60 |
| ttcttgcaaa gaagccagat agcaatcgta gcagcgttcc tgtcagcaat atacctcaaa | 120 |
| ctggttgtgt caaggatagc acctggctgg aaaagcttag cacttgtggc tccgctgctt | 180 |
| gcattgaacc tgtggctccc gctactcttt catatgagag aggaggtcgt cagcaggact | 240 |
| tgcgtggtat tcctaatatc ttggctcggc agcttcaagg caattggtat gtgcctcaat | 300 |
| agggggccac tggctgctga ttggagtgta gcacagatga tcttcctgta tgttgcacca | 360 |
| gtactacccc gacaagatgc tggcggccct gtcaaagcag gccggctgca ggacagtgct | 420 |
| ggcacctggg gaactcttgc ggcatcattt gtgatcaaca ccacaattct tggtgttgtt | 480 |
| tcttacctac tggtggtgat ggacatgcca aaagtagtca agatatacat ctacgcattg | 540 |
| ggtttatatg gctttgtctc gtttattatg gagggtccag cagccatcat tgtgggcttg | 600 |
| ctgaggatcg aacttgtgcc tcccttttgat aaaccatggc tggcgactag tttagctgac | 660 |
| ttctggggtc ggcgttggaa caactccact agtttgttac tacggttcct ggtgtatgat | 720 |
| cccatcattg aaggcaggtt ggtgaagaag gccaaacaag aggatccaca gcaacctgct | 780 |
| ccaagcaagc aagtcagcaa cagcatgagg ctgactgcca tgcttgctac gtttgcattg | 840 |
| agtgggctga tccatgaagc catcttggcg tatgtgaatc ggccatacta cccaggaccc | 900 |

```
tggttcatgt tcttcttcat tcagggcccc ttgttggcag tggagatgcg ggtacacaag    960
catctgaggg caacacacaa gcagctgcca ttcactgctg catggacctt gacaacagca   1020
tgtctgctgt taacagctta catgttttc ttccctccca tcgaagactg gacagacctt   1080
gcaccaagaa tagctcaagc agtcaccagc aacttccaag cagtgttagg cccgcttcag   1140
gggctggggc gccagtactg ggctgtagca gctgggttgg tgcaacagtc agccatttga   1200
```

<210> SEQ ID NO 16
<211> LENGTH: 1131
<212> TYPE: DNA
<213> ORGANISM: Chromochloris zofingiensis

<400> SEQUENCE: 16

```
atgccggtac ctgtgtccac aacccaccca aatggcaagg gaatgcgcgc agccaacctc    60
acggagttac ccacagaggg gccttttca cgatcgctga agcagaaaga ggatagtgcc   120
aacacaggag cagatgcaat agcattgcaa acaaacggca ctgctgacgc ctcgcttgat   180
gccaatgcac catcaccatt gccagagccg ggaccatcag tgctggttca tcatctagac   240
ttcacatacc cagggttaga tggccgcccct gtgcctggtc aacctcctct gataaccgac   300
atgtgcctga cgctacagcc gggcagcagg tgcttgctga ttggcgctaa cggtgcaggc   360
aaaacaacgc tgctcaaaat actgggtggc aagcatatgg tacccaagga tgctgttcat   420
atactgggtg caccacctt ccatgacaca catctcacca tcagggca cctgtcatac   480 attggtggta attggactcg tgatattgca ttcgcaggat taagcatacc gctaacgggt   540
gacttccctg cttcacggat gattgatgcc atcccagagg ttgaccccgc acgtaaagaa   600
cgcctgatca aggtgctgga cattgatcca aactggcgca tgcatacggt gtcagatggt   660
caaagaaggc gtgtgcagat ctgtgttggg ttgttgcgcc cattcaaggt gctgcttctg   720
gatgagatta ccgtggacct ggatgtgctt ggtagggctg atctgatgca tttcctggct   780
gatgaatgcg ccaccagagg agctagcatc atatatgcca cacacatatt tgatggtctg   840 gagtttggc ccacacatgt agcatatgtt gcaagagggc ggctgcagat ggtcaagtca   900
gctgaggaga tatctgagct caagcagggc aggttgttag agcttgtcac cagcctgttg   960
agggaggaac gcgaggcagt gaaagctgct ggcgtcagta aaccactgga gtatgatccc   1020
agtctagaag gacaggttac aaacttctca tatgccttca ataatggttg ggttcctgga   1080
acgttgagca cctccttggc caagagtact aatgctgtga tgcgtaattg a   1131
```

<210> SEQ ID NO 17
<211> LENGTH: 3969
<212> TYPE: DNA
<213> ORGANISM: Chromochloris zofingiensis

<400> SEQUENCE: 17

```
atgcttcaga ggatagtagg cgggcttcaa tgctacgcaa ggcagcaggc tgtaccgtcc    60
gtgcagtgtc ctgagaacgc ctatttgtac tattggatca taggtctgtc gttagcacct   120
ttactacaga gcttagcaga aaactccatg aattttgagc tcagcgtcat cggcacacgc   180
atgcgcaatg gactgatggc agccatatac cgcaagtgtc tgcggttgtc caactcagcc   240
atacagagtg agagcaccgg caaggtggtc acacttatga gtaatgatgc tcagaaggtt   300
caagatgcca tgatggccat ccacaccatc tggggtgcac ctgccctcat tgtggtcatt   360
accatactgt tgtaccaaca agtgggatgg caacctttg tgggactagg aatcatgctt   420
atctatgcac ccatgacagg caaagtgtca cggaagctgg tggtactgcg tcgcagcatc   480
```

```
atgcagtgga cagatcgccg cgtgggcctc atgaatgagg tcatcaatgg catgcaaatg      540
atcaagttct atgcctggga gaactccttc aagaggcaga tcctgcatgc cagagacaat      600
gaagccagaa tcctgaagac tgtggtgttg tggcagtcat tttttgcaat gctcctgttc      660
agcggccctg tggctgtagc agtattctgt tttggttcct gggcattagc tggctatggc      720
ctgacagcag cgtcagccta cacagcactg tcactgttca gtctgttgcg aatgcctctt      780
gtcatgttgc ctatgatgat taccatgatc attaatgcac tggtggccct gaaccgcatc      840
agcgcgttct tgctgcgtgg cgagatacag accaccagcc agccaggtca tgatggcaac      900
agcagtaaag agaaacagga gactgttcag gagactgttc aggagactgt tcaggagact      960
gttgaacctg gagtggtgcg ggtgactgag ggaccttca gttgggactc tgctggcgat     1020
caggcagccc tgcgtgatgt caacttcact gctgcccta gttcattgac catggtggtg     1080
ggcagtgtgg ggtgtggcaa gagcagtctg ctgtcagcat tgattggcca gatggagaag     1140
caaggaggag aggtgcagct tggaggcagg gttgcctatg ttgcacaaac ggcatggatc     1200
atcaacgaca tggtgcagga gaacatcctt ttgggtgaag cattcgatgc tgatcggtac     1260
cgtatggcag tggagatctc tcagctagtg cctgacctag agctactgcc aaatggtgat     1320
cgcacagaga ttggcgaccg cggcgtcacc ctgtccgggg gccagaagca gcgtgtgtcg     1380
attgcaaggg ctgtatacag tgatgctgat gtgtacctgt ttgatgatcc tctcagtgct     1440
gttgattccc atgtgggtcg agcactgttt gagaagtgca tacggggtgt cctgcgcaac     1500
aagacagtca tcctggtgac taatgccctc caatatctgc cctctgcgga taatattttg     1560
tggatggaag gtggtgctgt gaaggctcag ggcagctaca gccaattggt ggccgctggc     1620
atgaatgtgg ctgagctggt acatgttgag catgaagctg aacagacaca tcagcgggat     1680
gaggacccca gcaggcaggc aggcacgggt gtagtagcag aggaggctga ccttcctgat     1740
gatcatgaca gtacaggcac gtctggcact gactcagctt acagtgatga cattgccaaa     1800
gctaccatcg tttctcatga tgatgctgat ggtgataaag cagccaggca tgtgaagggg     1860
tcctacatcc cagagggaaa gccatcaaag tccatcacgc taaggaagat agatactgta     1920
gacaacagga atctgacagg tattgaggct cgtgagacgg gcgctgtgag tgggaaggtg     1980
ctcaagtcat acatcatcgc tggcggcggc ttcatcatta tagccttcgt tgcgctattg     2040
tttgctgctg agcagggtgc ccgtgtgttc acggacactt gggttgggct ctggtttggt     2100
gatgcgttca ggcagaatgt gtggttctat gtgggtatct atgcagcact gggaatactg     2160 tacagttttcc tcactttcct cagggcactt cgtttcaact actcagccgt caatgcagcc     2220
ctgtctctcc acaaccagct gttgaatcac atcctgcgcc tgcccaaatc attctttgac     2280
accaacccag ctggcagaat tctcaacagg ttcagcagag acactgaaat catggacagc     2340
actgttgcta catcagcgct catgttctgc aactgcatgg cgacattcat cgccatcctg     2400
attgtgatca gtgttgcaac gaaatggttt gctgtagcca tcatccctat caccatcaca     2460
tacatgctac tgcagcggta ttacatccca tccgctcgtg agctgcagcg cattgaaagt     2520
gtgtcccgca gtcccatcta cagcaaattc agtgaggcgc tggcaggcgt gcccaccatc     2580
agggcttaca ggaaggagcg gtactttaca gtcaccagtg ataagctgat gcaggagaac     2640
gcatacgctt acatcagtca gaggtctgca gcttcatggc tggccatgag acttgatgtt     2700
gtgggtgtgc tcatcctgac attgacaggt gtgttgtgca ttcaaggcac catcagcccc     2760
ggcctagcag gtctgtgcct ggtgtatgca ctggacctga cacgctacct gaagatgggc     2820
```

```
acggcaatgg catccaagac agagtctgat ttcaacagtg tggagcgaat cattcagtac    2880
ctggagcctg cacctgaagc tgatgctgac acacccgcag atgtgctggc cacactgcca    2940
gccaactggc tgctgctgg cagcatcagc gtgagggatg tgtgcatgcg ctaccgccct    3000
gggctacctc ttgtgttgaa gggcgtcagt tttgacattg cgcctggtga aaggtgggg    3060 ctggtgggca ggacaggcag tggcaagagc tcactgttcc tagcactgtt caggatggcc    3120
gaaccagagt ctggcagtat tctgatcgat ggtgttgaca tccgtaccct tggcctgcac    3180
acactgcgtg ctgctatgtc tgtcatccct caagacccct tcatgttcag cggtactgtg    3240
cggcacaacc tggatccatt tgacgaacat cctgacagtg agttgtggcg cgtgctagaa    3300
gcggttgggc tgaagacagt catatctgta ctggaggcaa aactagaagc tcctgtggtg    3360
gacaatggtg ccaacttttc acagggtcaa cggcagctgt tttgcatggc ccgtgccatg    3420
ttgcggcgta gccgtatcct gatgttggat gaggctactg ccagtgttga ccccgagaca    3480
gacagcttga ttcaggctgc catcaggtcg gcgttccagg agtgtacact gctcaccatt    3540
gcacacaggc tgaacactat catggattca gacagggtac ttgtgctaga cggtggagtg    3600
gtggctgaga atgatcaacc acaccacctg ctgcaaaaca ataatggcct gttcacacaa    3660
atggtggacc agactggtaa acagagcagt acataccttta aacaggtggc acgtctgcc    3720 acaacgagca ggcagactgc caggcggcgg atggctgttg cacaccatga caccgcagaa    3780
ataactgata tggctggtct gcggagtgag agtactgtgg gagtagtacc acaactaagc    3840
cctactatgg acccactggg cccagctgtt gaggcagctc ctgctcgttt gacaacagag    3900
gtgtcacagc tgcgccgcaa catcgacgcg ggtgatgttg ctctgacatc acccactgtt    3960
gctctttga                                                           3969

<210> SEQ ID NO 18
<211> LENGTH: 1914
<212> TYPE: DNA
<213> ORGANISM: Chromochloris zofingiensis

<400> SEQUENCE: 18
atgaaggctg acgcagatgt ctgcatcaag gacgagaccg ttgtggacat gaaacggctt      60
gaactggaca acggcatgcc gggagtagtc agtggagggt ctcaccacct ccctgcaaag     120
cgcggcagca gttttgggcc gtctgggatg accatcagtg tgaaggacct caccttctct     180
gtcaagtcaa acattgaaaa gggcaagacc gtacacttgt taaagaatgt tacaggcttc     240
tttgagccta acaagatgtc cgccttgatg ggtcccagtg gctctggcaa gaccacccctg    300 ctggatatcc tggctggcag aaagacctca ggcaagacag agggaaccat actgtttgca     360
ggcaacaaac caacacggca gttcctgcga cgctatacag gatatgtgga gcagtttgat     420
actctgctac caactcttac agtagaagag atgctcatgt acacagctga gctcaagcgg     480
cccatctcag aacccttatc tgagaagaag gcagcagtag atgaacttat agacaaattg     540
gcgctggaga gttgcaggaa ggtgccaatt ggtagttcca tgagcaaagg catcagcggt     600
ggtcaggcca aaggaccaa catcggtatc gcactgatta ctaatccacg tgtgttgttc     660
cttgatgagc ccaccagtgg tttggacagc ttcacgtcca atgaggtgat gaccgtggtg     720
aaagccctgg tttccgacgg tgtcacgatt gtcgccacca ttcattctcc aaccgcctac     780
gccttcaacc tgtttgacaa gttgatgatg ctcgtcaaag cagggtggt gtattttggt     840 gctcaaggca aaccagcact tgagtatgtg cgcacccagt gcccgcaaat caaggagcag     900
tcaagtgggt atggcagtga tgccgagtgg ttggtggacc tgttcactga ggcagatagg     960
```

-continued

| | | | | |
|---|---|---|---|---|
| atgggtaaag | gcggggagtt | tgcagacgct | tatgatgtat | cgcagctcaa aaaggacaac 1020 |
| gactacattg | tggacagcct | ctgtgcgcag | aagcatgttc | tgcctgctca tgttcagcag 1080 |
| gagttgtccg | ttaagacaga | gacagtcaca | ccctggtggt | ggggtatcaa aacactcatc 1140 |
| aagtaccgca | ccactcataa | ctaccgtgat | gctgctttcc | tggggccccg catcggcgat 1200 |
| aagctgctga | ttgggctgtt | gattatgacc | ctgtacctgg | gtattggaga tgactttgca 1260 |
| ccagacaacg | tcatcaatat | tgcagctgtg | aacttcatgt | tgtcacaat gccagctttt 1320 |
| ggagcagctg | cttatgtgcc | tgccattgta | ctcgagcgca | acttgttctg tcgtgagcgt 1380 |
| aatgacggcg | tgtatcgtgt | tatcacatac | ctgatggcaa | aaatgttgga tgaactcatg 1440 |
| attgcagctg | tagcaagctg | tgtgattgca | gccatagcat | tctatggcat tcaacttcag 1500 |
| ggggagttcg | tcctgttttg | gctggtgtat | tacatagtgc | tatgcacggg catagtgctc 1560 |
| gcctactttg | tggccgctct | cagcccaaac | atggatgttg | ctaatgctgc cctacccacc 1620 |
| tatgtgacca | gctgctgtt | cttttggcggg | ttcctgttca | cttttgataa gatgcctgtg 1680 |
| tggtggaagt | ggtactccta | cattgatgtg | atcagatatg | cttggacagc aatcatggtg 1740 |
| aaccagtttg | aaggtcggga | tgcacagatg | ttctcaggcc | agacagtact gcagtattat 1800 |
| ggcattgagg | acaaaacaa | gtgggccaac | cttggctaca | cagcatgctt cttcttcttt 1860 |
| ttcaccttct | gtgcttgggt | aacactgagt | gtgaagaagt | atcagaggcg atag 1914 |

<210> SEQ ID NO 19
<211> LENGTH: 2307
<212> TYPE: DNA
<213> ORGANISM: Chromochloris zofingiensis

<400> SEQUENCE: 19

| | | | | |
|---|---|---|---|---|
| atgcagctgc | aattcaccaa | tcaagtgggc | caggcacggc | taagggctgc cgttccccga 60 |
| ccagggcaca | agcatgccgg | tgtacgtgca | aggcctttcc | aagctgcaaa accagggtgc 120 |
| agaccaccaa | caatcttagc | cagctctgcg | gctctgtcat | ccattgacta tacctattca 180 |
| agcagcgtga | gcgatgcgaa | gtctcgtccc | ttccctgccg | tcgctccctt gccatcccca 240 |
| ccacgaacag | ctgacttggg | aaacgtgttg | ccataccttg | ccaaattggc cgttggagaa 300 |
| cggcagcttc | tatggcgctt | cggggtggca | ttaatttgca | tggtgacctc caaattagca 360 |
| ggtttggcag | gcccagtact | gttgcgtgaa | gctgtaaatg | cagttggcga gcaagcaacc 420 |
| gcatccttac | gtcctgctgt | gcatgctgtt | gtctgctacg | gtttatgtgg tgtcttaggg 480 |
| actctggcaa | aggagctgca | gcaccctaca | tttgcacctg | tgtctcaggc tgtagcaagg 540 |
| cgtgttgcct | accacacttt | tgcacatgtg | ctggacttgg | atatcaagtt tcatctggag 600 |
| cgtaggactg | gccggctgtc | gaggatactt | gagcgtggta | cacgtagtgt gcagatgcta 660 |
| taccgagcag | tgctgttcac | cttcatacca | acagcattgg | agtttgcctt tgtcatcggc 720 |
| ttgctgggga | ctcagttcag | ttcaactgta | gctggacttg | tggcagttac atttgtagcc 780 |
| tatgtggcat | ggacactagc | aatgacacag | agtgctgttg | aggtacgcaa gcaggtcaac 840 |
| accctggaca | acctcaccac | cagcaaggca | gtagatgcac | tgttgaatgc tgaaacagtc 900 |
| acactgttca | acaaccaagc | gctggaagtt | cagcagtatg | accactacct cagaggcttt 960 |
| caaagagcag | caatacagac | tgaacgcttg | agtgcgcttc | tcaacgctgg ccaatctgcc 1020 |
| atcctaacca | ttggactgat | gctggtgctg | attgctgctc | ttgtgagcgc acctgccact 1080 |
| cgccctgtga | ctgccggtga | tttggtgctg | ttgcaaggct | tgctgctaca gctctggtct 1140 |

-continued

| | |
|---|---|
| cctctgcaat tccttggttg gttttacagg gagttgagac agtccttggt tgacatggag | 1200 |
| gaattctttg agatacttca aacccagagc cagctgcccg atggccacct gtcattaccc | 1260 |
| aacacgcccc catgcatggt gcgaaacatt gcagcacaaa caagcaatag cacaagccgc | 1320 |
| aatggcaaca gcagccagcg tttgggtagt aacactgtca gcagcacagg cacgtcccca | 1380 |
| catcacagcc actcccagca gcagcagcaa ccggatgatc ctactgccag ttatcatgag | 1440 |
| ataccttatg atgcggcatg catctcaggc tttgggttgg aggttgaact gaaagatgtt | 1500 |
| cactttggtt atcatcctga tagacaagtg ctgcgtggtg tcacactgcg cataccaccc | 1560 |
| ggtcaatcag tggccatcgt gggctcgtca gggtcaggca atcaaccat actgaagtta | 1620 |
| gtcacccggt tgtatgacgt aaccaccggc agcgtggagg tgaatggtgt ggatattaaa | 1680 |
| gatctgacga gagatagttt gagggcagct gtggcagttg ccctcagga cactgtgctg | 1740 |
| ttcaatgaca ctatactgca aaacatcagg tacggtcgtc cagagtcaac agatgatgag | 1800 |
| gtcattcgcg cagctcactt ggcccacctc catgatgctg ttgtcaagat gcctgagggc | 1860 |
| tacaagacag tagtgggtga gagaggtcta aaactctctg ggggtgagaa gcagcgcgtt | 1920 |
| gcgattgcgc gtgcgttcct gcgagcacca cgtctgctga tttgtgatga ggctacgagt | 1980 |
| gcgcttgaca gtgctactga ggcatccatc atgaactcac tgaatgaact ggctcagggt | 2040 |
| cgcacaagcc tctttgttgc tcaccggcta tccaccatcc gcaactgtga tcgcattgtg | 2100 |
| gtgttatcgg ctggtgtggt ggtagaggag ggcacacacg atcagctgat gtcacgtggt | 2160 |
| gcagtgtaca gagacatgtg ggagatgcaa gcaaaggaag ccagtagggg aaatggcgtt | 2220 |
| gcagagggga ccacctcaga cagtgaagat ggggagcgaa caatggaacc cctgccagct | 2280 |
| gcattgacag ctaagtcctt gaattga | 2307 |

<210> SEQ ID NO 20
<211> LENGTH: 1677
<212> TYPE: DNA
<213> ORGANISM: Chromochloris zofingiensis

<400> SEQUENCE: 20

| | |
|---|---|
| atgatgcaca cctcgtcctc aacattgtac ccactcggta ttataagttt cctggtcatt | 60 |
| gttgtgccat tagtcatgca cgtgctgtct tcccgccggc tggacctgga cctgctgccc | 120 |
| agccctcctg ctgtgctgct gttgggacac atccagctgg cactccatgt taaagacatg | 180 |
| cacctgcagt ttctacgctg gcataaccgc tttggcaagc tgttgcgcat cagagtgctg | 240 |
| cagcaggata tggtgctcat tgctgaccct gccctggcgt ctgaggtgct cacgttgggt | 300 |
| ccaaactact gtgcacggcg ccagcagac tatgccacct tcaatgtgat tcatggcctg | 360 |
| tcagcacggc cctccatcct tactcatcaa gatgaggcat ggtggaaggc tgtcaggaga | 420 |
| gcaatagcac ccgcctacac acctgctgcc accagggagt tgcacagcct catggtatcc | 480 |
| accatggctc gtgtctgtga gcgtatcaat gccaacctgc acagtgctgc caacaacggc | 540 |
| aatagcacta gcaccagcag cagcgatagc actggtagtc cagcaggtat acgcatggat | 600 |
| gaggaggtgc tggtagctgt gctggagatc ctgttgcatg ttcactgcg gttaccacca | 660 |
| caagccatgt catcatcaga tgtgcggcgc actgcacagg tggcccccaa gttagtgacc | 720 |
| attgccaaca gctttgtgtc actgccaggc aagcagtggg tgtacaccac attgcctttc | 780 |
| atttgcaagg aagctcgtgt catgcatcag ggccgaaccc acatgactaa tatcacacgt | 840 |
| caaatctata atcacatcag cgccaaatac actgtgaatg gtgtaccgtc tgcaaagagt | 900 |
| gatgtgggag ctctgaaaa gagtgacaca tctctcgcct cctgcttgat gcgcctggcc | 960 |

```
cacccctcaac acacgcctgg tcaaacattc acccaggatg atatcatggc tgagattgcc   1020
atcaacatca taggacaggg atccgtacca tggacagtat cttgggcact gttccagctg   1080
actcagcggc ctgatgtgga gagccgattg ctgtcagagc tacagggcct ggggttaccc   1140
tgtgatggtg acctggcggc agcatgtgat gccattagtc atccggagtg tctcagggac   1200 acccccctacc tgacagctgt cattaatgag gtgatgcgca tgtacccagc tggtgtgtca   1260
gcagctccta ggttgacaga acagcccatc aagcttggag ggtatcgcat acctgctggc   1320
gttatggtct cccaaattt attcaccatc atgaattata gaggtaactg cagcagcca    1380 gatcagtttt acccagatcg ctggctgcaa ccaaactcat cagtagaccc ctcttcaggc   1440
gccccaaggt ttatccccctt cagcatcggg ccaaagattt gcatagcaca acatctggcc   1500
ataatgcagt gtaagattat gttgacattg ttagtcagct gcttgaaatt ccagctggca   1560
cccacaatgg ggggaattga gggggtgatg aaacgggtag aggcgacgtt ggagttgcgg   1620
gtgcaggggg gcttgtggtt tactgcagag atcaggaggt ctaacaatgt aaaatga     1677

<210> SEQ ID NO 21
<211> LENGTH: 744
<212> TYPE: DNA
<213> ORGANISM: Chromochloris zofingiensis

<400> SEQUENCE: 21
atggatggac ttgcgatcgc catgggctgt gccgcggcgg tgctggtgtg ctatacggtg   60
ttgccattcc tgtgcagcct tgcactagcc atctggaggt ttcatacaag caagataccc   120
gggcctccag caaaagactt catcctgggc catgctgcgg ctcacttgaa tgacaaggct   180
ccttttattt tcaaaagatg ggctgagaaa tatggcaaac tttacaaggt tcggatggcc   240
gacaacttcg ccgtggtgct gaccgatccc gaagtcatac agtccatagc tcgcaaaata   300
caaaagccta ccaaatcgta cagtagtctt gagctgggca cgttccccaa ggatcacaac   360
atcttgaccg ctccagatgg cccacactgg aaagcagtaa gacaaggcat aacaccagca   420
ttcagtgtag caaacttgaa gcaggtattc ccctggttgt gccatgtcac caaggtggct   480
gcagctaaac tccaggacac aggcccttcc accagctttg acatttctga cattgccaag   540
cggatcacca gtgatgtcat tgggcagctg ctgtatgcgg aagacctggg agccatagca   600
tataggccca gtgaatacct ggagctgttc cagatcggca tcactgcagc tcataagagc   660
cttgggagac ctttacggct gtatgccatc tgggatcctg aggtgaggcg tcagaaccgc   720 gcaataaaacc gtcttgacca gtag                                        744

<210> SEQ ID NO 22
<211> LENGTH: 10
<212> TYPE: DNA
<213> ORGANISM: Chromochloris zofingiensis

<400> SEQUENCE: 22
aaacatctag                                                         10

<210> SEQ ID NO 23
<211> LENGTH: 13
<212> TYPE: DNA
<213> ORGANISM: Chromochloris zofingiensis

<400> SEQUENCE: 23
aatctgtggt agg                                                     13
```

```
<210> SEQ ID NO 24
<211> LENGTH: 20
<212> TYPE: DNA
<213> ORGANISM: Chromochloris zofingiensis

<400> SEQUENCE: 24
aaacatctag acacatctag                                                 20

<210> SEQ ID NO 25
<211> LENGTH: 20
<212> TYPE: DNA
<213> ORGANISM: Chromochloris zofingiensis

<400> SEQUENCE: 25
aaacatctag acacatctgg                                                 20

<210> SEQ ID NO 26
<211> LENGTH: 3942
<212> TYPE: DNA
<213> ORGANISM: Chromochloris zofingiensis

<400> SEQUENCE: 26
atgacagaac tggagaagct gggtatccca aractkaacg accacaacta tgtcttctgg      60
cacatcaaga tgcgagccta cctygttgca agaggataca gcgcagcaat aacgaacgca     120
gaagacgcca acagtgacaa ggctcttgct tccatcactt ggctgtgga agatcatttt     180 ctacctacag trtacaawgc tgcaagtgcg aaggcagcat gggacgcgct ggaggcgttg     240
tttcagcagc ggagcgttgc caaccagctg aacctcacgc aggaactgaa caacctcaca     300
ctgcagcctg gggagaccat cacacagcta cttgctcgtg ccagaatcat atgggagcag     360
cttaaggcag ctggtatcga caagtcagag caggaggtgg cgttatcagt gttgtcagga     420
cttcctgccg acttcaacac cttagtgaca gtactacaga atcagtctgg tccmctyacy     480
ctgrgtggca tccagaaggc tgtcttgaca gaacagcaac gtgcaaataa ggttggggca     540
tcaacgtcta ctgcagcaag caccaaggct ttctacactc agaacggtcc caaccrtggc     600
argcttggtg acagcggtac caggaccagc aacttcaaca ccaagcagca ggagcagcgt     660
aagtgctact actgtggcaa gaaggggcac ctgaaaaggg actgcagaaa gaagaaggca     720
gacgagcagc gtggccccag taccaaggct caacaacaa tggcatggac tgcagcctgc     780
aacaccagca tcagcctcag ctcaggtacc tgggtcctcg actctggagc atcaagacac     840
gtctgcaaag aacgcagcct gatgcagaac ctgcaacagc tgaaccagcc agtctacatc     900
acgtacggca acggtagcac aggggtggca cagactatgg gggaggttgt tctcaacgac     960
aggatccgtc tacggaacgt tttgtttgat cccactgctg ttggcaatct cctttccatc    1020
cstacagcag ctgcrygtgg agcacagttt aactttgsag ccarttgctg caccattcga    1080
gtaaatggca gactggtggc aatagcacag cagcawgayg gtcactaytg cttgcactct    1140
gagcawrcas agtcagccac tgcactggca gcccagaccc cgcagctgtg gcatcgtcgt    1200
tttggccatc tcagctacca gaatatggcc aaggtcccca acttggtaac gggcgtccaa    1260
gtsccaactg argcctttca ggcagcaggt cagcaggtgt gtgagccatg tctactkggc    1320
aaacagacac gactgtcttt ccccgagtca garactgtca ggcagcagyc actkgarctg    1380
gtgcatatgg acctctgtgg acctctycct gtcaagtcac ttggaggcag ccagtacatt    1440
gctacgttcc tggaygacta yacaggactg tcagtrgtgg cattgctcaa acagaagtca    1500
gacatttcya argttgtgcc tgacgtcttc aacatgctag agaaacagag caacaatcag    1560
```

```
gtgaagggcg tccgcactga caacggcggg gagtatgtca acaatgtgmt gaacagctac    1620
tacagcagca agggcatcat cgcacagcac acagtaccat acagtcctca gcagaatggc    1680
aaggcagaaa gactcaaccg aaccctactg gacaaggcac gttccatgct ggcagatgca    1740
rggctacctt ctcagctrtg gggtgaggcc gtggtaacag ccaattatct taggaaccgt    1800
tcaccagcag ctggcaagac agcaacaccc tgggaactgt tttttgggtc acggccctct    1860
gtctctcatc ttcgcgtgtt tggggccaag gcgtttgcac agatccccaa ggagaaacgt    1920
ggcaagctgg acccaaggag tcagcgtggc atcatggttg gatatgagcc yaatgtaaag    1980
gggtaccgtc tactgcttcc aaacaacacc atcacagtca gccgggacgt tgtatttgat    2040
gaaggtgacc agccaggagc artagacacc aacttctatc cagacttgga agatgagctt    2100
gatgttactg cagccatcaa cactggatct aatgcagcac cttctgtcaa tacttctgga    2160
acagctgagc caccaccatc agttgcagca cccgtcgacc caccaatttc ggcacagacc    2220
atggaaaacg tgggagccag caacagctca acaccacaag gcagygagga agatcagcat    2280
cagcaatcac gtagaagtag ccgggccaac attggcatgg caccaggcaa ctactgggag    2340
gccaactaca ttcccacatc aagcgtaca gctaccggac tgttggcaca gacatcagaa    2400
attgttgagc cagcaaccta tgamgaagca ctacagtcag actgtgcaga gcagtggcag    2460
caagccatgg acagcgagta cgcatcgctg atagccaatg gaacttggac cttggaaaaa    2520
cccccaacag acattaggcc catccctgtc aagtgggtgt ataaggtgaa acgtgacacc    2580
agcgggaaca ttgagcggtt caaggcacgc ctggtggcca agggttttg gcaacaggaa    2640 ggtgtggatt atgacgaagt gttcgccccg gtaagcaagt atgctacctt tcgggcacta    2700
atggccaagg cagcagaaga ggacatgaaa ctacacaaat tggatgtcaa gactgcgttc    2760
cttcaaggca acctggaaga agatgtttgg atccagcagc ctcgtggcta cgaggarggc    2820
agcagtgaac tmgcctgtca tctwcayaaa cctttgtacg ggctcaagca ggcycctcgr    2880
gcwtggcatc agcggctaca acaggaacta ctggcagtag gctacacagc atcagcagca    2940
gaccccagcc tgtactggta ctgcatcaac ggggactatg tgtacctcct ggtctaygtg    3000
gatgatatcc tgattgcagc caagcagctt gagtcagtca aggcagtcaa gcagcagctr    3060
ttaggcttat ttgagtcgcg tgaccttgga gaagcwacat cctaccttgg tatgagcatt    3120
cagcgcaaca gacagacagg caycatcaag atygggcacc gactcatgat cacagagtta    3180 ctggararagt atggygcagt mgacagcaaa athaagtcar taccactgtc tccatctatc    3240
aarctrgcya aagatgaagg cgryccccta gacaaggaac attacccctta cagccaactg    3300 gttgggagtc tcatgtacct tgcaatcacc tccaggccag acctcgcctt ttctgtgggg    3360
gctcttgcac gctacatgtc atgcccaacc acwgtccayt ggcargcagc taagggrgtr    3420
ctacgctact gggaggaac cctggactat ggcatcacct ttggtagcga cagcaatgac    3480
ctcattggct actgtgacgc agactatgcg ggagacacag acacgcaa gtccaccagt    3540 ggctacatat tcatactgca cggaggggcc atyacktgga gtagtaagcg ccaggcaaca    3600
gttgcagcmt caaccacgga ggctgagtac atggcagcag cagcagcagt caaggaagct    3660
ctatggctgc gtacactctt gagcgagctg cagctagaca tagacaacat cactatcatg    3720
gcagacaacc agtcagcaat caagcttctg cgcaatccta tctcatccat gagaaccaag    3780
cacattgayg tggcttatca ctttgctagg aacgcgtgg tgcgcaagga ggttgtgttc    3840
aggttcgttt ccacagagaa catggtggca gacatcatga ccaaggctct gagcgaagtc    3900
```
aagcatgtgc gatgttgcaa gggcatgggg gttggagttt aa            3942

<210> SEQ ID NO 27
<211> LENGTH: 3957
<212> TYPE: DNA
<213> ORGANISM: Chromochloris zofingiensis

<400> SEQUENCE: 27
atgacagaac tggagaagct gggtatccca aractkaacg accacaacta tgtcttctgg      60
cacatcaaga tgcgagccta cctgttgca agaggataca gcgcagcaat aacgaacgca      120
gaagacgcca acagtgacaa ggctcttgct tccatcactt tggctgtgga agatcatttt     180
ctacctacag trtacaawgc tgcaagtgcg aaggcagcat gggacgcgct ggaggcgttg     240
tttcagcagc ggagcgttgc caaccagctg aacctcacgc aggaactgaa caacctcaca     300
ctgcagcctg gggagaccat cacacagcta cttgctcgtg ccagaatcat atgggagcag     360
cttaaggcag ctggtatcga caagtcagag caggaggtgg cgttatcagt gttgtcagga     420
cttcctgccg acttcaacac cttagtgaca gtactacaga atcagtctgg tccmctyacy     480
ctgrgtggca tccagaaggc tgtcttgaca gaacagcaac gtgcaaataa ggttggggca     540
tcaacgtcta ctgcagcaag caccaaggct ttctacactc agaacggtcc caaccrtggc     600
argcttggtg acagcggtac caggaccagc aacttcaacc aggggaacrg caacaccaag     660
cagcaggagc agcgtaagtg ctactactgt ggcaagaagg ggcacctgaa agggactgc      720
agaaagaaga aggcagacga gcagcgtggc cccagtacca aggcttcaac aacaatggca     780
tggactgcag cctgcaacac cagcatcagc ctcagctcag gtacctgggt cctcgactct     840
ggagcatcaa gacacgtctg caaagaacgc agcctgatgc agaacctgca acagctgaac     900
cagccagtct acatcacgta cggcaacggt agcacagggg tggcacagac tatgggggag     960
gttgttctca cgacaggat ccgtctacgg aacgttttgt ttgatcccac tgctgttggc     1020
aatctccttt ccatccstac agcagctgcr ygtggagcac agtttaactt tgsagccart    1080
tgctgcacca ttcgagtaaa tggcagactg gtggcaatag cacagcagca wgayggtcac    1140
taytgcttgc actctgagca wrcasagtca gccactgcac tggcagccca gaccccgcag    1200
ctgtggcatc gtcgttttgg ccatctcagc taccagaata tggccaaggt ccccaacttg    1260
gtaacgggcg tccaagtscc aactgargcc tttcaggcag caggtcagca ggtgtgtgag    1320
ccatgtctac tkggcaaaca gacacgactg tctttccccg agtcagarac tgtcaggcag    1380
cagycactkg arctggtgca tatggacctc tgtggacctc tycctgtcaa gtcacttgga    1440
ggcagccagt acattgctac gttcctggay gactayacag gactgtcagt rgtggcattg    1500
ctcaaacaga agtcagacat ttcyaargtt gtgcctgacg tcttcaacat gctagagaaa    1560
cagagcaaca atcaggtgaa gggcgtccgc actgacaacg gcggggagta tgtcaacaat    1620
gtgmtgaaca gctactacag cagcaagggc atcatcgcac agcacacagt accatacagt    1680
cctcagcaga atgcaaggc agaaagactc aaccgaaccc tactggacaa ggcacgttcc    1740
atgctggcag atgcarggct accttctcag ctrtggggtg aggccgtggt aacagccaat   1800
tatcttagga accgttcacc agcagctggc aagacagcaa cccctgggaa ctgtttttt    1860
gggtcacggc cctctgtctc tcatcttcgc gtgtttgggg ccaaggcgtt tgcacagatc   1920
cccaaggaga aacgtggcaa gctggaccca aggagtcagc gtggcatcat ggttggatat   1980
gagccyaatg taaaggggta ccgtctactg cttccaaaca acaccatcac agtcagccgg   2040
gacgttgtat ttgatgaagg tgaccagcca ggagcartag acaccaactt ctatccagac   2100

```
ttggaagatg agcttgatgt tactgcagcc atcaacactg gatctaatgc agcaccttct    2160
gtcaatactt ctggaacagc tgagccacca ccatcagttg cagcacccgt cgacccacca    2220
atttcggcac agaccatgga aaacgtggga gccagcaaca gctcaacacc acaaggcagy    2280
gaggaagatc agcatcagca atcacgtaga agtagccggg ccaacattgg catggcacca    2340
ggcaactact gggaggccaa ctacattccc acatccaagc gtacagctac cggactgttg    2400
gcacagacat cagaaattgt tgagccagca acctatgamg aagcactaca gtcagactgt    2460
gcagagcagt ggcagcaagc catggacagc gagtacgcat cgctgatagc caatggaact    2520
tggaccttgg aaaaacccccc aacagacatt aggcccatcc ctgtcaagtg ggtgtataag    2580
gtgaaacgtg acaccagcgg gaacattgag cggttcaagg cacgcctggt ggccaagggt    2640
ttttggcaac aggaaggtgt ggattatgac gaagtgttcg ccccggtaag caagtatgct    2700
acctttcggg cactaatggc caaggcagca gaagaggaca tggaactaca caaattggat    2760
gtcaagactg cgttccttca aggcaacctg gaagaagatg tttggatcca gcagcctcgt    2820
ggctacgagg arggcagcag tgaactmgcc tgtcatctwc ayaaaccttt gtacgggctc    2880
aagcaggcyc ctcgrgcwtg gcatcagcgg ctacaacagg aactactggc agtaggctac    2940
acagcatcag cagcagaccc cagcctgtac tggtactgca tcaacgggga ctatgtgtac    3000
ctcctggtct aygtggatga tatcctgatt gcagccaagc agcttgagtc agtcaaggca    3060
gtcaagcagc agctrttagg cttatttgag tcgcgtgacc ttggagaagc wacatcctac    3120
cttggtatga gcattcagcg caacagacag acaggcayca tcaagatygg gcaccgactc    3180
atgatcacag agttactgga rargtatggy gcagtmgaca gcaaaathaa gtcartacca    3240
ctgtctccat ctatcaarct rgcyaaagat gaaggcgryc ccctagacaa ggaacattac    3300
ccttacagcc aactggttgg gagtctcatg taccttgcaa tcacctccag gccagacctc    3360
gccttttctg tgggggctct tgcacgctac atgtcatgcc caaccacwgt ccaytggcar    3420
gcagctaagg grgtrctacg ctacttggga ggaaccctgg actatggcat caccttttggt    3480
agcgacagca atgacctcat tggctactgt gacgcagact atgcgggaga cacagacaca    3540
cgcaagtcca ccagtggcta catattcata ctgcacggag gggccatyac ktggagtagt    3600
aagcgccagg caacagttgc agcmtcaacc acggaggctg agtacatggc agcagcagca    3660
gcagtcaagg aagctctatg gctgcgtaca ctcttgagcg agctgcagct agacatagac    3720
aacatcacta tcatggcaga caaccagtca gcaatcaagc ttctgcgcaa tcctatctca    3780
tccatgagaa ccaagcacat tgaygtggct tatcactttg ctagggaacg cgtggtgcgc    3840
aaggaggttg tgttcaggtt cgtttccaca gagaacatgg tggcagacat catgaccaag    3900
gctctgagcg aagtcaagca tgtgcgatgt tgcaagggca tggggttgg agtttaa      3957
```

<210> SEQ ID NO 28
<211> LENGTH: 626
<212> TYPE: DNA
<213> ORGANISM: Chromochloris zofingiensis

<400> SEQUENCE: 28

```
agaaacttga aatgcgtggg agcatctttg acagtacatg cctgactgcg tgggagtgtt     60
gaaatacggc ctttattcag tcagacctgc actgccagaa tccagaagtt gagcatcttt    120
gacagtacat gcctgactgc gtgggagtgt tgaaatacgg cctttattca gtcagacctg    180
cactgccaga atccagaagt tccagatggg ttctggaagy ccccagatgt ttcyagatgt    240
```

```
ttcyaratgt ktcyagaata ttggtgcatg acacgtgtca gtcactttgt ggtrgtagga    300
atctgtggta ggaatctgtg gtaggaatct gtggtaggat tcccagtagg tgaacacagt    360
tgccagtgga ttgccattgt gtcgtgagta tataaagaca cagacttgtc ccaatctgta    420
ayaytgtcca gcccgagysc caccgaggcc ccacgcttaa acacagaccg caacacagag    480
ctgaggatac tgagtcgcta gaacgactwa grcaacagat ttccatcagg ttatgggccc    540
acrcccacac gcacaatcgc tgtgctgctc agaaatttgt tgtgttcggc cataagtgtt    600
gtgtacagtt cgtcarcmag gtcacd                                        626

<210> SEQ ID NO 29
<211> LENGTH: 639
<212> TYPE: DNA
<213> ORGANISM: Chromochloris zofingiensis

<400> SEQUENCE: 29
agaaacttga aatgcgtggg agcatctttg acagtacatg cctgactgcg tgggagtgtt     60
gaaatacggc ctttattcag tcagacctgc actgccagaa tccagaagtt gagcatcttt    120
gacagtacat gcctgactgc gtgggagtgt tgaaatacgg cctttattca gtcagacctg    180
cactgccaga atccagaagt ttccagatgg ttctggaagy ccccagatgt ttcyagatgt    240
ttcyaratgt ktcyagaata ttggtgcatg acacgtgtca gtcactttgt ggtrgtagga    300
atctgtggta ggaatctgtg gtaggaatct gtggtaggaa tctgtggtag gattcccagt    360
aggtgaacac agttgccagt ggattgccat tgtgtcgtga gtatataaag acacagactt    420
gtcccaatct gtaayaytgt ccagcccgag ysccaccgag gccccacgct taaacacaga    480
ccgcaacaca gagctgagga tactgagtcg ctagaacgac twagrcaaca gatttccatc    540
aggttatggg cccacrccca cacgcacaat cgctgtgctg ctcagaaatt tgttgtgttc    600
ggccataagt gttgtgtaca gttcgtcarc maggtcacd                           639

<210> SEQ ID NO 30
<211> LENGTH: 652
<212> TYPE: DNA
<213> ORGANISM: Chromochloris zofingiensis

<400> SEQUENCE: 30
agaaacttga aatgcgtggg agcatctttg acagtacatg cctgactgcg tgggagtgtt     60
gaaatacggc ctttattcag tcagacctgc actgccagaa tccagaagtt gagcatcttt    120
gacagtacat gcctgactgc gtgggagtgt tgaaatacgg cctttattca gtcagacctg    180
cactgccaga atccagaagt ttccagatgg ttctggaagy ccccagatgt ttcyagatgt    240
ttcyaratgt ktcyagaata ttggtgcatg acacgtgtca gtcactttgt ggtrgtagga    300
atctgtggta ggaatctgtg gtaggaatct gtggtaggaa tctgtggtag gaatctgtgg    360
taggattccc agtaggtgaa cacagttgcc agtggattgc cattgtgtcg tgagtatata    420
aagacacaga cttgtcccaa tctgtaayay tgtccagccc gagysccacc gaggccccac    480
gcttaaacac agaccgcaac acagagctga ggatactgag tcgctagaac gactwagrca    540
acagatttcc atcaggttat gggcccacrc cacacgcac aatcgctgtg ctgctcagaa    600
atttgttgtg ttcggccata agtgttgtgt acagttcgtc arcmaggtca cd            652

<210> SEQ ID NO 31
<211> LENGTH: 656
<212> TYPE: DNA
<213> ORGANISM: Chromochloris zofingiensis
```

<400> SEQUENCE: 31

```
agaaacttga aatgcgtggg agcatctttg acagtacatg cctgactgcg tgggagtgtt      60
gaaatacggc ctttattcag tcagacctgc actgccagaa tccagaagtt gagcatcttt     120
gacagtacat gcctgactgc gtgggagtgt tgaaatacgg cctttattca gtcagacctg     180
cactgccaga atccagaagt ttccagatgg ttctggaagy ccccagatgt ttcyagatgt     240
ttcyaratgt ktcyagaagt ttctagaggt gtctagatgt ttctagaata ttggtgcatg     300
acacgtgtca gtcactttgt ggtrgtagga atctgtggta ggaatctgtg gtaggaatct     360
gtggtaggat tcccagtagg tgaacacagt tgccagtgga ttgccattgt gtcgtgagta     420
tataaagaca cagacttgtc ccaatctgta ayaytgtcca gcccgagysc caccgaggcc     480
ccacgcttaa acacagaccg caacacagag ctgaggatac tgagtcgcta gaacgactwa     540
grcaacagat ttccatcagg ttatgggccc acrcccacac gcacaatcgc tgtgctgctc     600
agaaatttgt tgtgttcggc cataagtgtt gtgtacagtt cgtcarcmag gtcacd         656
```

<210> SEQ ID NO 32
<211> LENGTH: 669
<212> TYPE: DNA
<213> ORGANISM: Chromochloris zofingiensis

<400> SEQUENCE: 32

```
agaaacttga aatgcgtggg agcatctttg acagtacatg cctgactgcg tgggagtgtt      60
gaaatacggc ctttattcag tcagacctgc actgccagaa tccagaagtt gagcatcttt     120
gacagtacat gcctgactgc gtgggagtgt tgaaatacgg cctttattca gtcagacctg     180
cactgccaga atccagaagt ttccagatgg ttctggaagy ccccagatgt ttcyagatgt     240
ttcyaratgt ktcyagaagt ttctagaggt gtctagatgt ttctagaata ttggtgcatg     300
acacgtgtca gtcactttgt ggtrgtagga atctgtggta ggaatctgtg gtaggaatct     360
gtggtaggaa tctgtggtag gattcccagt aggtgaacac agttgccagt ggattgccat     420
tgtgtcgtga gtatataaag acacagactt gtcccaatct gtaayaytgt ccagcccgag     480
ysccaccgag gccccacgct taaacacaga ccgcaacaca gagctgagga tactgagtcg     540
ctagaacgac twagrcaaca gatttccatc aggttatggg cccacrccca cacgcacaat     600
cgctgtgctg ctcagaaatt tgttgtgttc ggccataagt gttgtgtaca gttcgtcarc     660
maggtcacd                                                             669
```

<210> SEQ ID NO 33
<211> LENGTH: 682
<212> TYPE: DNA
<213> ORGANISM: Chromochloris zofingiensis

<400> SEQUENCE: 33

```
agaaacttga aatgcgtggg agcatctttg acagtacatg cctgactgcg tgggagtgtt      60
gaaatacggc ctttattcag tcagacctgc actgccagaa tccagaagtt gagcatcttt     120
gacagtacat gcctgactgc gtgggagtgt tgaaatacgg cctttattca gtcagacctg     180
cactgccaga atccagaagt ttccagatgg ttctggaagy ccccagatgt ttcyagatgt     240
ttcyaratgt ktcyagaagt ttctagaggt gtctagatgt ttctagaata ttggtgcatg     300
acacgtgtca gtcactttgt ggtrgtagga atctgtggta ggaatctgtg gtaggaatct     360
gtggtaggaa tctgtggtag gaatctgtgg taggattccc agtaggtgaa cacagttgcc     420
```

| | |
|---|---|
| agtggattgc cattgtgtcg tgagtatata aagacacaga cttgtcccaa tctgtaayay | 480 |
| tgtccagccc gagysccacc gaggccccac gcttaaacac agaccgcaac acagagctga | 540 |
| ggatactgag tcgctagaac gactwagrca acagatttcc atcaggttat gggcccacrc | 600 |
| ccacacgcac aatcgctgtg ctgctcagaa atttgttgtg ttcggccata agtgttgtgt | 660 |
| acagttcgtc arcmaggtca cd | 682 |

```
<210> SEQ ID NO 34
<211> LENGTH: 636
<212> TYPE: DNA
<213> ORGANISM: Chromochloris zofingiensis

<400> SEQUENCE: 34
```

| | |
|---|---|
| agaaacttga aatgcgtggg agcatctttg acagtacatg cctgactgcg tgggagtgtt | 60 |
| gaaatacggc ctttattcag tcagacctgc actgccagaa tccagaagtt gagcatcttt | 120 |
| gacagtacat gcctgactgc gtgggagtgt tgaaatacgg cctttattca gtcagacctg | 180 |
| cactgccaga atccagaagt ttccagatgg ttctggaagy ccccagatgt ttcyagatgt | 240 |
| ttcyaratgt ktcyaaatgt gtccagaata ttggtgcatg acacgtgtca gtcactttgt | 300 |
| ggtrgtagga atctgtggta ggaatctgtg gtaggaatct gtggtaggat tcccagtagg | 360 |
| tgaacacagt tgccagtgga ttgccattgt gtcgtgagta tataaagaca cagacttgtc | 420 |
| ccaatctgta ayaytgtcca gcccgagysc caccgaggcc ccacgcttaa acacagaccg | 480 |
| caacacagag ctgaggatac tgagtcgcta gaacgactwa grcaacagat tccatcaggg | 540 |
| ttatgggccc acrcccacac gcacaatcgc tgtgctgctc agaaatttgt tgtgttcggc | 600 |
| cataagtgtt gtgtacagtt cgtcarcmag gtcacd | 636 |

```
<210> SEQ ID NO 35
<211> LENGTH: 649
<212> TYPE: DNA
<213> ORGANISM: Chromochloris zofingiensis

<400> SEQUENCE: 35
```

| | |
|---|---|
| agaaacttga aatgcgtggg agcatctttg acagtacatg cctgactgcg tgggagtgtt | 60 |
| gaaatacggc ctttattcag tcagacctgc actgccagaa tccagaagtt gagcatcttt | 120 |
| gacagtacat gcctgactgc gtgggagtgt tgaaatacgg cctttattca gtcagacctg | 180 |
| cactgccaga atccagaagt ttccagatgg ttctggaagy ccccagatgt ttcyagatgt | 240 |
| ttcyaratgt ktcyaaatgt gtccagaata ttggtgcatg acacgtgtca gtcactttgt | 300 |
| ggtrgtagga atctgtggta ggaatctgtg gtaggaatct gtggtaggaa tctgtggtag | 360 |
| gattcccagt aggtgaacac agttgccagt ggattgccat tgtgtcgtga gtatataaag | 420 |
| acacagactt gtcccaatct gtaayaytgt ccagcccgag ysccaccgag gccccacgct | 480 |
| taaacacaga ccgcaacaca gagctgagga tactgagtcg ctagaacgac twagrcaaca | 540 |
| gatttccatc aggttatggg cccacrccca cacgcacaat cgctgtgctg ctcagaaatt | 600 |
| tgttgtgttc ggccataagt gttgtgtaca gttcgtcarc maggtcacd | 649 |

```
<210> SEQ ID NO 36
<211> LENGTH: 662
<212> TYPE: DNA
<213> ORGANISM: Chromochloris zofingiensis

<400> SEQUENCE: 36
```

| | |
|---|---|
| agaaacttga aatgcgtggg agcatctttg acagtacatg cctgactgcg tgggagtgtt | 60 |

```
gaaatacggc ctttattcag tcagacctgc actgccagaa tccagaagtt gagcatcttt      120
gacagtacat gcctgactgc gtgggagtgt tgaaatacgg cctttattca gtcagacctg      180
cactgccaga atccagaagt ttccagatgg ttctggaagy ccccagatgt ttcyagatgt      240
ttcyaratgt ktcyaaatgt gtccagaata ttggtgcatg acacgtgtca gtcactttgt      300
ggtrgtagga atctgtggta ggaatctgtg gtaggaatct gtggtaggaa tctgtggtag      360
gaatctgtgg taggattccc agtaggtgaa cacagttgcc agtggattgc cattgtgtcg      420
tgagtatata aagacacaga cttgtcccaa tctgtaayay tgtccagccc gagysccacc      480
gaggccccac gcttaaacac agaccgcaac acagagctga ggatactgag tcgctagaac      540
gactwagrca acagatttcc atcaggttat gggcccacrc ccacacgcac aatcgctgtg      600
ctgctcagaa atttgttgtg ttcggccata agtgttgtgt acagttcgtc arcmaggtca      660 cd                                                                    662

<210> SEQ ID NO 37
<211> LENGTH: 666
<212> TYPE: DNA
<213> ORGANISM: Chromochloris zofingiensis

<400> SEQUENCE: 37
agaaacttga aatgcgtggg agcatctttg acagtacatg cctgactgcg tgggagtgtt       60
gaaatacggc ctttattcag tcagacctgc actgccagaa tccagaagtt gagcatcttt      120
gacagtacat gcctgactgc gtgggagtgt tgaaatacgg cctttattca gtcagacctg      180
cactgccaga atccagaagt ttccagatgg ttctggaagy ccccagatgt ttcyagatgt      240
ttcyaratgt ktcyaaatgt gtccagaagt ttctagaggt gtctagatgt ttctagaata      300
ttggtgcatg acacgtgtca gtcactttgt ggtrgtagga atctgtggta ggaatctgtg      360
gtaggaatct gtggtaggat tcccagtagg tgaacacagt tgccagtgga ttgccattgt      420
gtcgtgagta tataaagaca cagacttgtc ccaatctgta ayaytgtcca gcccgagysc      480
caccgaggcc ccacgcttaa acacagaccg caacacagag ctgaggatac tgagtcgcta      540
gaacgactwa grcaacagat ttccatcagg ttatgggccc acrcccacac gcacaatcgc      600
tgtgctgctc agaaatttgt tgtgttcggc cataagtgtt gtgtacagtt cgtcarcmag      660 gtcacd                                                                666

<210> SEQ ID NO 38
<211> LENGTH: 679
<212> TYPE: DNA
<213> ORGANISM: Chromochloris zofingiensis

<400> SEQUENCE: 38
agaaacttga aatgcgtggg agcatctttg acagtacatg cctgactgcg tgggagtgtt       60
gaaatacggc ctttattcag tcagacctgc actgccagaa tccagaagtt gagcatcttt      120
gacagtacat gcctgactgc gtgggagtgt tgaaatacgg cctttattca gtcagacctg      180
cactgccaga atccagaagt ttccagatgg ttctggaagy ccccagatgt ttcyagatgt      240
ttcyaratgt ktcyaaatgt gtccagaagt ttctagaggt gtctagatgt ttctagaata      300
ttggtgcatg acacgtgtca gtcactttgt ggtrgtagga atctgtggta ggaatctgtg      360
gtaggaatct gtggtaggaa tctgtggtag gattcccagt aggtgaacac agttgccagt      420
ggattgccat tgtgtcgtga gtatataaag acacagactt gtcccaatct gtaayaytgt      480
```

| | | |
|---|---|---|
| ccagcccgag ysccaccgag gccccacgct taaacacaga ccgcaacaca gagctgagga | 540 | |
| tactgagtcg ctagaacgac twagrcaaca gatttccatc aggttatggg cccacrccca | 600 | |
| cacgcacaat cgctgtgctg ctcagaaatt tgttgtgttc ggccataagt gttgtgtaca | 660 | |
| gttcgtcarc maggtcacd | 679 | |

<210> SEQ ID NO 39
<211> LENGTH: 692
<212> TYPE: DNA
<213> ORGANISM: Chromochloris zofingiensis

<400> SEQUENCE: 39

| | |
|---|---|
| agaaacttga aatgcgtggg agcatctttg acagtacatg cctgactgcg tgggagtgtt | 60 |
| gaaatacggc ctttattcag tcagacctgc actgccagaa tccagaagtt gagcatcttt | 120 |
| gacagtacat gcctgactgc gtgggagtgt tgaaatacgg cctttattca gtcagacctg | 180 |
| cactgccaga atccagaagt ttccagatgg ttctggaagy ccccagatgt ttcyagatgt | 240 |
| ttcyaratgt ktcyaaatgt gtccagaagt ttctagaggt gtctagatgt ttctagaata | 300 |
| ttggtgcatg acacgtgtca gtcactttgt ggtrgtagga atctgtggta ggaatctgtg | 360 |
| gtaggaatct gtggtaggaa tctgtggtag gaatctgtgg taggattccc agtaggtgaa | 420 |
| cacagttgcc agtggattgc cattgtgtcg tgagtatata aagacacaga cttgtcccaa | 480 |
| tctgtaayay tgtccagccc gagysccacc gaggccccac gcttaaacac agaccgcaac | 540 |
| acagagctga ggatactgag tcgctagaac gactwagrca acagatttcc atcaggttat | 600 |
| gggcccacrc ccacacgcac aatcgctgtg ctgctcagaa atttgttgtg ttcggccata | 660 |
| agtgttgtgt acagttcgtc arcmaggtca cd | 692 |

<210> SEQ ID NO 40
<211> LENGTH: 74
<212> TYPE: DNA
<213> ORGANISM: Artificial Sequence
<220> FEATURE:
<223> OTHER INFORMATION: Synthetic construct

<400> SEQUENCE: 40

| | |
|---|---|
| aagggtttag ggtttagggt ttagggttta gggtttaggg tttagggttt agggtttagg | 60 |
| gtttagggtt tagg | 74 |

<210> SEQ ID NO 41
<211> LENGTH: 14
<212> TYPE: DNA
<213> ORGANISM: Chromochloris zofingiensis

<400> SEQUENCE: 41

| | |
|---|---|
| cttggtattg gggc | 14 |